United States Patent
Bloms-Funke et al.

(10) Patent No.: US 9,775,843 B2
(45) Date of Patent: Oct. 3, 2017

(54) TREATMENT AND/OR PROPHYLAXIS OF TSPO MEDIATED DISEASES AND/OR DISORDERS

(71) Applicant: GRÜNENTHAL GMBH, Aachen (DE)

(72) Inventors: Petra Bloms-Funke, Würselen (DE); Gregor Bahrenberg, Monschau-Konzen (DE); Wolfgang Schröder, Aachen (DE); Sven Kühnert, Düren (DE); Simon Lucas, Wolfsgraben (AT)

(73) Assignee: GRÜNENTHAL GMBH, Aachen (DE)

( * ) Notice: Subject to any disclaimer, the term of this patent is extended or adjusted under 35 U.S.C. 154(b) by 0 days.

(21) Appl. No.: 14/434,943

(22) PCT Filed: Oct. 11, 2013

(86) PCT No.: PCT/EP2013/003064
§ 371 (c)(1),
(2) Date: Apr. 10, 2015

(87) PCT Pub. No.: WO2014/056620
PCT Pub. Date: Apr. 17, 2014

(65) Prior Publication Data
US 2015/0290203 A1    Oct. 15, 2015

(30) Foreign Application Priority Data
Oct. 11, 2012 (EP) ..................................... 12007118

(51) Int. Cl.
*A61K 31/44* (2006.01)
*A61K 31/5377* (2006.01)
*C07D 213/82* (2006.01)
*C07D 215/48* (2006.01)
*A61K 31/47* (2006.01)

(52) U.S. Cl.
CPC .......... *A61K 31/5377* (2013.01); *A61K 31/44* (2013.01); *A61K 31/47* (2013.01); *C07D 213/82* (2013.01); *C07D 215/48* (2013.01)

(58) Field of Classification Search
None
See application file for complete search history.

(56) References Cited

U.S. PATENT DOCUMENTS

| | | | |
|---|---|---|---|
| 8,552,200 B2* | 10/2013 | Kuhnert | C07D 213/82 546/297 |
| 9,168,259 B2* | 10/2015 | Kuhnert | C07D 213/82 |
| 9,278,103 B2* | 3/2016 | Kuhnert | C07D 213/82 |
| 2003/0144283 A1 | 7/2003 | Coleman et al. | |
| 2007/0010551 A1 | 1/2007 | Bladh et al. | |
| 2008/0214616 A1 | 9/2008 | Blaszczak et al. | |
| 2009/0076086 A1 | 3/2009 | Merla et al. | |
| 2012/0053206 A1 | 3/2012 | Kuehnert et al. | |
| 2012/0101079 A1 | 4/2012 | Kuehnert et al. | |
| 2012/0184550 A1 | 7/2012 | Kuehnert et al. | |
| 2012/0220627 A1 | 8/2012 | Kuehnert et al. | |

FOREIGN PATENT DOCUMENTS

| | | |
|---|---|---|
| CN | 101392001 A | 3/2009 |
| EP | 1 464 335 A2 | 10/2004 |
| WO | 99 29661 A1 | 6/1999 |
| WO | 2004 021509 A1 | 3/2004 |
| WO | 2005 021509 A1 | 3/2005 |
| WO | 2005 049608 A1 | 6/2005 |
| WO | 2010 102809 A1 | 9/2010 |
| WO | 2010 102811 A1 | 9/2010 |
| WO | 2011 099305 A1 | 8/2011 |
| WO | 2012 025237 A1 | 3/2012 |
| WO | 2012 025238 A1 | 3/2012 |
| WO | 2012 025239 A1 | 3/2012 |
| WO | 2012025236 A1 | 3/2012 |
| WO | 2012 052167 A1 | 4/2012 |

OTHER PUBLICATIONS

International Search Report issued by the EPO mailed Feb. 18, 2014.
Cappelli et al., "Synthesis and Structure Activity Relationship Studies in Translocator Protein Ligands Based on a Pyrazolo [3,4-b]quinolin Scaffold"; Journal of Medicinal Chemistry, 2011, 54, pp. 7165-7175.
Anzini, et al. "Mapping and Filling the Peripheral Benzodiazepine Receptor Binding Site by Carboxamide Derivatives . . . ", J. Med. Chem., 2001, 44, pp. 1134-1150.
Le Fur, et al., "Differentiation Between Two Ligands for Peripheral Benzodiazepine Binding Sites"; Life Sciences, vol. 33, pp. 449-457.
Gennaro, "Remington's Pharmaceutical Sciences", 17th Edition, Mac Publishing Company, 1985, Part 8, chapters 76-93.

* cited by examiner

*Primary Examiner* — Samantha Shterengarts
(74) *Attorney, Agent, or Firm* — Norris McLaughlin & Marcus, P.A.

(57) ABSTRACT

The invention relates to certain compounds for the use in the treatment and/or prophylaxis of diseases and/or disorders that are, at least partially, mediated by TSPO activity.

2 Claims, No Drawings

TREATMENT AND/OR PROPHYLAXIS OF TSPO MEDIATED DISEASES AND/OR DISORDERS

This application is a 371 of International Patent Application No. PCT/EP2013/003064, filed Oct. 11, 2013, which claims foreign priority benefit under 35 U.S.C. §119 of the European Patent Application No. 12007118.8, filed Oct. 11, 2012, the disclosures of which patent applications are incorporated herein by reference.

The invention relates to certain compounds for the use in the treatment and/or prophylaxis of diseases and/or disorders that are, at least partially, mediated by TSPO activity.

The translocator protein (18 kDa) (TSPO), also known as peripherial-type benzodiazepine receptor, peripheral BZD receptor or mitochondrial benzodiazepine receptor, is a five transmembrane domain protein that is localized primarily in the outer mitochondrial membrane and expressed predominantly in steroid-synthesizing tissues, including the brain. TSPO is involved in the translocation of cholesterol from the outer to the inner mitochondrial membrane, which is the rate-limiting step in the synthesis of steroids and one of the most well-characterized functions of this protein.

Radiolabeled TSPO ligands are used as neuroimaging agents and are known as important diagnostic tools. TSPO also seems to be a sensitive biomarker of brain damage and neurodegeneration. The binding of labeled TSPO ligands can be visualized and quantified by in vivo imaging techniques such as positron emission tomography (PET) and single photon emission computed tomography (SPECT). Altered TSPO expression has been shown in numerous neurological and psychiatric disorders.

Therefore, the modulation of the activity of this protein provides an option for treatment of diseases related to disturbed cholesterol metabolism and steroidogenesis, but also aptotosis and cell proliferation.

Furthermore, its potential use for neuroprotection, limiting immunological disorders, inflammatory diseases including neuroinflammation and arthritis, encephalomyelitis, irritable bowel syndrome, promoting regeneration, and treating dysfunctions of the nervous system has been envisaged (Rupprecht et al., Nature Reviews, 2010, Vol. 9, 971).

TSPO ligands also provide therapeutic potential in neuroregeneration, and anxiety, particularly for the treatment of neurodegenerative disorders such as Alzheimer's disease, head trauma, frontotemporal dementia, multiple sclerosis, Huntington's disease, amyotrophic lateral sclerosis, Morbus Parkinson, cerebrovascular disorders, cerebral ischemia, stroke, tumours including brain tumours, and neuro-degenerative diseases related to peripheral nervous system lesions and neuropathologies.

Various TSPO ligands have been shown to exert acute anxiolytic/anticonflict activity in rodents and humans. Therefore, the modulation of TSPO activity additionally offers treatment options for psychiatric disorders such as anxiety disorders including panic attacks, stress disorders including posttraumatic stress disorder, depression including major depressive disorders, dysthymia, angina pectoris (Rupprecht et al., Nature Reviews, 2010, Vol. 9, 971).

It was therefore an object of the invention to provide compounds having advantages over the compounds known for TSPO activity. These compounds should be suitable in particular as pharmacological active ingredients in pharmaceutical compositions, preferably in pharmaceutical compositions for the treatment and/or prophylaxis of disorders and/or diseases which are, at least partially, mediated by TPSO activity.

That object is achieved by the subject-matter of the patent claims. It has been found, surprisingly, that compounds of the general formula (I) given below are suitable for the use in the treatment and/or prophylaxis of disorders and/or diseases which are, at least partially, mediated by TPSO activity.

Compounds according to general formula (I) are known and have been described for their activity on KCNQ2/3 K⁺ channels (WO 2010/102809 A1; WO 2010/102811 A1; WO 2012/025236 A1; WO 2012/025237 A1; WO 2012/025238 A1; WO 2012/025239 A1; WO 2012/0052167 A1).

No hint for modulation of TSPO activity and the treatment and/or prophylaxis of disorders and/or diseases, which are, at least partially, mediated by TPSO activity, however, is provided in the prior art.

The first aspect of the present invention therefore relates to a compound of general formula (I),

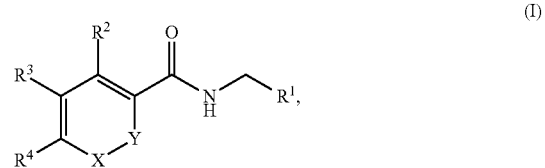

for the use in the treatment and/or prophylaxis of disorders and/or diseases which are mediated, at least in part, by TSPO (translocator protein 18 kDa), wherein X—Y represents N(R⁵)—C(=O) or N(R⁵)—C(=S) or N=C(R⁶)

R¹ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

R² represents H; F; Cl; Br; I; CN; CF₃; C(=O)H; NO₂; OCF₃; SCF₃; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)₂, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)₂—$C_{1-4}$-aliphatic residue, a S(=O)₂—O—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

R³ represents H; F; Cl; Br; I; CN; CF₃; SCF₃; NO₂; OCF₃; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^4$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted; or represents $N(R^7)(R^8)$,
  wherein
    $R^7$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;
    on the condition that if $R^7$ denotes a 3 to 10 membered heterocycloaliphatic residue or a heteroaryl, the 3 to 10 membered heterocycloaliphatic residue or the heteroaryl is linked via a carbon atom;
    $R^8$ denotes H or a $C_{1-10}$-aliphatic residue, unsubstituted or mono- or polysubstituted;
    or
    $R^7$ and $R^8$ form together with the nitrogen atom connecting them a 3 to 10 membered heterocycloaliphatic residue, unsubstituted or mono- or polysubstituted;

or $R^3$ and $R^4$ represent CH=CH—CH=CH,
  wherein one or more H-Atoms independently of one another may be replaced by one a radical selected from the group consisting of F; Cl; Br; I; CN; $CF_3$; C(=O)H; C(=O)—OH; C(=O)—$NH_2$; $SCF_3$; $S(=O)_2$—OH; $NO_2$; $OCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, a $S(=O)_2$—O—$C_{1-4}$-aliphatic residue, wherein the $C_{1-4}$ aliphatic residue may be in each case be unsubstituted or mono- or polysubstituted; a NH($C_{1-4}$ aliphatic residue), a N($C_{1-4}$ aliphatic residue)$_2$, a NH—C(=O)—$C_{1-4}$ aliphatic residue, a NH—$S(=O)_2$—$C_{1-4}$-aliphatic residue, a N($C_{1-4}$ aliphatic residue)-C(=O)—$C_{1-4}$ aliphatic residue, or a N($C_{1-4}$ aliphatic residue)-$S(=O)_2$—$C_{1-4}$ aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^5$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
  on the condition that if $R^5$ denotes a 3 to 10 membered heterocycloaliphatic residue, the 3 to 10 membered heterocycloaliphatic residue is linked via a carbon atom, $R^6$ represents a $C_{2-10}$-aliphatic residue or a $C_{2-10}$-heteroaliphatic residue, in each case unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
or
denotes S—$R^{11}$, O—$R^{12}$ or $N(R^9R^{10})$,
  wherein
    $R^{11}$ and $R^{12}$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group or a $C_{2-8}$-heteroaliphatic group, which in turn may be unsubstituted or mono- or polysubstituted;
      on the condition that if $R^{11}$ or $R^{12}$ denotes a 3 to 10 membered heterocycloaliphatic residue, the 3 to 10 membered heterocycloaliphatic residue is linked via a carbon atom,
    $R^9$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
      on the condition that if $R^9$ denotes a 3 to 10 membered heterocycloaliphatic residue, the 3 to 10 membered heterocycloaliphatic residue is linked via a carbon atom;
    $R^{10}$ denotes a $C_{1-10}$-aliphatic residue, unsubstituted or mono- or polysubstituted;
    or
    $R^9$ and $R^{10}$ form together with the nitrogen atom connecting them a 3 to 10 membered heterocycloaliphatic residue, unsubstituted or mono- or polysubstituted;
  in the form of the free compounds, the racemate, the enantiomers, diastereomers, mixtures of the enantiomers or diastereomers in any mixing ratio, or of an individual enantiomer or diastereomer, or in the form of the salts of physiologically acceptable acids or bases.

The term "mono- or polysubstituted" with respect to an "aliphatic group" and an "aliphatic residue", "alkyl group", "alkyl residue", "heteroaliphatic group", "heteroalipahtic residue", "heteroalkyl group", "heteroalkyl residue", "heterocyloaliphatic group", "heterocycloalipahtic residue", "heterocycloalkyl group", "heterocycloalkyl residue", "cycloalipahtic residue" and "cycloalkyl" within the scope of the present invention is the substitution of one or more hydrogen atoms, in each case independently of one another, by F; Cl; Br; I; $NO_2$; $CF_3$; CN; =O; $C_{1-8}$-alkyl; $C_{2-8}$-heteroalkyl; aryl; heteroaryl; $C_{3-10}$-cycloalkyl; heterocyclyl; $C_{1-8}$-alkyl- or $C_{2-8}$-heteroalkyl-bridged aryl, heteroaryl, $C_{3-10}$-cycloalkyl or heterocyclyl; CHO; C(=O)$C_{1-8}$-alkyl; C(=O)aryl; C(=O)heteroaryl; $CO_2$H; C(=O)O—$C_{1-8}$-alkyl; C(=O)O-aryl; C(=O)O-heteroaryl; $CONH_2$; C(=O)NH—$C_{1-8}$-alkyl; C(=O)N($C_{1-8}$-alkyl)$_2$; C(=O)

NH-aryl; C(=O)N(aryl)$_2$; C(=O)NH-heteroaryl; C(=O)N(heteroaryl)$_2$; C(=O)N(C$_{1-8}$-alkyl)(aryl); C(=O)N(C$_{1-8}$-alkyl)(heteroaryl); C(=O)N(heteroaryl)(aryl); OH; O—C$_{1-8}$-alkyl; OCF$_3$; O—(C$_{1-8}$-alkyl)-OH; O—(C$_{1-8}$-alkyl)-O—C$_{1-8}$-alkyl; O-benzyl; O-aryl; O-heteroaryl; O—C(=O)C$_{1-8}$-alkyl; O—C(=O)aryl; O—C(=O)heteroaryl; NH$_2$; NH—C$_{1-8}$-alkyl; N(C$_{1-8}$-alkyl)$_2$; NH—C(=O)C$_{1-8}$-alkyl; N(C$_{1-8}$-alkyl)-C(=O)C$_{1-8}$-alkyl; N(C(=O)C$_{1-8}$-alkyl)$_2$; NH—C(=O)-aryl; NH—C(=O)-heteroaryl; NH—S(=O)$_2$—C$_{1-8}$-alkyl; NH—S(=O)$_2$-aryl; NH—S(=O)$_2$-heteroaryl; SH; S—C$_{1-8}$-alkyl; SCF$_3$; S-benzyl; S-aryl; S-heteroaryl; S(=O)$_2$C$_{1-8}$-alkyl; S(=O)$_2$aryl; S(=O)$_2$heteroaryl; S(=O)$_2$OH; S(=O)$_2$O—C$_{1-8}$-alkyl; S(=O)$_2$O-aryl; S(=O)$_2$O-heteroaryl; S(=O)$_2$—NH—C$_{1-8}$-alkyl; S(=O)$_2$—NH-aryl; and S(=O)$_2$—NH—C$_{1-8}$-heteroaryl.

The term "mono- or polysubstituted" with respect to "aryl" and a "heteroaryl" within the scope of the present invention is the substitution of one or more hydrogen atoms, in each case independently of one another, by F; Cl; Br; I; NO$_2$; CF$_3$; CN; C$_{1-8}$-alkyl; C$_{2-8}$-heteroalkyl; aryl; heteroaryl; C$_{3-10}$-cycloalkyl; heterocyclyl; C$_{1-8}$-alkyl- or C$_{2-8}$-heteroalkyl-bridged aryl, heteroaryl, C$_{3-10}$-cycloalkyl or heterocyclyl; CHO; C(=O)C$_{1-8}$-alkyl; C(=O)aryl; C(=O)heteroaryl; CO$_2$H; C(=O)O—C$_{1-8}$-alkyl; C(=O)O-aryl; C(=O)O-heteroaryl; CONH$_2$; C(=O)NH—C$_{1-8}$-alkyl; C(=O)N(C$_{1-8}$-alkyl)$_2$; C(=O)NH-aryl; C(=O)N(aryl)$_2$; C(=O)NH-heteroaryl; C(=O)N(heteroaryl)$_2$; C(=O)N(C$_{1-8}$-alkyl)(aryl); C(=O)N(C$_{1-8}$-alkyl)(heteroaryl); C(=O)N(heteroaryl)(aryl); OH; O—C$_{1-8}$-alkyl; OCF$_3$; O—(C$_{1-8}$-alkyl)-OH; O—(C$_{1-8}$-alkyl)-O—C$_{1-8}$-alkyl; O-benzyl; O-aryl; O-heteroaryl; O—C(=O)C$_{1-8}$-alkyl; O—C(=O)aryl; O—C(=O)heteroaryl; NH$_2$; NH—C$_{1-8}$-alkyl; N(C$_{1-8}$-alkyl)$_2$; NH—C(=O)C$_{1-8}$-alkyl; N(C$_{1-8}$-alkyl)-C(=O)C$_{1-8}$-alkyl; N(C(=O)C$_{1-8}$-alkyl)$_2$; NH—C(=O)-aryl; NH—C(=O)-heteroaryl; SH; SCF$_3$; S-benzyl; S-aryl; S-heteroaryl; S(=O)$_2$C$_{1-8}$-alkyl; S(=O)$_2$aryl; S(=O)$_2$heteroaryl; S(=O)$_2$OH; S(=O)$_2$O—C$_{1-8}$-alkyl; S(=O)$_2$O-aryl; S(=O)$_2$O-heteroaryl; S(=O)$_2$—NH—C$_{1-8}$-alkyl; S(=O)$_2$—NH-aryl; S(=O)$_2$—NH—C$_{1-8}$-heteroaryl;

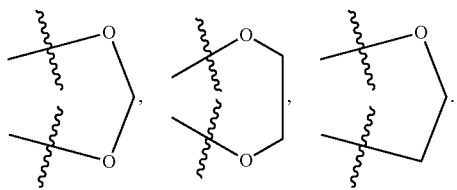

Within the scope of this invention, the terms "alkyl" and "aliphatic residue" or "aliphatic group" or "C$_{1-10}$-alkyl", "C$_{1-8}$-alkyl", "C$_{1-6}$-alkyl", "C$_{1-4}$-alkyl", "C$_{1-2}$-alkyl" and "C$_{2-6}$-alkyl" include acyclic saturated or unsaturated aliphatic hydrocarbon radicals, which can be branched or unbranched as well as unsubstituted or mono- or poly-substituted, having from 1 to 10 or from 1 to 8 or from 1 to 6 or from 1 to 4 or from 1 to 2 or from 2 to 6 carbon atoms, that is to say C$_{1-10}$-alkanyls, C$_{2-10}$-alkenyls and C$_{2-10}$-alkynyls or C$_{1-8}$-alkanyls, C$_{2-8}$-alkenyls and C$_{2-8}$-alkynyls or C$_{1-6}$-alkanyls, C$_{2-6}$-alkenyls and C$_{2-6}$-alkynyls or C$_{1-4}$-alkanyls, C$_{2-4}$-alkenyls and C$_{2-4}$-alkynyls or C$_{1-2}$-alkanyls, C$_2$-alkenyls and C$_2$-alkynyls or C$_{2-6}$-alkanyls, C$_{2-6}$-alkenyls and C$_{2-6}$-alkynyls. Alkenyls contain at least one C=C double bond and alkynyls contain at least one C=C triple bond. Alkyl is preferably selected from the group comprising methyl, ethyl, n-propyl, 2-propyl, n-butyl, isobutyl, sec-butyl, tert-butyl, n-pentyl, isopentyl, neopentyl, n-hexyl, n-heptyl, n-octyl, n-nonyl, n-decyl, ethenyl (vinyl), ethynyl, propenyl (—CH$_2$CH=CH$_2$, —CH=CH—CH$_3$, —C(=CH$_2$)—CH$_3$), propynyl (—CH—C≡CH, —C≡C—CH$_3$), butenyl, butynyl, pentenyl, pentynyl, hexenyl and hexynyl, heptenyl, heptynyl, octenyl, octynyl, nonenyl, nonynyl, decenyl and decynyl.

Within the scope of this invention, the terms "heteroalkyl" or "C$_{2-10}$-heteroalkyl" and "C$_{2-8}$-heteroalkyl" or "heteroaliphatic" or "C$_{2-10}$-heteroaliphatic" and "C$_{2-8}$-heteroaliphatic" include acyclic aliphatic saturated or unsaturated hydrocarbon radicals having from 2 to 10 carbon atoms, that is to say C$_{2-10}$-heteroalkanyls, C$_{2-10}$-heteroalkenyls and C$_{2-10}$-heteroalkynyls, or having from 2 to 8 carbon atoms, that is to say C$_{2-8}$-heteroalkanyls, C$_{2-8}$-heteroalkenyls and C$_{2-8}$-heteroalkynyls, which in each case can be branched or unbranched as well as unsubstituted or mono- or poly-substituted and in which at least one carbon atom, optionally also two or three carbon atoms, have been replaced by a heteroatom or heteroatom group in each case selected independently of one another from the group consisting of O, N, NH and N(C$_{1-8}$-alkyl), preferably N(CH$_3$), wherein the initial carbon atom of a C$_{2-10}$-heteroalkyl or of a C$_{2-8}$-heteroalkyl, via which the C$_{2-10}$-heteroalkyl or C$_{2-8}$-heteroalkyl is bonded to the respective general structure of higher order, cannot be replaced by a heteroatom or heteroatom group and adjacent carbon atoms cannot simultaneously be replaced by a heteroatom or heteroatom group. The heteroatom groups NH and N(C$_{1-8}$-alkyl) of the heteroalkyl can optionally be mono- or poly-substituted. C$_{2-10}$-Heteroalkenyls and C$_{2-8}$-heteroalkenyls contain at least one C=C or C=N double bond and C$_{2-10}$-heteroalkynyls and C$_{2-8}$-heteroalkynyls contain at least one C=C triple bond. Heteroalkyl is preferably selected from the group comprising —CH$_2$—O—CH$_3$, —CH$_2$—CH$_2$—O—CH$_3$, —CH$_2$—CH$_2$—O—CH$_2$—CH$_3$, —CH$_2$—CH$_2$—O—CH$_2$—CH$_2$—O—CH$_3$, —CH=CH—O—CH$_3$, —CH=CH—O—CH$_2$—CH$_3$, =CH—O—CH$_3$, =CH—O—CH$_2$—CH$_3$, =CH—CH$_2$—O—CH$_2$—CH$_3$, =CH—CH$_2$—O—CH$_3$, —CH$_2$—NH—CH$_3$, —CH$_2$—CH$_2$—NH—CH$_3$, —CH$_2$—CH$_2$—NH—CH$_2$—CH$_3$, —CH$_2$—CH$_2$—NH—CH$_2$—CH$_2$—NH—CH$_3$, —CH=CH—NH—CH$_3$, —CH=CH—NH—CH$_2$—CH$_3$, —CH=CH—N(CH$_3$)—CH$_2$—CH$_3$, =CH—NH—CH$_3$, =CH—NH—CH$_2$—CH$_3$, =CH—CH$_2$—NH—CH$_2$—CH$_3$, =CH—CH$_2$—NH—CH$_3$, —CH$_2$—N(CH$_3$)—CH$_3$, —CH$_2$—CH$_2$—N(CH$_3$)—CH$_3$, —CH$_2$—CH$_2$—N(CH$_3$)—CH$_2$—CH$_3$, —CH$_2$—CH$_2$—N(CH$_3$)—CH$_3$, CH$_2$—CH$_2$—N(CH$_3$)—CH$_3$, CH$_2$—CH$_2$—NH—CH$_2$—CH$_2$—O—CH$_3$, CH$_2$—CH$_2$—O—CH$_2$—CH$_2$—NH—CH$_3$, CH$_2$—CH$_2$—N(CH$_3$)—CH$_2$—CH$_2$—O—CH$_3$, CH$_2$—CH$_2$—O—CH$_2$—CH$_2$—N(CH$_3$)—CH$_3$, CH$_2$—NH—CH$_2$—O—CH$_3$, CH$_2$—O—CH$_2$—NH—CH$_3$, CH$_2$—N(CH$_3$)—CH$_2$—O—CH$_3$, CH$_2$—O—CH$_2$—N(CH$_3$)—CH$_3$, —CH=CH—N(CH$_3$)—CH$_3$, =CH—N(CH$_3$)—CH$_3$, =CH—N(CH$_3$)—CH$_2$—CH$_3$, =CH—CH$_2$—N(CH$_3$)—CH$_2$—CH$_3$, =CHCH$_2$—N(CH$_3$)—CH$_3$, —CH$_2$CH$_2$=N(CH$_3$) and —CH$_2$=N(CH$_3$).

For the purposes of this invention, the terms "cycloalkyl" or "C$_{3-10}$-cycloalkyl", "C$_{3-7}$-cycloalkyl" and "C$_{3-8}$-cycloalkyl" or "cycloaliphatic" denote cyclic aliphatic hydrocarbons having 3, 4, 5, 6, 7, 8, 9 or 10 carbon atoms or having 3, 4, 5, 6 or 7 carbon atoms or having 3, 4, 5, 6, 7 or 8 carbon atoms, wherein the hydrocarbons can be saturated or unsaturated (but not aromatic), unsubstituted or mono- or poly-substituted. The bonding of the cycloalkyl to the general structure of higher order can take place via any desired and possible ring member of the cycloalkyl radical. The cycloalkyl radicals can also be fused with further saturated, (partially) unsaturated, (hetero)cyclic, aromatic or heteroaromatic ring systems, that is to say with cycloalkyl, heterocyclyl, aryl or heteroaryl, which can themselves be unsubstituted or mono- or poly-substituted. The cycloalkyl radicals can further be bridged one or more times, as, for example, in the case of adamantyl, bicyclo[2.2.1]heptyl or bicyclo[2.2.2]octyl. Cycloalkyl is preferably selected from the group comprising cyclopropyl, cyclobutyl, cyclopentyl, cyclohexyl, cycloheptyl, cyclooctyl, cyclononyl, cyclodecyl, adamantyl,

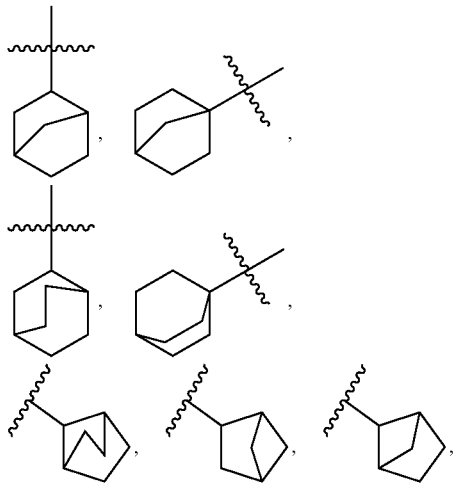

cyclopentenyl, cyclohexenyl, cycloheptenyl and cyclooctenyl.

The term "heterocyclyl" or "heterocycloalkyl" or "heterocycloaliphatic" includes aliphatic saturated or unsaturated (but not aromatic) cycloalkyls having from three to ten, that is to say 3, 4, 5, 6, 7, 8, 9 or 10, ring members, in which at least one carbon atom, optionally also two or three carbon atoms, has been replaced by a heteroatom or heteroatom group in each case selected independently of one another from the group consisting of O, S, N, NH and $N(C_{1-8}$-alkyl), preferably $N(CH_3)$, wherein the ring members can be unsubstituted or mono- or poly-substituted. The bonding of the heterocyclyl to the general structure of higher order can take place via any desired and possible ring member of the heterocyclyl radical. The heterocyclyl radicals can also be fused with further saturated, (partially) unsaturated (hetero) cyclic or aromatic or heteroaromatic ring systems, that is to say with cycloalkyl, heterocyclyl, aryl or heteroaryl, which can themselves be unsubstituted or mono- or poly-substituted. Heterocyclyl radicals are preferably selected from the group comprising azetidinyl, aziridinyl, azepanyl, azocanyl, diazepanyl, dithiolanyl, dihydroquinolinyl, dihydropyrrolyl, dioxanyl, dioxolanyl, dihydroindenyl, dihydropyridinyl, dihydrofuranyl, dihydroisoquinolinyl, dihydroindolinyl, dihydroisoindolyl, imidazolidinyl, isoxazolidinyl, morpholinyl, oxiranyl, oxetanyl, pyrrolidinyl, piperazinyl, piperidinyl, pyrazolidinyl, pyranyl, tetrahydropyrrolyl, tetrahydropyranyl, tetrahydroquinolinyl, tetrahydroisoquinolinyl, tetrahydroindolinyl, tetrahydrofuranyl, tetrahydropyridinyl, tetrahydrothiophenyl, tetrahydropyridoindolyl, tetrahydronaphthyl, tetrahydrocarbolinyl, tetrahydroisoxazolopyridinyl, thiazolidinyl and thiomorpholinyl.

Within the scope of this invention, the term "aryl" denotes aromatic hydrocarbons having up to 14 ring members, inter alia phenyls and naphthyls. Each aryl radical can be unsubstituted or mono- or poly-substituted, it being possible for the aryl substituents to be identical or different and to be in any desired and possible position of the aryl. The aryl can be bonded to the general structure of higher order via any desired and possible ring member of the aryl radical. The aryl radicals can also be fused with further saturated, (partially) unsaturated, (hetero)cyclic, aromatic or heteroaromatic ring systems, that is to say with cycloalkyl, heterocyclyl, aryl or heteroaryl, which can themselves be unsubstituted or mono- or poly-substituted. Examples of fused aryl radicals are benzodioxolanyl and benzodioxanyl. Aryl is preferably selected from the group containing phenyl, 1-naphthyl and 2-naphthyl, each of which can be unsubstituted or mono- or poly-substituted. A particularly preferred aryl is phenyl, unsubstituted or mono- or poly-substituted.

The term "heteroaryl" denotes a 5- or 6-membered cyclic aromatic radical which contains at least 1 heteroatom, optionally also 2, 3, 4 or 5 heteroatoms, wherein the heteroatoms are in each case selected independently of one another from the group S, N and O and the heteroaryl radical can be unsubstituted or mono- or poly-substituted; in the case of substitution on the heteroaryl, the substituents can be identical or different and can be in any desired and possible position of the heteroaryl. Bonding to the general structure of higher order can take place via any desired and possible ring member of the heteroaryl radical. The heteroaryl can also be part of a bi- or poly-cyclic system having up to 14 ring members, wherein the ring system can be formed with further saturated, (partially) unsaturated, (hetero)cyclic or aromatic or heteroaromatic rings, that is to say with cycloalkyl, heterocyclyl, aryl or heteroaryl, which can themselves be unsubstituted or mono- or poly-substituted. It is preferred for the heteroaryl radical to be selected from the group comprising benzofuranyl, benzoimidazolyl, benzothienyl, benzothiadiazolyl, benzothiazolyl, benzotriazolyl, benzooxazolyl, benzooxadiazolyl, quinazolinyl, quinoxalinyl, carbazolyl, quinolinyl, dibenzofuranyl, dibenzothienyl, furyl (furanyl), imidazolyl, imidazothiazolyl, indazolyl, indolizinyl, indolyl, isoquinolinyl, isoxazolyl, isothiazolyl, indolyl, naphthyridinyl, oxazolyl, oxadiazolyl, phenazinyl, phenolthiazinyl, phthalazinyl, pyrazolyl, pyridyl (2-pyridyl, 3-pyridyl, 4-pyridyl), pyrrolyl, pyridazinyl, pyrimidinyl, pyrazinyl, purinyl, phenazinyl, thienyl (thiophenyl), triazolyl, tetrazolyl, thiazolyl, thiadiazolyl and triazinyl. Furyl, pyridyl and thienyl are particularly preferred.

Within the scope of the invention, the expressions "$C_{1-4}$-alkyl- or $C_{1-8}$-alkyl-bridged aryl, heteroaryl, heterocyclyl or cycloalkyl" mean that $C_{1-4}$-alkyl or $C_{1-8}$-alkyl and aryl or heteroaryl or heterocyclyl or cycloalkyl have the meanings defined above and the aryl or heteroaryl or heterocyclyl or cycloalkyl radical is bonded to the general structure of higher order via a $C_{1-4}$-alkyl or $C_{1-8}$-alkyl group. The alkyl chain can in all cases be saturated or unsaturated, branched or unbranched, unsubstituted or mono- or poly-substituted. $C_{1-4}$-Alkyl or $C_{1-8}$-alkyl is preferably selected from the group comprising —$CH_2$—, —$CH_2CH_2$—, —$CH(CH_3)$—, —$CH_2CH_2CH_2$—, —$CH(CH_3)$—$CH_2$—, —$CH(CH_2CH_3)$—, —$CH_2$—$(CH_2)_2$—$CH_2$—, —$CH(CH_3)$—$CH_2$—$CH_2$—, —$CH_2$—$CH(CH_3)$—$CH_2$—, —$CH(CH_3)$—$CH(CH_3)$—, —$CH(CH_2CH_3)$—$CH_2$—, —$C(CH_3)_2$—$CH_2$—, —$CH(CH_2CH_2CH_3)$—, —$C(CH_3)(CH_2CH_3)$—, —$CH_2$—$(CH_2)_3$—$CH_2$—, —$CH(CH_3)$—$CH_2$—$CH_2$—$CH_2$—, —$CH_2$—$CH(CH_3)$—$CH_2$—$CH_2$—, —$CH(CH_3)$—

CH₂—CH(CH₃)—, —CH(CH₃)—CH(CH₃)—CH₂—, —C(CH₃)₂—CH₂—CH₂—, —CH₂—C(CH₃)₂—CH₂—, —CH(CH₂CH₃)—CH₂—CH₂—, —CH₂—CH(CH₂CH₃)—CH₂—, —C(CH₃)₂—CH(CH₃)—, —CH(CH₂CH₃)—CH(CH₃)—, —C(CH₃)(CH₂CH₃)—CH₂—, —CH(CH₂CH₂CH₃)—CH₂—, —C(CH₂CH₂CH₃)—CH₂—, —CH(CH₂CH₂CH₂CH₃)—, —C(CH₃)(CH₂CH₂CH₃)—, —C(CH₂CH₃)₂—, —CH₂—(CH₂)₄—CH₂—, —CH=CH—, —CH=CH—CH₂—, —C(CH₃)=CH₂—, —CH=CH—CH₂—CH₂—, —CH₂—CH=CH—CH₂—, —CH=CH—CH=CH—, —C(CH₃)=CH—CH₂—, —CH=C(CH₃)—CH₂—, —C(CH₃)=C(CH₃)—, —C(CH₂CH₃)=CH—, —CH=CH—CH₂—CH₂—CH₂—, —CH₂—CH=CH—CH₂—CH₂—, —CH=CH—CH—CH₂—CH₂—, —CH=CH₂—CH=CH—CH₂—, —C≡C—, —C≡C—CH₂—, —C≡C—CH₂—CH₂—, —C≡C—CH(CH₃)—, —CH₂—C≡C—CH₂—, —C≡C—C≡C—, —C≡C—C(CH₃)₂—, —C≡C—CH₂—CH₂—CH₂—, —CH₂—C≡C—CH₂—CH₂—, —C≡C—C≡C—CH₂— and —C≡C—CH₂—C≡C—.

Within the scope of the invention, the expressions "C₂₋₈-heteroalkyl-bridged aryl, heteroaryl, heterocyclyl or cycloalkyl" mean that C₂₋₈-heteroalkyl and aryl or heteroaryl or heterocyclyl or cycloalkyl have the meanings defined above and the aryl or heteroaryl or heterocyclyl or cycloalkyl radical is bonded to the general structure of higher order via a C₂₋₈-heteroalkyl group. The heteroalkyl chain can in all cases be saturated or unsaturated, branched or unbranched, unsubstituted or mono- or poly-substituted. If a terminal carbon atom of the C₂₋₈-heteroalkyl group has been replaced by a heteroatom or heteroatom group, then the bonding of a heteroaryl or heterocyclyl to the heteroatom or heteroatom group of the C₂₋₈-heteroalkyl always takes place via a carbon atom of the heteroaryl or heterocyclyl. The terminal carbon atom is understood as being the carbon atom within the C₂₋₈-heteroalkyl that is furthest in the chain from the general structure of higher order. If the terminal carbon atom of a C₂₋₈-heteroalkyl has been replaced, for example, by an N(CH₃) group, that group is located within the C₂₋₈-heteroalkyl furthest from the general structure of higher order and is bonded to the aryl or heteroaryl or heterocyclyl or cycloalkyl radical. C₂₋₈-Heteroalkyl is preferably selected from the group comprising —CH₂—NH—, —CH₂—N(CH₃)—, —CH₂—O—, —CH₂—CH₂—NH—, —CH₂—CH₂—N(CH₃)—, —CH₂—CH₂—O—, —CH₂—CH₂—NH—, —CH₂—CH₂—CH₂—N(CH₃)—, —CH₂—CH₂—O—, —CH₂—O—CH₂—, —CH₂—CH₂—O—, —CH₂—CH₂—O—CH₂—, —CH₂—CH₂—O—CH₂—CH₂—, —CH₂—CH₂—O—CH₂—CH₂—O—CH₂—, —CH=CH—O—CH₂—, —CH=CH—O—CH₂—CH₂—, =CH—O—CH₂—, =CH—O—CH₂—CH₂—, =CH—CH₂—O—CH₂—CH₂—, =CH—CH₂—O—CH₂—, —CH₂—NH—CH₂—, —CH₂—CH₂—NH—CH₂—, —CH₂—CH₂—NH—CH₂—CH₂—, —CH₂—CH₂—NH—CH₂—, —CH=CH—NH—CH₂—, —CH=CH—NH—CH₂—CH₂—, —CH=CH—N(CH₃)—CH₂—, =CH—NH—CH₂—, =CH—NH—CH₂—CH₂—, =CH—CH₂—NH—CH₂—CH₂—, =CH—CH₂—NH—CH₂—, —CH₂—N(CH₃)—CH₂—, —CH₂—CH₂—N(CH₃)—CH₂—, —CH₂—CH₂—N(CH₃)—CH₂—CH₂—, —CH₂—CH₂—N(CH₃)—CH₂—N(CH₃)—CH₂—, —CH₂—CH₂—NH—CH₂—CH₂—O—CH₂—, —CH₂—CH₂—O—CH₂—CH₂—NH—CH₂—, —CH₂—N(CH₃)—CH₂—CH₂—O—CH₂—, —CH₂—CH₂—O—CH₂—CH₂—N(CH₃)—CH₂—, —CH₂—CH₂—N(CH₃)—CH₂—, —CH₂—NH—CH₂—, —CH₂—O—CH₂—NH—CH₂—, —CH₂—N(CH₃)—CH₂—O—CH₂—, —CH₂—O—CH₂—N(CH₃)—CH₂—, —CH=CH—N(CH₃)—CH₂—, =CH—N(CH₃)—CH₂—, =CH—N(CH₃)—CH₂—CH₂—, =CH—CH₂—N(CH₃)—CH₂—CH₂— and =CH—CH₂—N(CH₃)—CH₂—.

In connection with "alkyl", "heteroalkyl", "heterocyclyl" and "cycloalkyl", the expression "mono- or poly-substituted" is understood as meaning within the scope of this invention the substitution of one or more hydrogen atoms one or more times, for example two, three or four times, in each case independently of one another, by substituents selected from the group comprising F; Cl; Br; I; NO₂; CF₃; CN; =O; C₁₋₈-alkyl; C₂₋₈-heteroalkyl; aryl; heteroaryl; C₃₋₁₀-cycloalkyl; heterocyclyl; C₁₋₈-alkyl- or C₂₋₈-heteroalkyl-bridged aryl, heteroaryl, C₃₋₁₀-cycloalkyl or heterocyclyl; CHO; C(=O)C₁₋₈-alkyl; C(=O)aryl; C(=O)heteroaryl; CO₂H; C(=O)O—C₁₋₈-alkyl; C(=O)O-aryl; C(=O)O-heteroaryl; CONH₂; C(=O)NH—C₁₋₈-alkyl; C(=O)N(C₁₋₈-alkyl)₂; C(=O)NH-aryl; C(=O)N(aryl)₂; C(=O)NH-heteroaryl; C(=O)N(heteroaryl)₂; C(=O)N(C₁₋₈-alkyl)(aryl); C(=O)N(C₁₋₈-alkyl)(heteroaryl); C(=O)N(heteroaryl)(aryl); OH; O—C₁₋₈-alkyl; OCF₃; O—(C₁₋₈-alkyl)-OH; O—(C₁₋₈-alkyl)-O—C₁₋₈-alkyl; O-benzyl; O-aryl; O-heteroaryl; O—C(=O)C₁₋₈-alkyl; O—C(=O)aryl; O—C(=O)heteroaryl; NH₂; NH—C₁₋₈-alkyl; N(C₁₋₈-alkyl)₂; NH—C(=O)C₁₋₈-alkyl; N(C₁₋₈-alkyl)-C(=O)C₁₋₈-alkyl; N(C(=O)C₁₋₈-alkyl)₂; NH—C(=O)-aryl; NH—C(=O)-heteroaryl; SH; S—C₁₋₈-alkyl; SCF₃; S-benzyl; S-aryl; S-heteroaryl; S(=O)₂C₁₋₈-alkyl; S(=O)₂aryl; S(=O)₂heteroaryl; S(=O)₂OH; S(=O)₂O—C₁₋₈-alkyl; S(=O)₂O-aryl; S(=O)₂O-heteroaryl; S(=O)₂—NH—C₁₋₈-alkyl; S(=O)₂—NH-aryl; and S(=O)₂—NH—C₁₋₈-heteroaryl; wherein polysubstituted radicals are to be understood as being radicals that are substituted several times, for example two, three or four times, either on different atoms or on the same atom, for example three times on the same carbon atom, as in the case of CF₃ or CH₂CF₃, or at different places, as in the case of CH(OH)—CH=CH—CHCl₂. A substituent can itself optionally be mono- or poly-substituted. Polysubstitution can take place with the same or with different substituents.

Preferred "alkyl", "heteroalkyl", "heterocyclyl" and "cycloalkyl" substituents are selected from the group comprising F; Cl; Br; I; NO₂; CH₂CF₃; CF₃; CN; C₁₋₈-alkyl; C₂₋₈-heteroalkyl; phenyl; naphthyl; pyridyl; thienyl; furyl; C₃₋₁₀-cycloalkyl; heterocyclyl; C₁₋₈-alkyl- or C₂₋₈-heteroalkyl-bridged phenyl, naphthyl, pyridyl, thienyl, furyl, C₃₋₁₀-cycloalkyl or heterocyclyl; CHO; C(=O)C₁₋₈-alkyl; CO₂H; C(=O)O—C₁₋₈-alkyl; CONH₂; C(=O)NH—C₁₋₈-alkyl; C(=O)N(C₁₋₈-alkyl)₂; OH; =O; O—C₁₋₈-alkyl; OCF₃; O—(C₁₋₈-alkyl)-OH; O—(C₁₋₈-alkyl)-O—C₁₋₈-alkyl; O-benzyl; O-phenyl; O-heteroaryl; O—C(=O)C₁₋₈-alkyl; NH₂; NH—C₁₋₈-alkyl; N(C₁₋₈-alkyl)₂; NH—C(=O)C₁₋₈-alkyl; N(C₁₋₈-alkyl)-C(=O)C₁₋₈-alkyl; N(C(=O)C₁₋₈-alkyl)₂; SH; S—C₁₋₈-alkyl; SCF₃; S-benzyl; S-phenyl; S-heteroaryl; S(=O)₂C₁₋₈-alkyl; S(=O)₂OH; S(=O)₂O—C₁₋₈-alkyl; S(=O)₂—NH—C₁₋₈-alkyl.

In connection with "aryl" and "heteroaryl", "mono- or poly-substituted" is understood within the scope of this invention as meaning the substitution of one or more hydrogen atoms of the ring system one or more times, for example two, three or four times, in each case independently of one another, by substituents selected from the group comprising F; Cl; Br; I; NO₂; CF₃; CN; C₁₋₈-alkyl; C₂₋₈-heteroalkyl; aryl; heteroaryl; C₃₋₁₀-cycloalkyl; heterocyclyl; C₁₋₈-alkyl- or C₂₋₈-heteroalkyl-bridged aryl, heteroaryl, C₃₋₁₀-cycloalkyl or heterocyclyl; CHO; C(=O)C₁₋₈-alkyl; C(=O)aryl; C(=O)heteroaryl; CO₂H; C(=O)O—C₁₋₈-alkyl;

C(=O)O-aryl; C(=O)O-heteroaryl; $CONH_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; $OCF_3$; O—($C_{1-8}$-alkyl)-OH; O—($C_{1-8}$-alkyl)-O—$C_{1-8}$-alkyl; O-benzyl; O-aryl; O-heteroaryl; O—C(=O)$C_{1-8}$-alkyl; O—C(=O)aryl; O—C(=O)heteroaryl; $NH_2$; NH—$C_{1-8}$-alkyl; N($C_{1-8}$-alkyl)$_2$; NH—C(=O)$C_{1-8}$-alkyl; N($C_{1-8}$-alkyl)-C(=O)$C_{1-8}$-alkyl; N(C(=O)$C_{1-8}$-alkyl)$_2$; NH—C(=O)-aryl; NH—C(=O)-heteroaryl; SH; $SCF_3$; S-benzyl; S-aryl; S-heteroaryl; S(=O)$_2C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; S(=O)$_2$—NH—$C_{1-8}$-heteroaryl; on one atom or optionally on different atoms, wherein a substituent can itself optionally be mono- or poly-substituted. Polysubstitution is carried out with the same or with different substituents.

Preferred "aryl" and "heteroaryl" substituents are F; Cl; Br; I; $NO_2$; $CH_2CF_3$; $CF_3$; CN; $C_{1-8}$-alkyl; $C_{2-8}$-heteroalkyl; phenyl; naphthyl; pyridyl; thienyl; furyl; $C_{3-10}$-cycloalkyl; heterocyclyl; $C_{1-8}$-alkyl- or $C_{2-8}$-heteroalkyl-bridged phenyl, naphthyl, pyridyl, thienyl, furyl, $C_{3-10}$-cycloalkyl or heterocyclyl; CHO; C(=O)$C_{1-8}$-alkyl; $CO_2H$; C(=O)O—$C_{1-8}$-alkyl; $CONH_2$; C(=O)NH—$C_{1-8}$-alkyl; C(=O)N($C_{1-8}$-alkyl)$_2$; OH; O—$C_{1-8}$-alkyl; $OCF_3$; O—($C_{1-8}$-alkyl)-OH; O—($C_{1-8}$-alkyl)-O—$C_{1-8}$-alkyl; O-benzyl; O-phenyl; O-heteroaryl; O—C(=O)$C_{1-8}$-alkyl; $NH_2$; NH—$C_{1-8}$-alkyl; N($C_{1-8}$-alkyl)$_2$; NH—C(=O)$C_{1-8}$-alkyl; N($C_{1-8}$-alkyl)-C(=O)$C_{1-8}$-alkyl; N(C(=O)$C_{1-8}$-alkyl)$_2$; SH; S—$C_{1-8}$-alkyl; $SCF_3$; S-benzyl; S-phenyl; S-heteroaryl; S(=O)$_2C_{1-8}$-alkyl; S(=O)$_2$OH; S(=O)$_2$O—$C_{1-8}$-alkyl; S(=O)$_2$—NH—$C_{1-8}$-alkyl.

The compounds according to the invention are defined by substituents, for example by $R^1$, $R^2$ and $R^3$ (1st generation substituents), which are themselves optionally substituted (2nd generation substituents). Depending on the definition, these substituents of the substituents can in turn themselves be substituted (3rd generation substituents). If, for example, $R^1$=aryl (1st generation substituent), aryl can itself be substituted, for example by $C_{1-8}$-alkyl (2nd generation substituent). This yields the functional group aryl-$C_{1-8}$-alkyl. $C_{1-8}$-Alkyl can then in turn itself be substituted, for example by Cl (3rd generation substituent). Overall, this then yields the functional group aryl-$C_{1-8}$-alkyl-Cl.

In a preferred embodiment, however, the 3rd generation substituents cannot themselves be substituted, that is to say there are no 4th generation substituents.

In another preferred embodiment, the 2nd generation substituents cannot themselves be substituted, that is to say there are not even any 3rd generation substituents. In other words, in this embodiment, for example in the case of the general formula (1), the functional groups for $R^1$ to $R^{13}$ can in each case optionally be substituted, but the substituents in each case cannot themselves be substituted.

In some cases, the compounds according to the invention are defined by substituents which are or carry an aryl or heteroaryl radical, in each case unsubstituted or mono- or poly-substituted, or which, together with the carbon atom(s) or heteroatom(s) joining them as ring member(s), form a ring, for example an aryl or heteroaryl, in each case unsubstituted or mono- or poly-substituted. Both these aryl or heteroaryl radicals and the aromatic ring systems so formed can optionally be fused with $C_{3-10}$-cycloalkyl or heterocyclyl, in each case saturated or unsaturated, that is to say with a $C_{3-10}$-cycloalkyl such as cyclopentyl or with a heterocyclyl such as morpholinyl, it being possible for the $C_{3-10}$-cycloalkyl or heterocyclyl radicals so fused to be unsubstituted or mono- or poly-substituted.

In some cases, the compounds according to the invention are defined by substituents which are or carry a $C_{3-10}$-cycloalkyl or heterocyclyl radical, in each case unsubstituted or mono- or poly-substituted, or which, together with the carbon atom(s) or heteroatom(s) joining them as ring member(s), form a ring, for example a $C_{3-10}$-cycloalkyl or heterocyclyl, in each case unsubstituted or mono- or poly-substituted. Both these $C_{3-10}$-cycloalkyl or heterocyclyl radicals and the aliphatic ring systems formed can optionally be fused with aryl or heteroaryl, that is to say with an aryl such as phenyl or with a heteroaryl such as pyridyl, it being possible for the aryl or heteroaryl radicals so fused to be unsubstituted or mono- or poly-substituted.

The expression "salt formed with a physiologically acceptable acid" is understood within the scope of this invention as meaning salts of the active ingredient in question with inorganic or organic acids that are physiologically acceptable in particular when used in humans and/or mammals. The hydrochloride is particularly preferred. Examples of physiologically acceptable acids are: hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, saccharinic acid, monomethylsebacic acid, 5-oxo-proline, hexane-1-sulfonic acid, nicotinic acid, 2-, 3- or 4-aminobenzoic acid, 2,4,6-trimethyl-benzoic acid, α-liponic acid, acetylglycine, hippuric acid, phosphoric acid and/or aspartic acid. Citric acid and hydrochloric acid are particularly preferred.

Physiologically acceptable salts with cations or bases are salts of the compound in question—in the form of the anion with at least one, preferably inorganic cation—that are physiologically acceptable—in particular when used in humans and/or mammals. Particular preference is given to the salts of the alkali and alkaline earth metals but also to ammonium salts, but in particular to (mono-) or (di-)sodium, (mono-) or (di-)potassium, magnesium or calcium salts.

The first aspect of the present invention relates to a compound according the general formula (I) for the treatment and/or the prophylaxis of disorders and/or diseases which are mediated, at least in part, by TSPO (translocator protein 18 kDa).

Hence, the compounds according to the present invention are useful for the treatment and/or the prophylaxis of disorders and/or diseases which are mediated, at least in part, by TSPO activity.

Disorders and/or diseases, which are mediated, at least in part, by TSPO activity, include
  neurological and neurodegenerative disorders,
  psychiatric disorders,
  brain tumours,
  immunological disorders
and inflammatory diseases.

Neurological and Neurodegenerative Disorders Include
  Ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia.

Psychiatric Disorders Include
  anxiety disorders, particularily panic disorders, post traumatic stress disorder, panic and adult separation disorder, social anxiety, major depression with adult separation anxiety disorder and bipolar disorder with adult separation anxiety disorder, dysthymia, angina pectoris, suicidality and schizophrenia.

Immunological Disorders and Inflammatory Diseases Include neuroinflammation and arthritis, encephalomyelitis and irritable bowel syndrome.

Another embodiment of the present invention therefore relates to a compound according to general formula (I) for the treatment and/or the prophylaxis of disorders and/or diseases, wherein the disorder and/or the disease is selected from the group consisting of
(i) neurological and neurodegenerative disorders, including
Ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia;
(ii) psychiatric disorders, including
anxiety disorders, particularily panic disorders, post traumatic stress disorder, panic and adult separation disorder, social anxiety, major depression with adult separation anxiety disorder and bipolar disorder with adult separation anxiety disorder, dysthymia, angina pectoris, suicidality and schizophrenia;
(iii) brain tumours;
(iv) immunological disorders and inflammatory diseases, including
neuroinflammation and arthritis, encephalomyelitis and irritable bowel syndrome.

A preferred embodiment of the present invention relates to a compound according to general formula (I) for the treatment and/or the prophylaxis of
(i) neurological and neurodegenerative disorders, including
ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia;
(ii) psychiatric disorders, including
anxiety disorders, particularly panic disorders, post traumatic stress disorder, panic and adult separation disorder, social anxiety, major depression with adult separation anxiety disorder and bipolar disorder with adult separation anxiety disorder, dysthymia, angina pectoris, suicidality and schizophrenia;
(iii) brain tumours;
(iv) immunological disorders and inflammatory diseases, including
neuroinflammation and arthritis, encephalomyelitis and irritable bowel syndrome.

Another preferred embodiment of the present invention relates to a compound according to general formula (I) for the treatment and/or the prophylaxis of neurological and neurodegenerative disorders,
including ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia.

Another preferred embodiment of the present invention relates to a compound according to general formula (I) for the treatment and/or the prophylaxis of psychiatric disorders, including anxiety disorders, particularily panic disorders, post traumatic stress disorder, panic and adult separation disorder, social anxiety, major depression with adult separation anxiety disorder and bipolar disorder with adult separation anxiety disorder, dysthymia, angina pectoris, suicidality and schizophrenia.

Yet another preferred embodiment of the present invention relates to a compound according to general formula (I) for the treatment and/or the prophylaxis of brain tumours.

Yet another preferred embodiment of the present invention relates to a compound according to general formula (I) for the treatment and/or the prophylaxis of immunological disorders and inflammatory diseases,
including neuroinflammation and arthritis, encephalomyelitis and irritable bowel syndrome.

One embodiment of the present invention relates to a compound of general formula (I), wherein the compound is selected from a compound according to general formula (1-I).

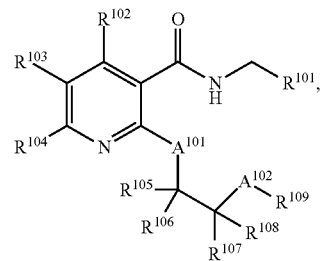

(1-I)

wherein $A^{101}$ represents $CR^{110}R^{111}$ or S;

$A^{102}$ represents $CR^{112}R^{113}$, $C(=O)$, O, S, $S(=O)$ or $S(=O)_2$;

$R^{101}$ represents $C_{1-10}$-alkyl or $C_{2-10}$-heteroalkyl, in each case saturated or unsaturated, branched or unbranched, unsubstituted or mono- or poly-substituted; $C_{3-10}$-cycloalkyl or heterocyclyl, in each case saturated or unsaturated, unsubstituted or mono- or poly-substituted; aryl or heteroaryl, in each case unsubstituted or mono- or poly-substituted; $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted, wherein the alkyl or heteroalkyl chain can in each case be branched or unbranched, saturated or unsaturated, unsubstituted or mono- or poly-substituted; or $C_{1-8}$-alkyl- or $C_{2-8}$-heteroalkyl-bridged aryl or heteroaryl, in each case unsubstituted or mono- or poly-substituted, wherein the alkyl or heteroalkyl chain can in each case be branched or unbranched, saturated or unsaturated, unsubstituted or mono- or poly-substituted;

$R^{102}$, $R^{103}$ and $R^{104}$ each independently of the others represents H; F; Cl; Br; I; $NO_2$; $CF_3$; CN; OH; $OCF_3$; SH; $SCF_3$; methyl; $CH_2$—O-methyl; $CH_2$—OH; $C_{2-6}$-alkyl, O—$C_{1-6}$-alkyl, S—$C_{1-6}$-alkyl, in each case saturated or unsaturated, branched or unbranched, unsubstituted or mono- or poly-substituted; $C_{3-7}$-cycloalkyl, saturated or unsaturated, branched or unbranched, unsubstituted or mono- or poly-substituted; $NR^{1a}R^{1b}$, wherein $R^{1a}$ and $R^{1b}$ each independently of the other represents H or $C_{1-4}$-alkyl, saturated or unsaturated, branched or unbranched, unsubstituted or mono- or poly-substituted, or $R^{1a}$ and $R^{1b}$, together with the nitrogen atom joining them, form a heterocyclyl, saturated or unsaturated, branched or unbranched, unsubstituted or mono- or poly-substituted;

$R^{105}$, $R^{106}$, $R^{107}$, $R^{108}$, $R^{109}$, $R^{111}$, $R^{112}$ and $R^{113}$ each independently of the others represents H; F; Cl; Br; I; $NO_2$; $CF_3$; CN; OH; $OCF_3$; SH; $SCF_3$; $C_{1-10}$-alkyl, $C_{2-10}$-heteroalkyl, O—$C_{1-10}$-alkyl or S—$C_{1-10}$-alkyl, in each case saturated or unsaturated, branched or unbranched, unsubstituted or mono- or poly-substituted; $C_{3-10}$-cycloalkyl, saturated or unsaturated, branched or unbranched, unsubstituted or mono- or poly-substituted;

with the proviso that when $R^{105}$, $R^{106}$, $R^{107}$ and $R^{108}$ each denotes H and $A^1$ represents S, $A^2$ may not denote S, S(=O) or $S(=O)_2$;

or $R^{105}$ and $R^{106}$ or $R^{107}$ and $R^{108}$ or $R^{110}$ and $R^{111}$ or $R^{112}$ and $R^{113}$ or $R^{105}$ and $R^{111}$ or $R^{105}$ and $R^{107}$ or $R^{105}$ and $R^{113}$ or $R^{107}$ and $R^{113}$ or $R^{107}$ and $R^{111}$ or $R^{111}$ and $R^{113}$, together with the carbon atom(s) joining them, form a $C_{3-8}$-cycloalkyl or a heterocyclyl having from three to eight ring members, in each case saturated or unsaturated, unsubstituted or mono- or poly-substituted; wherein the remaining substituents $R^{105}$, $R^{106}$, $R^{107}$, $R^{108}$, $R^{110}$, $R^{111}$, $R^{112}$ and $R^{113}$ in each case have the meaning given above;

$R^{109}$ represents $C_{3-10}$-cycloalkyl or heterocyclyl, in each case saturated or unsaturated, unsubstituted or mono- or poly-substituted; aryl or heteroaryl, in each case unsubstituted or mono- or poly-substituted; or represents $CR^{1c}R^{1d}$, wherein $R^{1c}$ and $R^{1d}$ each independently of the other denotes $C_{1-4}$-alkyl, saturated or unsaturated, branched or unbranched, unsubstituted or mono- or poly-substituted;

with the proviso that when $A^{102}$ represents O or S and $R^{109}$ represents heterocyclyl, saturated or unsaturated, unsubstituted or mono- or poly-substituted; or heteroaryl, unsubstituted or mono- or poly-substituted, the bonding of the heteroaryl or heterocyclyl takes place via a carbon atom of the heteroaryl or heterocyclyl;

wherein "alkyl substituted", "heteroalkyl substituted", "heterocyclyl substituted" and "cycloalkyl substituted" denote the substitution of one or more hydrogen atoms, in each case independently of one another, by F; Cl; Br; I; $NO_2$; $CF_3$; CN; =O; $C_{1-8}$-alkyl; $C_{2-8}$-heteroalkyl; aryl; heteroaryl; $C_{3-10}$-cycloalkyl; heterocyclyl; $C_{1-8}$-alkyl- or $C_{2-8}$-heteroalkyl-bridged aryl, heteroaryl, $C_{3-10}$-cycloalkyl or heterocyclyl; CHO; C(=O)$C_{1-8}$-alkyl; C(=O)aryl; C(=O)heteroaryl; $CO_2H$; C(=O)O—$C_{1-8}$-alkyl; C(=O)O-aryl; C(=O)O-heteroaryl; $CONH_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; $OCF_3$; O—($C_{1-8}$-alkyl)-OH; O—($C_{1-8}$-alkyl)-O—$C_{1-8}$-alkyl; O-benzyl; O-aryl; O-heteroaryl; O—C(=O)$C_{1-8}$-alkyl; O—C(=O)aryl; O—C(=O)heteroaryl; $NH_2$; NH—$C_{1-8}$-alkyl; N($C_{1-8}$-alkyl)$_2$; NH—C(=O)$C_{1-8}$-alkyl; N($C_{1-8}$-alkyl)-C(=O)$C_{1-8}$-alkyl; N(C(=O)$C_{1-8}$-alkyl)$_2$; NH—C(=O)-aryl; NH—C(=O)-heteroaryl; SH; S—$C_{1-8}$-alkyl; $SCF_3$; S-benzyl; S-aryl; S-heteroaryl; S(=O)$_2C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; and S(=O)$_2$—NH—$C_{1-8}$-heteroaryl;

wherein "aryl substituted" and "heteroaryl substituted" denote the substitution of one or more hydrogen atoms, in each case independently of one another, by F; Cl; Br; I; $NO_2$; $CF_3$; CN; $C_{1-8}$-alkyl; $C_{2-8}$-heteroalkyl; aryl; heteroaryl; $C_{3-10}$-cycloalkyl; heterocyclyl; $C_{1-8}$-alkyl- or $C_{2-8}$-heteroalkyl-bridged aryl, heteroaryl, $C_{3-10}$-cycloalkyl or heterocyclyl; CHO; C(=O)$C_{1-8}$-alkyl; C(=O)aryl; C(=O)heteroaryl; $CO_2H$; C(=O)O—$C_{1-8}$-alkyl; C(=O)O-aryl; C(=O)O-heteroaryl; $CONH_2$; C(=O)NH—$C_{1-8}$-alkyl; C(=O)N($C_{1-8}$-alkyl)$_2$; C(=O)NH-aryl; C(=O)N(aryl)$_2$; C(=O)NH-heteroaryl; C(=O)N(heteroaryl)$_2$; C(=O)N($C_{1-8}$-alkyl)(aryl); C(=O)N($C_{1-8}$-alkyl)(heteroaryl); C(=O)N(heteroaryl)(aryl); OH; O—$C_{1-8}$-alkyl; $OCF_3$; O—($C_{1-8}$-alkyl)-OH; O—($C_{1-8}$-alkyl)-O—$C_{1-8}$-alkyl; O-benzyl; O-aryl; O-heteroaryl; O—C(=O)$C_{1-8}$-alkyl; O—C(=O)aryl; O—C(=O)heteroaryl; $NH_2$; NH—$C_{1-8}$-alkyl; N($C_{1-8}$-alkyl)$_2$; NH—C(=O)$C_{1-8}$-alkyl; N($C_{1-8}$-alkyl)-C(=O)$C_{1-8}$-alkyl; N(C(=O)$C_{1-8}$-alkyl)$_2$; NH—C(=O)-aryl; NH—C(=O)-heteroaryl; SH; S—$C_{1-8}$-alkyl; $SCF_3$; S-benzyl; S-aryl; S-heteroaryl; S(=O)$_2C_{1-8}$-alkyl; S(=O)$_2$aryl; S(=O)$_2$heteroaryl; S(=O)$_2$OH; S(=O)$_2$O—$C_{1-8}$-alkyl; S(=O)$_2$O-aryl; S(=O)$_2$O-heteroaryl; S(=O)$_2$—NH—$C_{1-8}$-alkyl; S(=O)$_2$—NH-aryl; S(=O)$_2$—NH—$C_{1-8}$-heteroaryl.

The compounds according to general formula (1-I) are known from WO 2010/102809 A1, which is fully included by reference.

In preferred embodiments of the compounds of the general formula (1-I) according to the invention $A^{101}$ represents S and $A^{102}$ represents $CR^{112}R^{113}$, O, S or $S(=O)_2$, preferably $CR^{112}R^{113}$, S or $S(=O)_2$, particular preferably $CR^{112}R^{113}$.

Further preferred embodiments of the compounds of the general formula (1-I) according to the invention have the general formula (1-I-a), (1-I-b), (1-I-c), (1-I-d), (1-I-e) or (1-I-f):

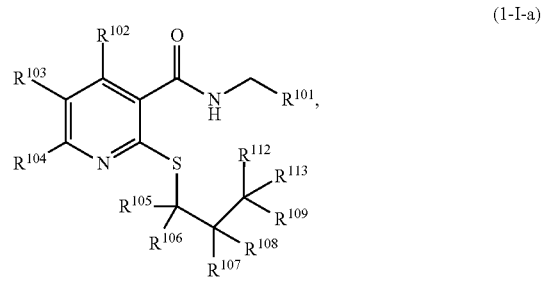

(1-I-a)

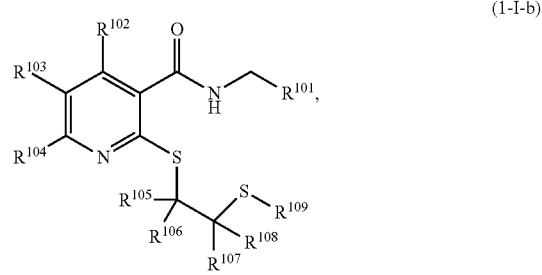

(1-I-b)

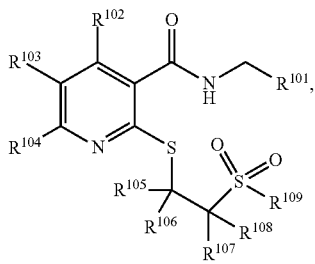

(1-I-c)

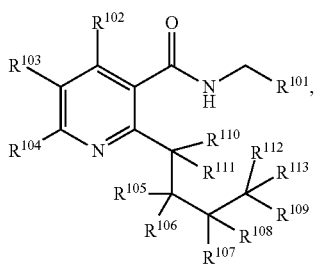

(1-I-d)

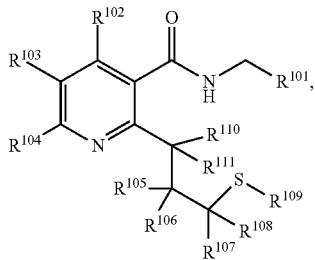

(1-I-e)

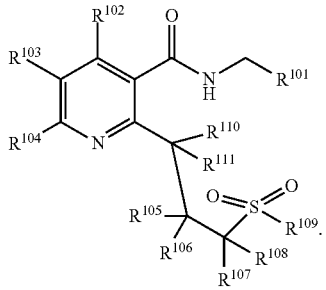

(1-I-f)

Compounds of the general formulae (1-I-a), (1-I-b) and (1-I-c) are most particularly preferred.

Compounds of the general formula (1-1a) are especially preferred.

In a further preferred embodiment the radical $R^{101}$ represents $C_{1-10}$-alkyl or $C_{2-10}$-heteroalkyl, in each case saturated or unsaturated, branched or unbranched, unsubstituted or mono- or poly-substituted by one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$-alkyl, O—$C_{1-8}$-alkyl, S—$C_{1-8}$-alkyl, NH—$C_{1-8}$-alkyl, $N(C_{1-8}$-alkyl$)_2$, $C_{3-10}$-cycloalkyl and heterocyclyl, wherein the above alkyl radicals can in each case be saturated or unsaturated, branched or unbranched, unsubstituted or mono- or poly-substituted by one or more substituents each selected independently of one another from the group consisting of F, Cl, Br, I, O—$C_{1-8}$-alkyl, OH and $OCF_3$, and wherein $C_{3-10}$-cycloalkyl or heterocyclyl can in each case be saturated or unsaturated, unsubstituted or mono- or poly-substituted by one or more substituents each selected independently of one another from the group consisting of F, Cl, Br, I, $C_{1-8}$-alkyl, OH, =O, O—$C_{1-8}$-alkyl, $OCF_3$, $NH_2$, NH—$C_{1-8}$-alkyl and N($C_{1-8}$-alkyl$)_2$;

or $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$;

or aryl or heteroaryl, in each case unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$;

or $C_{1-8}$-alkyl- or $C_{2-8}$-heteroalkyl-bridged $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$;

wherein the alkyl or heteroalkyl chain can in each case be branched or unbranched, saturated or unsaturated, unsubstituted or mono- or poly-substituted by one or more substituents each selected independently of one another from the group consisting of F, Cl, Br, I, $NO_2$, $CF_3$, CN, OH, =O, C(=O)—OH, $OCF_3$, $NH_2$, $S(=O)_2OH$, SH, $SCF_3$, $C_{1-8}$-alkyl, O—$C_{1-8}$-alkyl, S—$C_{1-8}$-alkyl, NH—$C_{1-8}$-alkyl, $N(C_{1-8}$-alkyl$)_2$, $C_{3-10}$-cycloalkyl and heterocyclyl, wherein the above alkyl radicals can in each case be saturated or unsaturated, branched or unbranched, unsubstituted or mono- or poly-substituted by one or more substituents each selected independently of one another from the group consisting of F, Cl, Br, I, O—$C_{1-8}$-alkyl, OH and $OCF_3$, and wherein $C_{3-10}$-cycloalkyl or heterocyclyl can in each case be saturated or unsaturated, unsubstituted or mono- or poly-substituted by one or more substituents each selected independently of one another from the group consisting of F, Cl, Br, I, $C_{1-8}$-alkyl, OH, =O, O—$C_{1-8}$-alkyl, $OCF_3$, $NH_2$, NH—$C_{1-8}$-alkyl and $N(C_{1-8}$-alkyl$)_2$;

or $C_{1-8}$-alkyl- or $C_{2-8}$-heteroalkyl-bridged aryl or heteroaryl, in each case unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$;

wherein the alkyl or heteroalkyl chain can in each case be branched or unbranched, saturated or unsaturated, unsubstituted or mono- or poly-substituted by one or more substituents each selected independently of one another from the group consisting of F, Cl, Br, I, $NO_2$, $CF_3$, CN, OH, =O, C(=O)—OH, $OCF_3$, $NH_2$, $S(=O)_2$ OH, SH, $SCF_3$, $C_{1-8}$-alkyl, O—$C_{1-8}$-alkyl, S—$C_{1-8}$-alkyl, NH—$C_{1-8}$-alkyl, $N(C_{1-8}$-alkyl$)_2$, $C_{3-10}$-cycloalkyl and heterocyclyl, wherein the above alkyl radicals can in each case be saturated or unsaturated, branched or unbranched, unsubstituted or mono- or poly-substituted by one or more substituents each selected independently of one another from the group consisting of F, Cl, Br, I, O—$C_{1-8}$-alkyl, OH and $OCF_3$, and wherein $C_{3-10}$-cycloalkyl or heterocyclyl can in each case be saturated or unsaturated, unsubstituted or mono- or poly-substituted by one or more substituents each selected independently of one another from the group consisting of F, Cl, Br, I, $C_{1-8}$-alkyl, OH, =O, O—$C_{1-8}$-alkyl, $OCF_3$, $NH_2$, NH—$C_{1-8}$-alkyl and $N(C_{1-8}$-alkyl$)_2$.

In a further preferred embodiment the substituent $R^{101}$ represents the following partial structure (1-T1),

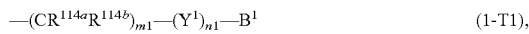

$$—(CR^{114a}R^{114b})_{m1}—(Y^1)_{n1}—B^1 \qquad (1\text{-}T1),$$

wherein $R^{114a}$ and $R^{114b}$ each independently of the other represents H; F; Cl; Br; I; $NO_2$; $CF_3$; CN; OH; $OCF_3$; $NH_2$; $C_{1-4}$-alkyl, O—$C_{1-4}$-alkyl, NH—$C_{1-4}$-alkyl, $N(C_{1-4}$-alkyl$)_2$, in each case saturated or unsaturated, branched or unbranched, unsubstituted or mono- or poly-substituted by one or more substituents each selected independently of one another from the group consisting of F, Cl, Br, I, O—$C_{1-4}$-alkyl, OH and $OCF_3$; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $C_{1-4}$-alkyl, OH, =O, O—$C_{1-4}$-alkyl, $OCF_3$, $NH_2$, NH—$C_{1-4}$-alkyl and $N(C_{1-4}$-alkyl$)_2$;

m1 represents 0, 1, 2 or 3;
$Y^1$ represents O or $NR^{115}$,
wherein $R^{115}$ represents H; $C_{1-4}$-alkyl, saturated or unsaturated, branched or unbranched, unsubstituted or mono- or poly-substituted by one or more substituents each selected independently of one another from the group consisting of F, Cl, Br, I, $C_{1-4}$-alkyl, OH, O—$C_{1-4}$-alkyl, $OCF_3$, $NH_2$, NH—$C_{1-4}$-alkyl and $N(C_{1-4}$-alkyl$)_2$; or represents $C_{3-10}$-cycloalkyl, saturated or unsaturated, unsubstituted or mono- or poly-substituted by one or more substituents each selected independently of one another from the group consisting of F, Cl, Br, I, $C_{1-4}$-alkyl, OH, O—$C_{1-4}$-alkyl, $OCF_3$, $NH_2$, NH—$C_{1-4}$-alkyl and $N(C_{1-4}$-alkyl$)_2$;

n1 represents 0 or 1,
$B^1$ represents $C_{1-8}$-alkyl, saturated or unsaturated, branched or unbranched, unsubstituted or mono- or poly-substituted by one or more substituents each selected independently of one another from the group consisting of F, Cl, Br, I, $NO_2$, CN, OH, =O, O—$C_{1-4}$-alkyl, $OCF_3$, C(=O)—OH, $CF_3$, $NH_2$, $NH(C_{1-4}$-alkyl), $N(C_{1-4}$-alkyl$)_2$, SH, S—$C_{1-4}$-alkyl, $SCF_3$ and $S(=O)_2OH$; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$; aryl or heteroaryl, in each case unsubstituted or mono- or poly-substituted by one or more substituents each selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$, $S(=O)_2OH$, benzyl, phenyl, pyridyl and thienyl, wherein benzyl, phenyl, pyridyl, thienyl can in each case be unsubstituted or mono- or poly-substituted by one or more substituents selected independently of one another from the group consisting of F, Cl, Br, I, $NO_2$, CN, OH, O—$C_{1-8}$-alkyl, $OCF_3$, $C_{1-8}$-alkyl, C(=O)—OH, $CF_3$, $NH_2$, $NH(C_{1-8}$-alkyl), $N(C_{1-8}$-alkyl$)_2$, SH, S—$C_{1-8}$-alkyl, $SCF_3$ and $S(=O)_2OH$.

Preferably,
$R^{114a}$ and $R^{114b}$ each independently of the other represents H; F; Cl; Br; I; $NO_2$; $CF_3$; $CH_2CF_3$; CN; OH; $OCF_3$, $NH_2$; $C_{1-4}$-alkyl, O—$C_{1-4}$-alkyl, O—$C_{1-4}$-alkyl-OH, O—$C_{1-4}$-alkyl-$OCH_3$, NH—$C_{1-4}$-alkyl, $N(C_{1-4}$-alkyl$)_2$, in each case saturated or unsaturated, branched or unbranched, unsubstituted; $C_{3-10}$-cycloalkyl, saturated or unsaturated, unsubstituted or mono- or poly-substituted by one or more substituents each selected independently of one another from the group consisting of F, Cl, Br, I, $C_{1-4}$-alkyl, OH, O—$C_{1-4}$-alkyl;

m1 represents 0, 1, 2 or 3;
$Y^1$ represents O or $NR^{115}$;
wherein $R^{115}$ represents H; $C_{1-4}$-alkyl, saturated or unsaturated, unsubstituted; or
represents $C_{3-10}$-cycloalkyl, saturated or unsaturated, unsubstituted;

n1 represents 0 or 1;
$B^1$ represents $C_{1-8}$-alkyl, saturated or unsaturated, branched or unbranched, unsubstituted or mono- or poly-substituted by one or more substituents each selected independently of one another from the group consisting of F, Cl, Br, I, $NO_2$, CN, OH, O—$C_{1-4}$-alkyl, $OCF_3$, $CF_3$, $NH_2$, NH ($C_{1-4}$-alkyl), $N(C_{1-4}$-alkyl$)_2$, $SCF_3$; $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, $CF_3$, $NH_2$, $NH(C_{1-4}$-alkyl), $N(C_{1-4}$-alkyl$)_2$, $SCF_3$; aryl or heteroaryl, in each case unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl$)_2$, SH, S—$C_{1-4}$-alkyl, $SCF_3$, S(=O)$_2$OH, benzyl, phenyl and pyridyl, wherein benzyl, phenyl or pyridyl are in each case unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl$)_2$, SH, S—$C_{1-4}$-alkyl, $SCF_3$ and S(=O)$_2$OH.

Particularly preferably, $R^{114a}$ and $R^{114b}$ each independently of the other represents H; F; Cl; Br; I; $NO_2$; $CF_3$; CN; methyl; ethyl; n-propyl; isopropyl; cyclopropyl; n-butyl; sec-butyl; tert-butyl; $CH_2CF_3$; OH; O-methyl; O-ethyl; O—$(CH_2)_2$—O—$CH_3$; O—$(CH_2)_2$—OH; $OCF_3$; $NH_2$; NH-methyl; N(methyl)$_2$; NH-ethyl; N(ethyl)$_2$; or N(methyl)(ethyl);
m1 represents 0, 1 or 2;
n1 represents 0; and
$B^1$ represents $C_{1-4}$-alkyl, saturated, branched or unbranched, unsubstituted or mono- or poly-substituted by one or more substituents each selected independently of one another from the group consisting of F, Cl, Br, I, OH, O—$C_{1-4}$-alkyl, $OCF_3$ and $CF_3$; $C_{3-10}$-cycloalkyl, saturated, unsubstituted; phenyl, naphthyl, pyridyl, thienyl, in each case unsubstituted or mono- or di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl$)_2$, SH, S—$C_{1-4}$-alkyl, $SCF_3$, S(=O)$_2$OH.

Most particularly preferably, $R^{114a}$ and $R^{114b}$ each independently of the other represents H; F; Cl; Br; I; methyl; ethyl; n-propyl; isopropyl; n-butyl; sec-butyl; tert-butyl; OH; O-methyl; O-ethyl; O—$(CH_2)_2$—O—$CH_3$; or O—$(CH_2)_2$—OH;
m1 represents 0, 1 or 2;
n1 represents 0; and
$B^1$ represents methyl; ethyl; n-propyl; isopropyl; n-butyl; sec-butyl; tert-butyl; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl, thienyl, in each case unsubstituted or mono-, di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl$)_2$, SH, S—$C_{1-4}$-alkyl, $SCF_3$ and S(=O)$_2$OH.

For n1=0, the partial structure (1-T1) for $R^{101}$ yields the partial structure (1-T1-1):

  (1-T1-1).

In a preferred embodiment for n1=0, $R^{114a}$ and $R^{114b}$ each independently of the other represents H; F; Cl; Br; I; methyl; ethyl; n-propyl; isopropyl; n-butyl; sec-butyl; tert-butyl; OH; O-methyl; O-ethyl; O—$(CH_2)_2$—O—$CH_3$; or O—$(CH_2)_2$—OH.

In a preferred embodiment for m1=0, $B^1$ represents phenyl, pyridyl or thienyl, mono- or di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl$)_2$, SH, S—$C_{1-4}$-alkyl, $SCF_3$, S(=O)$_2$OH.

In a preferred embodiment for m1=1 or 2, $B^1$ represents cyclopropyl; cyclobutyl; cyclopentyl; cyclohexyl; cycloheptyl; adamantyl; bicyclo[2.2.1]heptyl; bicyclo[2.2.2]octyl.

In a preferred embodiment for m1=0, 1 or 2, $B^1$ represents methyl; ethyl; n-propyl; isopropyl; n-butyl; sec-butyl or tert-butyl.

A further particularly preferred embodiment of the compounds of the general formula (I-1) according to the invention has the general formula (I-1-2):

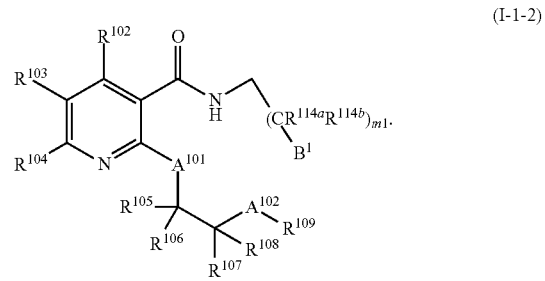

In a further preferred embodiment,
the radicals $R^{102}$, $R^{103}$ and $R^{104}$ each independently of the others represent H; F; Cl; Br; I; $NO_2$; $CF_3$; CN; OH; $OCF_3$; SH; $SCF_3$; methyl; $CH_2$—O-methyl; $CH_2$—OH; $C_{2-6}$-alkyl, O—$C_{1-6}$-alkyl or S—$C_{1-6}$-alkyl, in each case saturated or unsaturated, branched or unbranched, unsubstituted or mono- or poly-substituted by one or more substituents each selected independently of one another from the group consisting of F, Cl, Br, I, OH, =O and O—$C_{1-4}$-alkyl; $C_{3-7}$-cycloalkyl, saturated or unsaturated, branched or unbranched, unsubstituted; $NR^{1a}R^{1b}$,
  wherein $R^{1a}$ and $R^{1b}$ each independently of the other represents H or $C_{1-4}$-alkyl, saturated or unsaturated, branched or unbranched, unsubstituted or mono- or poly-substituted by one or more substituents each selected independently of one another from the group consisting of OH, =O and O—$C_{1-4}$-alkyl,
  or $R^{1a}$ and $R^{1b}$, together with the nitrogen atom joining them, form a heterocyclyl, saturated or unsaturated, unsubstituted or mono- or poly-substituted by $C_{1-4}$-alkyl.

Preferably,
the radicals $R^{102}$, $R^{103}$ and $R^{104}$ each independently of the others represent H; F; Cl; Br; I; $NO_2$; $CF_3$; CN; OH; $OCF_3$; SH; $SCF_3$; methyl; ethyl; n-propyl; isopropyl; butyl; sec-butyl; tert-butyl; $CH_2CF_3$; O-methyl; O-ethyl; O-n-propyl; O-isopropyl; O-butyl; O-sec-butyl; O-tert-butyl; O—$(CH_2)_2$—O-methyl; O—$(CH_2)_2$—OH; O—(C=O)-methyl; O—(C=O)-ethyl; S-methyl; S-ethyl; cyclopropyl; cyclobutyl; $NR^{1a}R^{1b}$,
  wherein $R^{1a}$ and $R^{1b}$ each independently of the other is selected from the group consisting of H, methyl, ethyl, $(CH_2)_2$—O-methyl, $(CH_2)_2$—OH, (C=O)-methyl, (C=O)-ethyl,
  or $R^{1a}$ and $R^{1b}$, together with the nitrogen atom joining them, form a pyrrolidinyl, piperidinyl, 4-methylpiperazinyl or morpholinyl.

Particularly preferably,
the radicals $R^{102}$, $R^{103}$ and $R^{104}$ each independently of the others represent H; F; Cl; Br; I; methyl; ethyl; n-propyl, isopropyl; cyclopropyl; CN; $CF_3$; O-methyl; $OCF_3$; S-methyl; $SCF_3$, pyrrolidinyl, N(methyl)$_2$.

Most particularly preferably, the radicals $R^{102}$, $R^{103}$ and $R^{104}$ each independently of the others represent H; F; Cl; methyl; ethyl; O-methyl; $CF_3$; in particular H.

In a further preferred embodiment, the radicals $R^{105}$, $R^{106}$, $R^{107}$, $R^{108}$, $R^{110}$, $R^{111}$, $R^{112}$ and $R^{113}$ each independently of the others represents H; F; Cl; Br; I; $NO_2$; $CF_3$; CN; OH; $OCF_3$; SH; $SCF_3$; $C_{1-6}$-alkyl; O—$C_{1-6}$-alkyl or S—$C_{1-6}$-alkyl, in each case saturated or unsaturated, branched or unbranched, unsubstituted or mono- or poly-substituted by one or more substituents each selected independently of one another from the group consisting of F, Cl, Br, I, OH and O—$C_{1-4}$-alkyl; $C_{3-7}$-cycloalkyl, saturated or unsaturated, branched or unbranched, unsubstituted or mono- or poly-substituted by one or more substituents each selected independently of one another from the group consisting of F, Cl, Br, I, OH, =O and O—$C_{1-4}$-alkyl;
or $R^{105}$ and $R^{106}$ or $R^{107}$ and $R^{108}$ or $R^{110}$ and $R^{111}$ or $R^{112}$ and $R^{113}$ or $R^{105}$ and $R^{111}$ or $R^{105}$ and $R^{107}$ or $R^{105}$ and $R^{113}$ or $R^{107}$ and $R^{113}$ or $R^{107}$ and $R^{111}$ or $R^{111}$ and $R^{113}$, together with the carbon atom(s) joining them, form a cyclopropyl, cyclobutyl, cyclopentyl, cyclohexyl, pyrrolidinyl or piperidinyl, in each case unsubstituted or mono- or poly-substituted by one or more substituents each selected independently of one another from the group consisting of F, Cl, Br, I, OH, =O and O—$C_{1-4}$-alkyl; wherein the remaining substituents $R^{105}$, $R^{106}$, $R^{107}$, $R^{108}$, $R^{110}$, $R^{111}$, $R^{112}$ and $R^{113}$ in each case have the meaning given above.

Preferably, the radicals $R^{105}$, $R^{106}$, $R^{107}$, $R^{108}$, $R^{110}$, $R^{111}$, $R^{112}$ and $R^{113}$ each independently of the others represents H; F; Cl; Br; I; $NO_2$; $CF_3$; CN; OH; $OCF_3$; SH; $SCF_3$; methyl; ethyl; n-propyl; isopropyl; n-butyl; sec-butyl; tert-butyl; O-methyl; O-ethyl; O—$(CH_2)_2$—O—$CH_3$; O—$(CH_2)_2$—OH; S-methyl; S-ethyl; cyclopropyl; cyclobutyl; cyclopentyl; cyclohexyl;
or $R^{105}$ and $R^{106}$ or $R^{107}$ and $R^{108}$ or $R^{110}$ and $R^{111}$ or $R^{112}$ and $R^{113}$ or $R^{105}$ and $R^{111}$ or $R^{105}$ and $R^{107}$ or $R^{105}$ and $R^{113}$ or $R^{107}$ and $R^{113}$ or $R^{107}$ and $R^{111}$ or $R^{111}$ and $R^{113}$, together with the carbon atom(s) joining them, form a cyclopropyl, cyclobutyl, cyclopentyl or cyclohexyl, in each case unsubstituted; wherein the remaining substituents $R^{105}$ $R^{106}$, $R^{107}$, $R^{108}$, $R^{110}$, $R^{111}$, $R^{112}$ and $R^{113}$ in each case have the meaning given above.

Particularly preferably, the radicals $R^{105}$, $R^{106}$, $R^{107}$, $R^{108}$, $R^{110}$, $R^{111}$, $R^{112}$ and $R^{113}$ each independently of the others represents H; F; Cl; Br; I; CN; $CF_3$; $OCF_3$; $SCF_3$; methyl; ethyl; n-propyl, isopropyl; cyclopropyl; O-methyl; S-methyl;
or $R^{105}$ and $R^{107}$ form a cyclopropyl, cyclobutyl, cyclopentyl or cyclohexyl ring substituted as desired by H, F, Cl, Me, Et, OMe, preferably an unsubstituted cyclopentyl or cyclohexyl ring.

Most particularly preferably, the radicals $R^{105}$, $R^{106}$, $R^{107}$, $R^{108}$, $R^{110}$, $R^{111}$, $R^{112}$ and $R^{113}$ each independently of the others represents F; Cl; H; methyl; ethyl; n-propyl, isopropyl; cyclopropyl; in particular F; H; methyl; or ethyl.

In particular, the radicals $R^{112}$ and $R^{113}$ each independently of the other represents H, F or methyl.

In a further preferred embodiment,
the radical $R^{109}$ represents $C_{3-10}$-cycloalkyl or heterocyclyl, in each case saturated or unsaturated, unsubstituted or mono- or poly-substituted by one or more substituents each selected independently of one another from the group consisting of F, Cl, Br, I, $NO_2$, CN, OH, =O, O—$C_{1-4}$-alkyl, $OCF_3$, $C_{1-4}$-alkyl, $CF_3$, SH, S—$C_{1-4}$-alkyl and $SCF_3$; aryl or heteroaryl, in each case unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, $CF_3$, $NH_2$, $NH(C_{1-4}$-alkyl), $N(C_{1-4}$-alkyl)$_2$, SH, S—$C_{1-4}$-alkyl and $SCF_3$;
or represents $CR^{1c}R^{1d}$,
 wherein $R^{1c}$ and $R^{1d}$ each independently of the other denotes $C_{1-4}$-alkyl, saturated or unsaturated, branched or unbranched, unsubstituted or mono- or poly-substituted by one or more substituents each selected independently of one another from the group consisting of F, Cl, Br, I, OH, O—$C_{1-4}$-alkyl, $CF_3$, $OCF_3$ and $SCF_3$.

Preferably, $R^{109}$ represents $C_{3-7}$-cycloalkyl, saturated or unsaturated, pyrrolidinyl, piperazinyl, 4-methylpiperazinyl, piperidinyl, morpholinyl, in each case unsubstituted or mono- or poly-substituted by one or more substituents each selected independently of one another from the group consisting of F, Cl, Br, I, OH, O—$C_{1-4}$-alkyl, $OCF_3$, $C_{1-4}$-alkyl, $CF_3$, SH, S—$C_{1-4}$-alkyl and $SCF_3$; phenyl, naphthyl, pyridyl or thienyl, in each case unsubstituted or mono- or poly-substituted by one or more substituents each selected independently of one another from the group consisting of F, Cl, Br, I, $NO_2$, CN, OH, O—$C_{1-4}$-alkyl, $OCF_3$, $C_{1-4}$-alkyl, $CF_3$, SH, S—$C_{1-4}$-alkyl and $SCF_3$;
or represents $CR^{1c}R^d$,
 wherein $R^{1c}$ and $R^{1d}$ each independently of the other denotes $C_{1-4}$-alkyl, saturated or unsaturated, branched or unbranched, unsubstituted or mono- or poly-substituted by one or more substituents each selected independently of one another from the group consisting of F, Cl, Br, I, OH and O—$C_{1-4}$-alkyl.

Particularly preferably, the radical $R^{109}$ is selected from the group consisting of phenyl, pyridyl or thienyl, in each case unsubstituted or mono- or poly-substituted by one or more substituents each selected independently of one another from the group consisting of F, Cl, Br, I, CN, OH, O—$C_{1-4}$-alkyl, $OCF_3$, $C_{1-4}$-alkyl, $CF_3$, SH, S—$C_{1-4}$-alkyl and $SCF_3$.

Most particularly preferably, $R^{109}$ represents phenyl, pyridyl and thienyl, unsubstituted or mono- or poly-substituted by one or more substituents each selected independently of one another from the group consisting of F, Cl, Br, I, CN, methyl, ethyl, n-propyl, isopropyl, n-butyl, sec-butyl, tert-butyl, O-methyl, O-ethyl, O-n-propyl, O-isopropyl, O-butyl, O-sec-butyl, O-tert-butyl, OH, $OCF_3$, $CF_3$, SH, S—$C_{1-4}$-alkyl and $SCF_3$.

In particular, $R^{109}$ represents phenyl, unsubstituted or mono- or poly-substituted by one or more substituents each selected independently of one another from the group consisting of F, Cl, Br, I, methyl, ethyl, n-propyl, isopropyl, n-butyl, sec-butyl, tert-butyl, O-methyl, O-ethyl, $OCF_3$, $CF_3$ and $SCF_3$.

In a further, particularly preferred embodiment
$A^{101}$ represents S and
$A^{102}$ represents $CR^{112}R^{113}$;
$R^{101}$ represents the partial structure (1-T1-1)

$$—(CR^{114a}R^{114b})_{m1}—B^1 \qquad (1\text{-T1-1}),$$

wherein
$R^{114a}$ and $R^{114b}$ each independently of the other represents H; F; Cl; Br; I; methyl; ethyl; n-propyl; isopropyl; n-butyl;

sec-butyl; tert-butyl; OH; O-methyl; O-ethyl; O—$(CH_2)_2$—O—$CH_3$; or O—$(CH_2)_2$—OH;

m1 represents 0, 1 or 2;

$B^1$ represents methyl; ethyl; n-propyl; isopropyl; n-butyl; sec-butyl; tert-butyl; cyclopropyl; cyclobutyl; cyclopentyl; cyclohexyl; cycloheptyl; adamantyl; bicyclo[2.2.1]heptyl; bicyclo[2.2.2]octyl; phenyl, pyridyl, thienyl, in each case unsubstituted or mono-, di- or tri-substituted by one, two or three substituents each selected independently of one another from the group consisting of F, Cl, Br, I, $NO_2$, CN, OH, O—$C_{1-4}$-alkyl, $OCF_3$, $C_{1-4}$-alkyl, C(=O)—OH, $CF_3$, $NH_2$, $NH(C_{1-4}$-alkyl), $N(C_{1-4}$-alkyl$)_2$, SH, S—$C_{1-4}$-alkyl, $SCF_3$ and $S(=O)_2OH$;

$R^{102}$, $R^{103}$ and $R^{104}$ each independently of the others represents H; F; Cl; methyl; ethyl; $CF_3$ or O-methyl;

$R^{105}$, $R^{106}$, $R^{107}$, $R^{108}$, $R^{110}$, $R^{111}$, $R^{112}$ and $R^{113}$ each independently of the others represents H; F; Cl; methyl; ethyl; n-propyl, isopropyl; cyclopropyl;

$R^{109}$ represents phenyl, pyridyl or thienyl, unsubstituted or mono- or poly-substituted by one or more substituents each selected independently of one another from the group consisting of F, Cl, Br, I, CN, methyl, ethyl, n-propyl, isopropyl, n-butyl, sec-butyl, tert-butyl, O-methyl, O-ethyl, O-n-propyl, O-isopropyl, O-butyl, O-sec-butyl, O-tert-butyl, OH, $OCF_3$, $CF_3$, SH, S—$C_{1-4}$-alkyl and $SCF_3$.

Another embodiment of the present invention relates to a compound of general formula (I), wherein the compound is selected from a compound according to general formula (2-I).

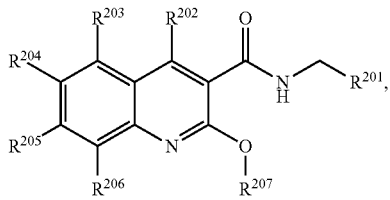

(2-I)

wherein $R^{201}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^{202}$ represents H; F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue$)_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, a $S(=O)_2$—O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{203}$, $R^{204}$, $R^{205}$ and $R^{206}$ each independently of one another represent H; F; Cl; Br; I; CN; $CF_3$; C(=O)H; C(=O)—OH; C(=O)—$NH_2$; $SCF_3$; S(=O)—OH; $NO_2$; $OCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue$)_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, a $S(=O)_2$—O—$C_{1-4}$-aliphatic residue, wherein the $C_{1-4}$ aliphatic residue may be in each case be unsubstituted or mono- or polysubstituted; a $NH(C_{1-4}$ aliphatic residue), a $N(C_{1-4}$ aliphatic residue$)_2$, a NH—C(=O)—$C_{1-4}$ aliphatic residue, a NH—$S(=O)_2$—$C_{1-4}$-aliphatic residue, a $N(C_{1-4}$ aliphatic residue)-C(=O)—$C_{1-4}$ aliphatic residue, or a $N(C_{1-4}$ aliphatic residue)-$S(=O)_2$—$C_{1-4}$ aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{207}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{207}$ denotes a 3 to 10 membered heterocycloaliphatic residue, the 3 to 10 membered heterocycloaliphatic residue is linked via a carbon atom, in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue$)_2$, a NH—C(=O)—$C_{1-4}$ aliphatic residue, a NH—$S(=O)_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, $S(=O)_2OH$, a $S(=O)_2$—$C_{1-4}$-aliphatic residue, a $S(=O)_2$—O—$C_{1-4}$-aliphatic residue, a $S(=O)_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—$NH(C_{1-4}$ aliphatic residue), and a C(=O)—$N(C_{1-4}$ aliphatic residue$)_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue$)_2$, a NH—C(=O)—$C_{1-4}$ aliphatic residue, a NH—$S(=O)_2$—

$C_{1-4}$ aliphatic residue, =O, OH, OCF$_3$, a O—$C_{1-4}$-aliphatic residue, a O—C(=O)—$C_{1-4}$-aliphatic residue, SH, SCF$_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, CF$_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH$_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

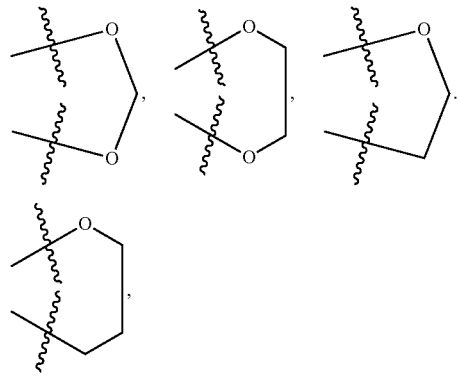

an NH($C_{1-4}$ aliphatic residue), an N($C_{1-4}$ aliphatic residue)$_2$, an NH—C(=O)—$C_{1-4}$ aliphatic residue, an NH—S(=O)$_2$—$C_{1-4}$ aliphatic residue, OH, OCF$_3$, a O—$C_{1-4}$-aliphatic residue, a O—C(=O)—$C_{1-4}$-aliphatic residue, SH, SCF$_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, CF$_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—NH$_2$, a C(=O)—NH($C_{1-4}$ aliphatic residue), and a C(=O)—N($C_{1-4}$ aliphatic residue)$_2$.

The compounds according to general formula (2-I) are known from WO 2012/025236 A1, which is fully included by reference.

Preferred embodiments of the compound according to general formula (2-I) have general formulae (2-Ia), (2-Ib), (2-Ic) or (2-Id):

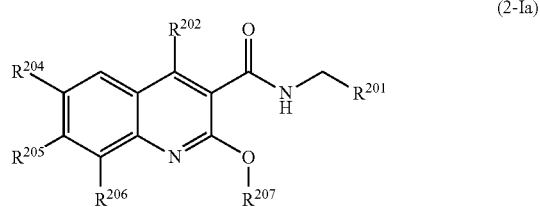

(2-Ia)

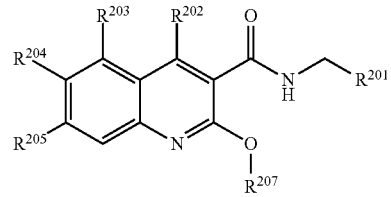

(2-Ib)

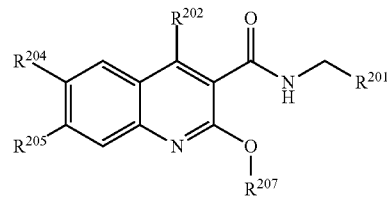

(2-Ic)

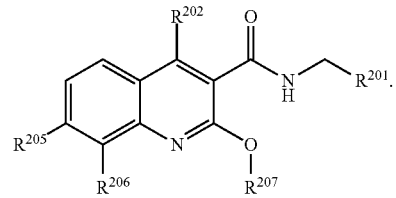

(2-Id)

Another preferred embodiment of present invention is a compound according to general formula (2-I), wherein
R$^{201}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCF$_3$, SH, SCF$_3$, a S—$C_{1-4}$-aliphatic residue, CF$_3$, CN, a $C_{1-4}$-aliphatic residue and C(=O)—OH,
wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue, C(=O)—OH, a $C_{3-6}$ cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

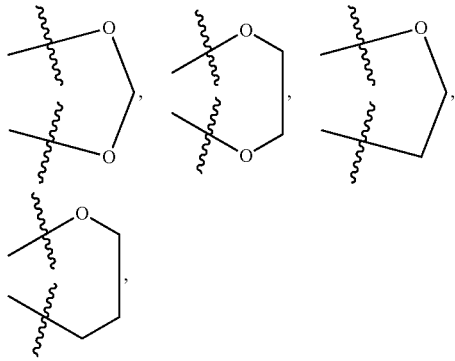

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and C(=O)—OH, $R^{202}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted;

a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, $R^{203}$, $R^{204}$, $R^{205}$ and $R^{206}$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a $NH(C_{1-4}$ aliphatic residue), a $N(C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{203}$, $R^{204}$, $R^{205}$ and $R^{206}$ is ≠H, $R^{207}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{207}$ denotes a 3 to 10 membered heterocycloaliphatic residue, the 3 to 10 membered heterocycloaliphatic residue is linked via a carbon atom.

In a preferred embodiment of the compound according to general formula (2-I), the residue $R^{201}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

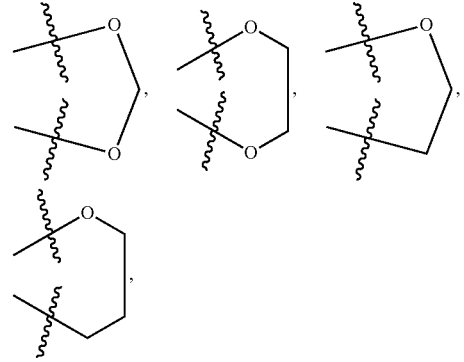

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and C(=O)—OH.

In a further preferred embodiment of the compound according to general formula (2-I), the residue $R^{201}$ represents the partial structure (2-T1)

   (2-T1), wherein m2 denotes 0, 1, 2, 3 or 4, preferably denotes 0, 1, or 2, $R^{208a}$ and $R^{208b}$ each independently of one another represent H, F, Cl, Br, I, $NO_2$, $NH_2$, a $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH, or together denote =O, preferably each independently of one another represent H, F, Cl, Br, I, $NH_2$, a $NH(C_{1-4}$ aliphatic residue), a $N(C_{1-4}$ aliphatic residue)$_2$, OH, O—$C_{1-4}$ aliphatic residue or a $C_{1-4}$ aliphatic residue, more preferably each independently of one another represent H, F, Cl, Br, I, an O—$C_{1-4}$ aliphatic residue or a $C_{1-4}$ aliphatic residue, even more preferably each independently of one another represent H, F, an O—$C_{1-4}$ aliphatic residue or a $C_{1-4}$ aliphatic residue, and $R^{208c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes a $C_{3-10}$-cycloaliphatic residue or a 3 to 10 membered heterocycloaliphatic residue, preferably when m2 is ≠0, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when m2 is =0—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

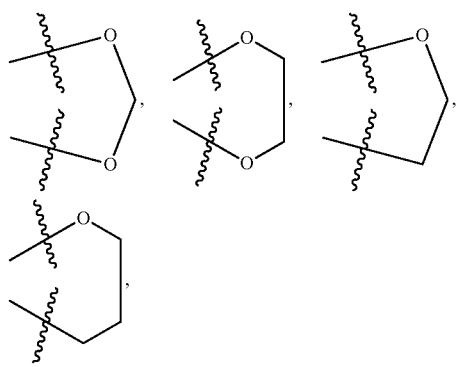

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

Preferably, $R^{201}$ represents the partial structure (2-T1), wherein m2 denotes 0, 1, or 2, $R^{208a}$ and $R^{208b}$ each independently of one another represent H, F, Cl, Br, I, an O—$C_{1-4}$ aliphatic residue or a $C_{1-4}$ aliphatic residue, preferably each independently of one another represent H, F, a O—$C_{1-2}$ aliphatic residue or a $C_{1-2}$ aliphatic residue, and $R^{208c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue and C(=O)—OH, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue and C(=O)—OH, or denotes—preferably when m2 is =0—an aryl or heteroaryl, in each case unsubstituted or mono- or polysubstituted with at least one substituent selected from the group consisting of F, Cl, Br, I, OH, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a $C_{3-6}$ cycloaliphatic residue, a 3 to 6 membered heterocycloaliphatic residue, benzyl, phenyl, thienyl, pyridyl, furyl, thiazolyl or oxazolyl, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue and C(=O)—OH.

More preferably,
$R^{201}$ represents the partial structure (2-T1),
wherein
m2 denotes 0, 1, or 2,
$R^{208a}$ and $R^{208b}$ each independently of one another represent H, F, Cl, Br, I, an O—$C_{1-4}$ aliphatic residue or a $C_{1-4}$ aliphatic residue, preferably each independently of one another represent H, F, a O—$C_{1-2}$ aliphatic residue or a $C_{1-2}$ aliphatic residue, and $R^{208c}$ denotes a $C_{1-4}$ aliphatic residue, unsubstituted or mono- or polysubstituted with at least one substituent selected from the group consisting of F, Cl, Br, I, an O—$C_{1-4}$ aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, CF$_3$ and an unsubstituted O—$C_{1-4}$-aliphatic residue, or denotes—preferably when m2 is =0—an aryl or heteroaryl, in each case unsubstituted or mono- or polysubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$ and C(=O)—O—C$_2$H$_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$, a $C_{1-4}$-aliphatic residue and C(=O)—OH.

In a further preferred embodiment of the compound according to general formula (2-I), the residue
$R^{201}$ represents the partial structure (2-T1),
wherein
m2 is 0, 1 or 2 and
$R^{208a}$ and $R^{208b}$ each independently of one another represent H, F, a O—$C_{1-4}$ aliphatic residue or a $C_{1-4}$ aliphatic residue; preferably H, F, CH$_3$ or OCH$_3$;

$R^{208c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, CF$_3$, and an unsubstituted $C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted aliphatic residue, CF$_3$, and an unsubstituted C$_{1-4}$-aliphatic residue, or wherein m2 is 0, R$^{208a}$ and R$^{208b}$ each independently of one another represent H, F, a O—C$_{1-4}$ aliphatic residue or a C$_{1-4}$ aliphatic residue; preferably H, F, CH$_3$ or OCH$_3$; and R$^{208c}$ denotes an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$.

Particularly preferred is a compound according to general formula (2-I) which has the following general formula (2-Ie):

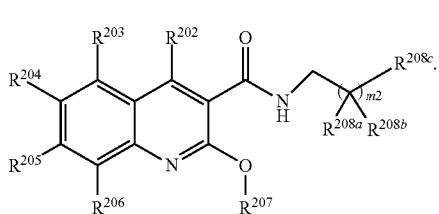

(2-Ie)

In a preferred embodiment of the compound according to general formula (2-I), the residue R$^{202}$ represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$ aliphatic residue may be in each case be unsubstituted or mono- or polysubstituted; a C$_{3-6}$-cycloaliphatic residue or a 3 to 6 membered heterocycloaliphatic residue, in each case unsubstituted or mono- or polysubstituted and in each case optionally bridged via a C$_{1-4}$ aliphatic group, which in turn may be unsubstituted or mono- or polysubstituted.

Preferably,

R$^{202}$ represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue, a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue, and wherein the C$_{3-6}$-cycloaliphatic residue or the 3 to 6 membered heterocycloaliphatic residue may in each case be optionally bridged via a C$_{1-4}$ aliphatic group, which in turn may be unsubstituted or mono- or polysubstituted with at least one substituent selected from the group consisting of F, Cl, Br, I, =O, OH, an unsubstituted C$_{1-4}$-aliphatic residue and an unsubstituted O—C$_{1-4}$-aliphatic residue.

More preferably,

R$^{202}$ represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue, cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted C$_{1-4}$-aliphatic residue and an unsubstituted O—C$_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an C$_{1-4}$ aliphatic group, which in turn may be unsubstituted or mono- or polysubstituted with at least one substituent selected from the group consisting of F, Cl, OH, an unsubstituted C$_{1-4}$-aliphatic residue and an unsubstituted O—C$_{1-4}$-aliphatic residue.

Even more preferably,

R$^{202}$ represents H; F; Cl; Br; I; CN; CF$_3$; NO$_2$; OCF$_3$; SCF$_3$; methyl; ethyl; n-propyl; iso-propyl; n-butyl; sec.-butyl; tert.-butyl; O-methyl; O-ethyl; O—(CH$_2$)$_2$—O—CH$_3$; O—(CH$_2$)$_2$—OH; S-Methyl; S-Ethyl; cyclopropyl, cyclobutyl, cyclopentyl, and cyclohexyl.

Still more preferably,

R$^{202}$ is selected from the group consisting of H; F; Cl; CF$_3$; CN; SCF$_3$; OCF$_3$; CH$_3$; C$_2$H$_5$; n-propyl; iso-propyl; t-butyl; cyclopropyl; O—CH$_3$ and O—C$_2$H$_5$;

In particular,

R$^{202}$ is selected from the group consisting of H; F; Cl; CF$_3$; CH$_3$; C$_2$H$_5$, iso-propyl; cyclopropyl; and O—CH$_3$;

In a particular preferred embodiment of the compound according to general formula (2-I), the residue R$^{202}$ is ≠H.

In a preferred embodiment of the compound according to general formula (2-I), the residues R$^{203}$, R$^{204}$, R$^{205}$ and R$^{206}$ each independently of one another represent H; F; Cl; Br; I; CN; CF$_3$; OCF$_3$; SCF$_3$; C(=O) H; C(=O)—OH; C(=O)—NH$_2$; S(=O)$_2$—OH; NO$_2$; a C$_{1-4}$-aliphatic residue, a C(=O)—C$_{1-4}$ aliphatic residue, a C(=O)—O—C$_{1-4}$ aliphatic residue, a C(=O)—NH—C$_{1-4}$ aliphatic residue, a C(=O)—N(C$_{1-4}$ aliphatic residue)$_2$, a O—C$_{1-4}$-aliphatic residue, a O—C(=O)—C$_{1-4}$-aliphatic residue, a S—C$_{1-4}$-aliphatic residue, a S(=O)$_2$—C$_{1-4}$-aliphatic residue, a NH(C$_{1-4}$ aliphatic residue), a N(C$_{1-4}$ aliphatic residue)$_2$, a NH—C(=O)—C$_{1-4}$ aliphatic residue, and a NH—S(=O)$_2$—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{203}$, $R^{204}$, $R^{205}$ and $R^{206}$ is ≠H.

Preferably, $R^{203}$, $R^{204}$, $R^{205}$ and $R^{206}$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{203}$, $R^{204}$, $R^{205}$ and $R^{206}$ is ≠H.

More preferably, $R^{203}$, $R^{204}$, $R^{205}$ and $R^{206}$ each independently of one another represent H; F; Cl; Br; I; CN; $CF_3$; $OCF_3$; $SCF_3$; C(=O)H; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a S—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue, unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{203}$, $R^{204}$, $R^{205}$ and $R^{206}$ is ≠H.

In a further preferred embodiment of the present invention $R^{203}$, $R^{204}$, $R^{205}$ and $R^{206}$ each independently of one another are selected from the group consisting of H; F; Cl; Br; I; $NO_2$; $CF_3$; CN; $OCF_3$; $SCF_3$; a (C=O)—$C_{1-4}$ aliphatic residue, a $C_{1-4}$ aliphatic residue, O—$C_{1-4}$ aliphatic residue, a S—$C_{1-4}$ aliphatic residue, wherein the $C_{1-4}$-aliphatic residue in each case may be unsubstituted or mono- or polysubstituted with at least one substituent selected from the group consisting of F, Cl, and O—$CH_3$;

preferably on the condition that at least one of $R^{203}$, $R^{204}$, $R^{205}$ and $R^{206}$ is ≠H.

Preferably, $R^{203}$, $R^{204}$, $R^{205}$ and $R^{206}$ each independently of one another are selected from the group consisting of H; F; Cl; Br; I; $NO_2$; $CF_3$; CN; $OCF_3$; $SCF_3$; methyl; ethyl; n-propyl; iso-propyl; n-butyl; sec.-butyl; tert.-butyl; cyclopropyl; C(=O)-methyl; C(=O)-ethyl; (C=O)-isopropyl; (C=O)-t-butyl; O-methyl; O-ethyl; O-isopropyl; O-t-butyl; O—$(CH_2)_2$—O—$CH_3$; S-Methyl; S-Ethyl;

preferably on the condition that at least one of $R^{203}$, $R^{204}$, $R^{205}$ and $R^{206}$ is ≠H.

In particular, $R^{203}$, $R^{204}$, $R^{205}$ and $R^{206}$ are each independently of one another are selected from the group consisting of H; F; Cl; Br; I; $NO_2$; $CF_3$; CN; (C=O)-methyl; (C=O)-ethyl; (C=O)-isopropyl; (C=O)-t-butyl; methyl; ethyl; isopropyl; t-butyl; O-methyl; O-Ethyl; O-isopropyl; O-t-butyl; $OCF_3$; S-methyl; S-ethyl; and $SCF_3$;

preferably on the condition that at least one of $R^{203}$, $R^{204}$, $R^{205}$ and $R^{206}$ is ≠H.

More particularly, $R^{203}$, $R^{204}$, $R^{205}$ and $R^{206}$ are each independently of one another selected from the group consisting of H; F; Cl; Br; $CF_3$; CN; $OCF_3$ and $NO_2$;

preferably on the condition that at least one of $R^{203}$, $R^{204}$, $R^{205}$ and $R^{206}$ is ≠H.

Most preferred, $R^{203}$, $R^{204}$ and $R^{206}$ each independently of one another are selected from the group consisting of H and F; and $R^{205}$ denotes F; Br; $CF_3$; $OCF_3$; CN; or $NO_2$.

In a particular preferred embodiment of the compound according to general formula (2-I) at least one of the residues $R^{203}$, $R^{204}$, $R^{205}$ and $R^{206}$ is ≠H.

In a preferred embodiment of the compound according to general formula (2-I), the residue $R^{207}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{207}$ denotes a 3 to 10 membered heterocycloaliphatic residue, the 3 to 10 membered heterocycloaliphatic residue is linked via a carbon atom.

In a further preferred embodiment of the compound according to general formula (2-I), the residue $R^{207}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, CN, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, a $C_{1-4}$-aliphatic residue, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, and a $C_{1-4}$-aliphatic residue.

on the condition that if $R^{207}$ denotes a 3 to 10 membered heterocycloaliphatic residue, the 3 to 10 membered heterocycloaliphatic residue is linked via a carbon atom.

Preferably, $R^{207}$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue.

on the condition that if $R^{207}$ denotes a 3 to 10 membered heterocycloaliphatic residue, the 3 to 10 membered heterocycloaliphatic residue is linked via a carbon atom.

More preferably, $R^{207}$ denotes a $C_{1-8}$-aliphatic residue, preferably a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, $CF_3$, a C(=O)—O—$C_{1-4}$-aliphatic residue, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue is bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue.

Even more preferably, $R^{207}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue
wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-10}$-cycloaliphatic residue or the 3 to 10 membered heterocycloaliphatic residue is in each case bridged via a unsubstituted $C_{1-8}$ aliphatic group, preferably an unsubstituted $C_{1-4}$ aliphatic group.

Still more preferably, $R^{207}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue,
wherein the $C_{1-4}$-aliphatic residue in each case is unsubstituted,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue,
wherein the $C_{1-4}$-aliphatic residue in each case may be unsubstituted or mono- or polysubstituted with OH or an unsubstituted O—$C_{1-4}$-aliphatic residue,
and wherein the $C_{3-10}$-cycloaliphatic residue or the 3 to 10 membered heterocycloaliphatic residue is in each case bridged via a unsubstituted $C_{1-4}$ aliphatic group.

In particular, $R^{207}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue,
wherein the $C_{1-4}$-aliphatic residue in each case is unsubstituted.

Most preferred, $R^{207}$ denotes a $C_{1-6}$-aliphatic residue, unsubstituted or mono- or polysubstituted with at least one substituent selected from the group consisting of F, $CF_3$, Cl, OH, and O-methyl.

Preferred is also a compound according to general formula (2-I), wherein $R^{201}$ represents the partial structure (2-T1), $$-(CR^{208a}R^{208b})_{m2}-R^{208c} \qquad (2-T1),$$

wherein
m2 is 0, 1 or 2 and
$R^{208a}$ and $R^{208b}$ each independently of one another represent H, F, a O—$C_{1-4}$ aliphatic residue or a $C_{1-4}$ aliphatic residue; preferably H, F, $CH_3$ or $OCH_3$;
$R^{208c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or wherein
m2 is 0,
$R^{208a}$ and $R^{208b}$ each independently of one another represent H, F, a O—$C_{1-4}$ aliphatic residue or a $C_{1-4}$ aliphatic residue; preferably H, F, $CH_3$ or $OCH_3$; and
$R^{208c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, $R^{202}$ is selected from the group consisting of H; F; Cl; $CF_3$; $CH_3$; $C_2H_5$, iso-propyl; cyclopropyl; and O—$CH_3$;
$R^{203}$, $R^{204}$, $R^{205}$ and $R^{206}$ are each independently of one another selected from the group consisting of H; F; Cl; Br; $CF_3$; CN; $OCF_3$ and $NO_2$;
preferably on the condition that at least one of $R^{203}$, $R^{204}$, $R^{205}$ and $R^{206}$ is ≠H,
$R^{207}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue
wherein the $C_{1-4}$-aliphatic residue in each case is unsubstituted.

Particularly preferred is also a compound according to general formula (2-I), wherein
$R^{201}$ represents aryl, preferably phenyl, or heteroaryl, preferably pyridyl or thienyl, in each case unsubstituted or mono- or disubstituted with at least one substituent selected from the group consisting of F, Cl, Br, I, OH, $OCH_3$, $OCF_3$, $CF_3$, CN, and $CH_3$, preferably represents phenyl, unsubstituted or mono- or disubstituted with at least one substituent selected from the group consisting of F, Cl, Br, I, OH, OCH₃, OCF₃, CF₃, CN, and CH₃;

$R^{202}$ is selected from the group consisting of H, F, Cl, CF₃, CH₃, C₂H₅, iso-propyl, cyclopropyl, and O—CH₃; preferably is selected from the group consisting of CH₃, C₂H₅, OCH₃ and CF₃;

$R^{203}$, $R^{204}$, $R^{205}$ and $R^{206}$ are each independently of one another selected from the group consisting of H, F, Cl, Br, CF₃, CN, OCF₃ and NO₂;

preferably on the condition that at least one of $R^{203}$, $R^{204}$, $R^{205}$ and $R^{206}$ is ≠H, more preferably on the condition that $R^{205}$ is ≠H;

$R^{207}$ denotes a saturated $C_{1-4}$-aliphatic residue, unsubstituted or mono- or disubstituted with at least one substituent selected from the group consisting of F, Cl, Br, I, OH, O—CH₃, OCF₃, SCF₃, and CF₃.

Another embodiment of the present invention therefore relates to a compound of general formula (I), wherein the compound is selected from a compound according to general formula (3-I),

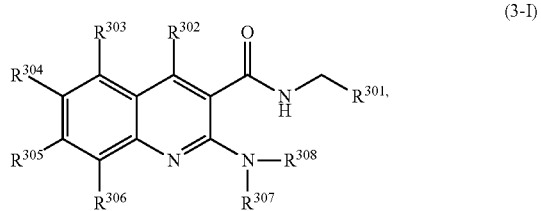

(3-I)

wherein $R^{301}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^{302}$ represents H; F; Cl; Br; I; CN; CF₃; C(=O)H; NO₂; OCF₃; SCF₃; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)₂, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)₂—$C_{1-4}$-aliphatic residue, a S(=O)₂—O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{303}$, $R^{304}$, $R^{305}$ and $R^{306}$ each independently of one another represent H; F; Cl; Br; I; CN; CF₃; C(=O)H; C(=O)—OH; O(=O)—NH₂; SCF₃; S(=O)₂—OH; NO₂; OCF₃; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)₂, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)₂—$C_{1-4}$-aliphatic residue, a S(=O)₂—O—$C_{1-4}$-aliphatic residue, wherein the $C_{1-4}$ aliphatic residue may be in each case be unsubstituted or mono- or polysubstituted; a NH($C_{1-4}$ aliphatic residue), a N($C_{1-4}$ aliphatic residue)₂, a NH—C(=O)—$C_{1-4}$ aliphatic residue, a NH—S(=O)₂—$C_{1-4}$-aliphatic residue, a N($C_{1-4}$ aliphatic residue)-C(=O)—$C_{1-4}$ aliphatic residue, or a N($C_{1-4}$ aliphatic residue)-S(=O)₂—$C_{1-4}$ aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

on the condition that at least one of $R^{303}$, $R^{304}$, $R^{305}$ and $R^{306}$ is ≠H, $R^{307}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{307}$ denotes a 3 to 10 membered heterocycloaliphatic residue, the binding is carried out via a carbon atom of the 3 to 10 membered heterocycloaliphatic residue;

$R^{308}$ denotes H or a $C_{1-10}$-aliphatic residue, preferably a $C_{1-4}$-aliphatic residue, unsubstituted or mono- or polysubstituted;

or $R^{307}$ and $R^{308}$ form together with the nitrogen atom connecting them a 3 to 10 membered heterocycloaliphatic residue, preferably a 3 to 6 membered heterocycloaliphatic residue, unsubstituted or mono- or polysubstituted;

in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, NO₂, NH₂, an NH($C_{1-4}$ aliphatic residue), an N($C_{1-4}$ aliphatic residue)₂, a NH—C(=O)—$C_{1-4}$ aliphatic residue, a NH—S(=O)₂—$C_{1-4}$ aliphatic residue, =O, OH, OCF₃, a O—$C_{1-4}$-aliphatic residue, a O—C(=O)—$C_{1-4}$-aliphatic residue, SH, SCF₃, a S—$C_{1-4}$-aliphatic residue, S(=O)₂OH, a S(=O)₂—$C_{1-4}$-aliphatic residue, a S(=O)₂—O—$C_{1-4}$-aliphatic residue, a S(=O)₂—NH—$C_{1-4}$-aliphatic residue, CN, CF₃, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH₂, a C(=O)—NH($C_{1-4}$ aliphatic residue), and a C(=O)—N($C_{1-4}$ aliphatic residue)₂;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, NO₂, NH₂, an NH($C_{1-4}$ aliphatic residue), an N($C_{1-4}$ aliphatic residue)₂, a NH—C(=O)—$C_{1-4}$ aliphatic residue, a NH—S(=O)$_2$—$C_{1-4}$ aliphatic residue, =O, OH, OCF$_3$, a O—$C_{1-4}$-aliphatic residue, a O—C(=O)—$C_{1-4}$-aliphatic residue, SH, SCF$_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, CF$_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—NH$_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

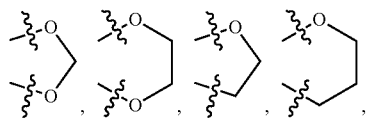

an NH($C_{1-4}$ aliphatic residue), an N($C_{1-4}$ aliphatic residue)$_2$, an NH—C(=O)—$C_{1-4}$ aliphatic residue, an NH—S(=O)$_2$—$C_{1-4}$ aliphatic residue, OH, OCF$_3$, a O—$C_{1-4}$-aliphatic residue, a O—C(=O)—$C_{1-4}$-aliphatic residue, SH, SCF$_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, CF$_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—NH$_2$, a C(=O)—NH($C_{1-4}$ aliphatic residue), and a C(=O)—N($C_{1-4}$ aliphatic residue)$_2$.

The compounds according to general formula (3-I) are known from WO 2012/025237 A1, which is fully included by reference.

Preferred embodiments of the compound according to general formula (3-I) have general formulae (3-Ia), (3-Ib), (3-Ic) or (3-Id):

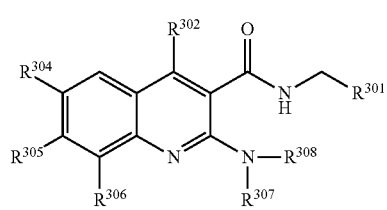

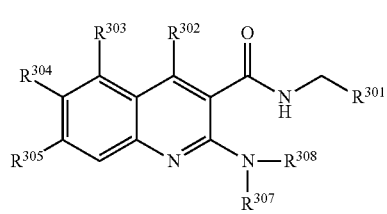

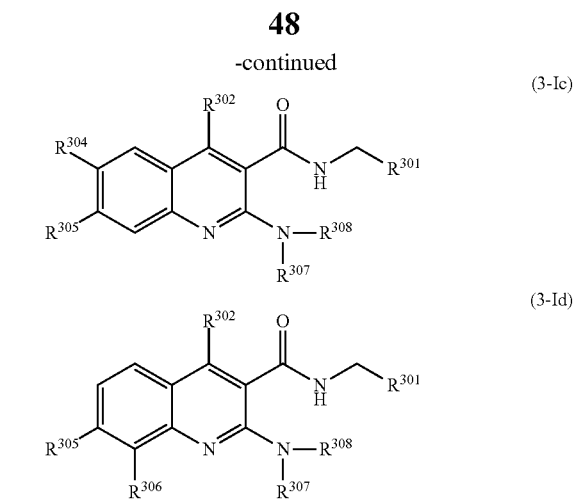

Another preferred embodiment of present invention is a compound according to general formula (I), wherein $R^{301}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$-aliphatic residue, OCF$_3$, SH, SCF$_3$, a S—$C_{1-4}$-aliphatic residue, CF$_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, NO$_2$, NH$_2$, an NH($C_{1-4}$ aliphatic residue), an N($C_{1-4}$ aliphatic residue)$_2$, OH, =O, an O—$C_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

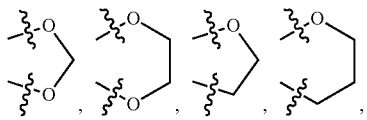

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN and C(=O)—OH, R$^{302}$ represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$ aliphatic residue may be in each case be unsubstituted or mono- or polysubstituted; a C$_{3-6}$-cycloaliphatic residue or a 3 to 6 membered heterocycloaliphatic residue, in each case unsubstituted or mono- or polysubstituted and in each case optionally bridged via a C$_{1-4}$ aliphatic group, which in turn may be unsubstituted or mono- or polysubstituted, preferably represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue; a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and an O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue, and wherein the C$_{3-6}$-cycloaliphatic residue or the 3 to 6 membered heterocycloaliphatic residue may in each case be optionally bridged via a C$_{1-4}$ aliphatic group, which in turn may be unsubstituted or mono- or polysubstituted with at least one substituent selected from the group consisting of F, Cl, Br, I, =O, OH, an unsubstituted C$_{1-4}$-aliphatic residue and an unsubstituted O—C$_{1-4}$-aliphatic residue, R$^{303}$, R$^{304}$, R$^{305}$ and R$^{306}$ each independently of one another represent H; F; Cl; Br; I; CN; CF$_3$; OCF$_3$; SCF$_3$; C(=O)H; C(=O)—OH; C(=O)—NH$_2$; S(=O)$_2$—OH; NO$_2$; a C$_{1-4}$-aliphatic residue, a C(=O)—C$_{1-4}$ aliphatic residue, a C(=O)—O—C$_{1-4}$ aliphatic residue, a C(=O)—NH—C$_{1-4}$ aliphatic residue, a C(=O)—N(C$_{1-4}$ aliphatic residue)$_2$, a O—C$_{1-4}$-aliphatic residue, a O—C(=O)—C$_{1-4}$-aliphatic residue, a S—C$_{1-4}$-aliphatic residue, a S(=O)$_2$—C$_{1-4}$-aliphatic residue, a NH(C$_{1-4}$ aliphatic residue), a N(C$_{1-4}$ aliphatic residue)$_2$, a NH—C(=O)—C$_{1-4}$ aliphatic residue, and a NH—S(=O)$_2$—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and a O—C$_{1-4}$-aliphatic residue; a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and a O—C$_{1-4}$-aliphatic residue, and in each case optionally bridged via an unsubstituted C$_{1-4}$ aliphatic group, on the condition that at least one of R$^{303}$, R$^{304}$, R$^{305}$ and R$^{306}$ is ≠H, R$^{307}$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue, a C(=O)—O—C$_{1-4}$-aliphatic residue, and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C(=O)—O—C$_{1-4}$-aliphatic residue a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, a C(=O)—O—C$_{1-4}$-aliphatic residue, OCF$_3$, SH, SCF$_3$, a S—C$_{1-4}$ aliphatic residue, CF$_3$, CN, a C$_{1-4}$-aliphatic residue and C(=O)—OH, on the condition that if R$^{307}$ denotes a 3 to 10 membered heterocycloaliphatic residue, the 3 to 10 membered heterocycloaliphatic residue is linked via a carbon atom, and R$^{308}$ denotes H or a C$_{1-10}$-aliphatic residue, preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or R$^{307}$ and R$^{308}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

In a preferred embodiment of the compound according to general formula (3-I), the residue R$^{301}$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

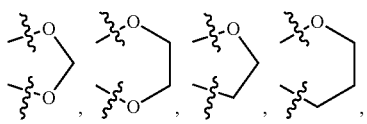

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or poly-substituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN and C(=O)—OH.

In a further preferred embodiment of the compound according to general formula (I), the residue $R^{301}$ represents the partial structure (3-T1)

—$(CR^{308a}R^{308b})_{m3}$—$R^{308c}$      (3-T1), wherein m3 denotes 0, 1, 2, 3 or 4, preferably denotes 0, 1, or 2, $R^{308a}$ and $R^{308b}$ each independently of one another represent H, F, Cl, Br, I, $NO_2$, $NH_2$, a $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH, or together denote =O, preferably each independently of one another represent H, F, Cl, Br, I, $NH_2$, a $NH(C_{1-4}$ aliphatic residue), a $N(C_{1-4}$ aliphatic residue$)_2$, OH, O—$C_{1-4}$ aliphatic residue or a $C_{1-4}$ aliphatic residue, more preferably each independently of one another represent H, F, Cl, Br, I, an O—$C_{1-4}$ aliphatic residue or a $C_{1-4}$ aliphatic residue, even more preferably each independently of one another represent H, F, an O—$C_{1-4}$ aliphatic residue or a $C_{1-4}$ aliphatic residue, and $R^{308c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes a $C_{3-10}$-cycloaliphatic residue or a 3 to 10 membered heterocycloaliphatic residue, preferably when m is ≠0, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when m3 is =0—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, 3 to 6 membered heterocycloaliphatic residue,

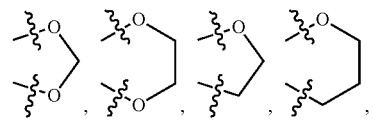

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

Preferably, $R^{301}$ represents the partial structure (3-T1), wherein m3 denotes 0, 1, or 2, $R^{308a}$ and $R^{308b}$ each independently of one another represent H, F, Cl, Br, I, an O—$C_{1-4}$ aliphatic residue or a $C_{1-4}$ aliphatic residue, preferably each independently of one another represent H, F, a O—$C_{1-2}$ aliphatic residue or a $C_{1-2}$ aliphatic residue, and $R^{308c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes—preferably when m3 is =0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl or oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$ a $C_{1-4}$-aliphatic residue and C(=O)—OH.

More preferably, $R^{301}$ represents the partial structure (3-T1), wherein m3 denotes 0, 1, or 2, $R^{308a}$ and $R^{308b}$ each independently of one another represent H, F, Cl, Br, I, an O—$C_{1-4}$ aliphatic residue or a $C_{1-4}$ aliphatic residue, preferably each independently of one another represent H, F, a O—$C_{1-2}$ aliphatic residue or a $C_{1-2}$ aliphatic residue, and $R^{308c}$ denotes a $C_{1-4}$ aliphatic residue, unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent consisting of F, Cl, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes—preferably when m3 is =0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$ a C$_{1-4}$-aliphatic residue and C(=O)—OH.

In a further preferred embodiment of the compound according to general formula (3-I), the residue R$^{301}$ represents the partial structure (3-T1),
wherein
m3 is 0, 1 or 2 and
R$^{308a}$ and R$^{308b}$ each independently of one another represent H, F, a O—C$_{1-4}$ aliphatic residue or a C$_{1-4}$ aliphatic residue; preferably H, F, CH$_3$ or OCH$_3$;
R$^{308c}$ denotes a C$_{1-4}$ aliphatic residue, unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue,
or
wherein
m3 is 0,
R$^{308a}$ and R$^{308b}$ each independently of one another represent H, F, a O—C$_{1-4}$ aliphatic residue or a C$_{1-4}$ aliphatic residue; preferably H, F, CH$_3$ or OCH$_3$; and
R$^{308c}$ denotes an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$.

Particularly preferred is a compound according to general formula (3-I) which has the following general formula (3-Ie):

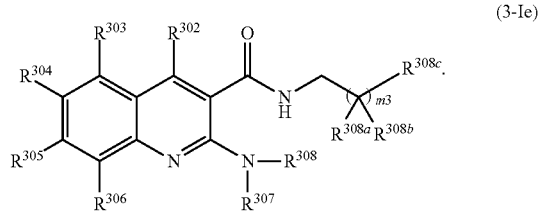

(3-Ie)

In a preferred embodiment of the compound according to general formula (3-I), the residue R$^{302}$ represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$ aliphatic residue may be in each case be unsubstituted or mono- or polysubstituted; a C$_{3-6}$-cycloaliphatic residue or a 3 to 6 membered heterocycloaliphatic residue, in each case unsubstituted or mono- or polysubstituted and in each case optionally bridged via a C$_{1-4}$ aliphatic group, which in turn may be unsubstituted or mono- or polysubstituted.

Preferably,
R$^{302}$ represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue,
wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue,
a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and a O—C$_{1-4}$-aliphatic residue,
wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue,
and wherein the C$_{3-6}$-cycloaliphatic residue or the 3 to 6 membered heterocycloaliphatic residue may in each case be optionally bridged via a C$_{1-4}$ aliphatic group, which in turn may be unsubstituted or mono- or polysubstituted with at least one substituent selected from the group consisting of F, Cl, Br, I, =O, OH, an unsubstituted C$_{1-4}$-aliphatic residue and an unsubstituted O—C$_{1-4}$-aliphatic residue.

More preferably,
R$^{302}$ represents H; F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue,
wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue,
cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted C$_{1-4}$-aliphatic residue and an unsubstituted O—C$_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an C$_{1-4}$ aliphatic group, which in turn may be unsubstituted or mono- or polysubstituted with at least one substituent selected from the group consisting of F, Cl, OH, an unsubstituted C$_{1-4}$-aliphatic residue and an unsubstituted O—C$_{1-4}$-aliphatic residue.

Even more preferably,
R$^{302}$ represents H; F; Cl; Br; I; CN; CF$_3$; NO$_2$; OCF$_3$; SCF$_3$; methyl; ethyl; n-propyl; iso-propyl; n-butyl; sec-butyl; tert-butyl; O-methyl; O-ethyl; O—(CH$_2$)$_2$—O—CH$_3$;

O—$(CH_2)_2$—OH; S-Methyl; S-Ethyl; cyclopropyl, cyclobutyl, cyclopentyl, and cyclohexyl.

Still more preferably, $R^{302}$ is selected from the group consisting of H; F; Cl; Br; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$.

In particular, $R^{302}$ is selected from the group consisting of H; F; Cl; Br; $CF_3$; $CH_3$; $C_2H_5$, iso-propyl; cyclopropyl; and O—$CH_3$.

In a particular preferred embodiment of the compound according to general formula (3-I), the residue $R^{302}$ is ≠H.

In another preferred embodiment of the compound according to general formula (3-I), the residues $R^{303}$, $R^{304}$, $R^{305}$ and $R^{306}$ each independently of one another represent H; F; Cl; Br; I; CN; $CF_3$; $OCF_3$; $SCF_3$; C(=O) H; C(=O)—OH; C(=O)—$NH_2$; $S(=O)_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—$S(=O)_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, on the condition that at least one of $R^{303}$, $R^{304}$, $R^{305}$ and $R^{306}$ is ≠H.

Preferably, $R^{303}$, $R^{304}$, $R^{305}$ and $R^{306}$ each independently of one another represent H; F; Cl; Br; I; CN; $CF_3$; $OCF_3$; $SCF_3$; C(=O) H; C(=O)—OH; C(=O)—$NH_2$; $S(=O)_2$—OH; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, on the condition that at least one of $R^{303}$, $R^{304}$, $R^{305}$ and $R^{306}$ is ≠H.

More preferably, $R^{303}$, $R^{304}$, $R^{305}$ and $R^{306}$ each independently of one another represent H; F; Cl; Br; I; CN; $CF_3$; $OCF_3$; $SCF_3$; C(=O) H; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a S—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue, unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, on the condition that at least one of $R^{303}R^{304}$, $R^{305}$ and $R^{306}$ is ≠H.

In a further preferred embodiment of the present invention $R^{303}$, $R^{304}$, $R^{305}$ and $R^{306}$ each independently of one another are selected from the group consisting of H; F; Cl; Br; I; $NO_2$; $CF_3$; CN; $OCF_3$; $SCF_3$; a (C=O)—$C_{1-4}$aliphatic residue, a $C_{1-4}$aliphatic residue, O—$C_{1-4}$ aliphatic residue, a S—$C_{1-4}$aliphatic residue, wherein the $C_{1-4}$-aliphatic residue in each case may be unsubstituted or mono- or polysubstituted with at least one substituent selected from the group consisting of F, Cl, and O—$CH_3$;

on the condition that at least one of $R^{303}$, $R^{304}$, $R^{305}$ and $R^{306}$ is ≠H.

Preferably, $R^{303}$, $R^{304}$, $R^{305}$ and $R^{306}$ each independently of one another are selected from the group consisting of H; F; Cl; Br; I; $NO_2$; $CF_3$; CN; $OCF_3$; $SCF_3$; methyl; ethyl; n-propyl; iso-propyl; n-butyl; sec.-butyl; tert.-butyl; cyclopropyl; C(=O)-methyl; C(=O)-ethyl; (C=O)-isopropyl; (C=O)-t-butyl; O-methyl; O-ethyl; O-isopropyl; O-t-butyl; O—$(CH_2)_2$—O—$CH_3$; S-Methyl; S-Ethyl;

on the condition that at least one of $R^{303}$, $R^{304}$, $R^{305}$ and $R^{306}$ is ≠H.

In particular, $R^{303}$, $R^{304}$, $R^{305}$ and $R^{306}$ are each independently of one another are selected from the group consisting of H; F; Cl; Br; I; $NO_2$; $CF_3$; CN; (C=O)-methyl; (C=O)-ethyl; (C=O)-isopropyl; (C=O)-t-butyl; methyl; ethyl; isopropyl; t-butyl; O-methyl; O-Ethyl; O-isopropyl; O-t-butyl; $OCF_3$; S-methyl; S-ethyl; and $SCF_3$;

on the condition that at least one of $R^{303}$, $R^{304}$, $R^{305}$ and $R^{306}$ is ≠H.

More particularly, $R^{303}$, $R^{304}$, $R^{305}$ and $R^{306}$ are each independently of one another selected from the group consisting of H; F; Cl; Br; $CF_3$; CN; $OCF_3$ and $NO_2$;

on the condition that at least one of $R^{303}$, $R^{304}$, $R^{305}$ and $R^{306}$ is ≠H.

Most preferred, $R^{303}$, $R^{304}$ and $R^{306}$ each independently of one another represent H or F; and $R^{305}$ denotes F; $CF_3$; $OCF_3$; CN; or $NO_2$.

In a preferred embodiment of the compound according to general formula (3-I), the residue $R^{307}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O) OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{307}$ denotes a 3 to 10 membered heterocycloaliphatic residue, the 3 to 10 membered heterocycloaliphatic residue is linked via a carbon atom. and $R^{308}$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or $R^{307}$ and $R^{308}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

In a further preferred embodiment of the compound according to general formula (3-I), the residue $R^{307}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, a $C_{1-4}$-aliphatic residue, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, and a $C_{1-4}$-aliphatic residue, on the condition that if $R^{307}$ denotes a 3 to 10 membered heterocycloaliphatic residue, the 3 to 10 membered heterocycloaliphatic residue is linked via a carbon atom, and $R^{308}$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or $R^{307}$ and $R^{308}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue.

Preferably, $R^{307}$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a C(=O)—O—$C_{1-4}$-aliphatic residue, a S—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue, on the condition that if $R^{307}$ denotes a 3 to 10 membered heterocycloaliphatic residue, the 3 to 10 membered heterocycloaliphatic residue is linked via a carbon atom, and $R^{308}$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or $R^{307}$ and $R^{308}$ form together with the nitrogen atom connecting them a 3 to 10 membered heterocycloaliphatic residue, preferably a 3 to 6 membered heterocycloaliphatic residue, more preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue.

More preferably, $R^{307}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, $CF_3$, a C(=O)—O—$C_{1-4}$-aliphatic residue, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue is in each case bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue, and $R^{308}$ denotes H or a $C_{1-6}$-aliphatic residue, preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or $R^{307}$ and $R^{308}$ form together with the nitrogen atom connecting them a 3 to 6 membered heterocycloaliphatic residue, preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue.

Even more preferably, $R^{307}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue is in each case bridged via a unsubstituted $C_{1-8}$ aliphatic group, preferably an unsubstituted $C_{1-4}$ aliphatic group, and $R^{308}$ denotes H or an unsubstituted $C_{1-4}$-aliphatic residue, preferably selected from the group consisting of methyl, ethyl, n-propyl, 2-propyl, n-butyl, isobutyl, sec.-butyl and tert.-butyl, more preferably selected from the group consisting of methyl and ethyl or $R^{307}$ and $R^{308}$ form together with the nitrogen atom connecting them a 3 to 6 membered heterocycloaliphatic residue, preferably selected from the group consisting of morpholinyl, piperidinyl, pyrrolidinyl, and azetidinyl, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$ aliphatic residue.

Still more preferably, $R^{307}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue, wherein the $C_{1-4}$-aliphatic residue in each case is unsubstituted, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue.

and wherein the $C_{3-10}$-cycloaliphatic residue or the 3 to 10 membered heterocycloaliphatic residue is in each case bridged via a unsubstituted $C_{1-4}$ aliphatic group, $R^{308}$ denotes H or an unsubstituted $C_{1-4}$-aliphatic residue, preferably H, methyl, ethyl, n-propyl, 2-propyl, n-butyl, isobutyl, sec.-butyl or tert.-butyl, or $R^{307}$ and $R^{308}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue.

Most preferred, $R^{307}$ denotes a $C_{1-6}$-aliphatic residue, unsubstituted or mono- or polysubstituted with at least one substituent selected from the group consisting of F, Cl, OH, and O-methyl, preferably unsubstituted or mono- or polysubstituted with at least one substituent selected from the group consisting of F, Cl, and O-methyl, more preferably unsubstituted or mono- or polysubstituted with at least one substituent selected from the group consisting of F and O-methyl, $R^{308}$ denotes H, methyl, ethyl, n-propyl, 2-propyl, n-butyl, isobutyl, sec.-butyl or tert.-butyl, preferably methyl or ethyl, or $R^{307}$ and $R^{308}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue, more preferably unsubstituted or mono- or polysubstituted with at least one substituent selected from the group consisting of F, Cl and a O—$C_{1-4}$ aliphatic residue, preferably O-methyl.

Particularly preferred is also a compound according to general formula (I), wherein $R^{301}$ represents the partial structure (3-T1), $$—(CR^{308a}R^{308b})_{m3}—R^{308c} \qquad (3\text{-}T1),$$

wherein
m3 is 0, 1 or 2 and
$R^{308a}$ and $R^{308b}$ each independently of one another represent H, F, a O—$C_{1-4}$ aliphatic residue or a $C_{1-4}$ aliphatic residue; preferably H, F, $CH_3$ or $OCH_3$;
$R^{308c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or
wherein
m3 is 0,
$R^{308a}$ and $R^{308b}$ each independently of one another represent H, F, a O—$C_{1-4}$ aliphatic residue or a $C_{1-4}$ aliphatic residue; preferably H, F, $CH_3$ or $OCH_3$; and
$R^{308c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(═O)—$CH_3$, C(═O)—$C_2H_5$, C(═O)—O—$CH_3$, C(═O)—O—$C_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(═O)—$CH_3$, C(═O)—$C_2H_5$, C(═O)—O—$CH_3$ and C(═O)—O—$C_2H_5$, preferably with at least one substituent selected from the group consisting of F, Cl, $CH_3$, O—$CH_3$, $CF_3$ and $OCF_3$,
$R^{302}$ is selected from the group consisting of H; F; Cl; $CF_3$; $CH_3$; $C_2H_5$, iso-propyl; cyclopropyl; and O—$CH_3$,
$R^{303}$, $R^{304}$, $R^{305}$ and $R^{306}$ are each independently of one another selected from the group consisting of H; F; Cl; $CF_3$; CN; $OCF_3$ and $NO_2$;
on the condition that at least one of $R^{303}$, $R^{304}$, $R^{305}$ and $R^{306}$ is H,
$R^{307}$ denotes a $C_{1-6}$-aliphatic residue, unsubstituted or mono- or polysubstituted with at least one substituent selected from the group consisting of F, Cl, OH, and O-methyl, preferably unsubstituted or mono- or polysubstituted with at least one substituent selected from the group consisting of F, Cl, and O-methyl, more preferably unsubstituted or mono- or polysubstituted with at least one substituent selected from the group consisting of F and O-methyl,
$R^{308}$ denotes H, methyl, ethyl, n-propyl, 2-propyl, n-butyl, isobutyl, sec.-butyl or tert.-butyl, preferably methyl or ethyl,
or
$R^{307}$ and $R^{308}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue, more preferably unsubstituted or mono- or polysubstituted with at least one substituent selected from the group consisting of F, Cl and a O—$C_{1-4}$ aliphatic residue, preferably O-methyl.

Another embodiment of the present invention therefore relates to a compound of general formula (I), wherein the compound is selected from a compound according to general formula (4-I),

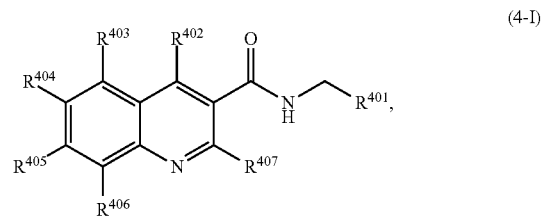

(4-I)

wherein
$R^{401}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted,
$R^{402}$ represents H; F; Cl; Br; I; CN; $CF_3$; C(═O)H; $NO_2$; $OCF_3$; $SCF_3$; a $C_{1-4}$-aliphatic residue, a C(═O)—$C_{1-4}$ aliphatic residue, a C(═O)—O—$C_{1-4}$ aliphatic residue, a C(═O)—NH—$C_{1-4}$ aliphatic residue, a C(═O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(═O)—$C_{1-4}$-aliphatic residue, a S—$C_{1-4}$-aliphatic residue, a S(═O)$_2$—$C_{1-4}$-aliphatic residue, a S(═O)$_2$—O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted,
$R^{403}$, $R^{404}$, $R^{405}$ and $R^{406}$ each independently of one another represent H; F; Cl; Br; I; CN; $CF_3$; C(═O)H; C(═O)—OH; C(═O)—$NH_2$; $SCF_3$; S(═O)$_2$—OH; $NO_2$; $OCF_3$; a $C_{1-4}$-aliphatic residue, a C(═O)—$C_{1-4}$ aliphatic residue, a C(═O)—O—$C_{1-4}$ aliphatic residue, a C(═O)—NH—$C_{1-4}$ aliphatic residue, a C(═O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(═O)—$C_{1-4}$-aliphatic residue, a S—$C_{1-4}$-aliphatic residue, a S(═O)$_2$—$C_{1-4}$-aliphatic residue, a S(═O)$_2$—O—$C_{1-4}$-aliphatic residue, wherein the $C_{1-4}$ aliphatic residue may be in each case be unsubstituted or mono- or polysubstituted; a NH($C_{1-4}$ aliphatic residue), a N($C_{1-4}$ aliphatic residue)$_2$, a NH—C(═O)—$C_{1-4}$ aliphatic residue, a NH—S(═O)$_2$—$C_{1-4}$-aliphatic residue, a N($C_{1-4}$ aliphatic residue)-C(═O)—$C_{1-4}$ aliphatic residue, or a N($C_{1-4}$ aliphatic residue)-S(═O)$_2$—$C_{1-4}$ aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted; on the condition that at least one of $R^{403}R^{404}$, $R^{405}$ and $R^{406}$ is ≠H, $R^{407}$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{407}$ denotes a 3 to 10 membered heterocycloaliphatic residue, the binding is carried out via a carbon atom of the 3 to 10 membered heterocycloaliphatic residue, in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a $NH—C(=O)—C_{1-4}$ aliphatic residue, a $NH—S(=O)_2—C_{1-4}$ aliphatic residue, =O, OH, $OCF_3$, a $O—C_{1-4}$-aliphatic residue, a $O—C(=O)—C_{1-4}$-aliphatic residue, SH, $SCF_3$, a $S—C_{1-4}$-aliphatic residue, $S(=O)_2OH$, a $S(=O)_2—C_{1-4}$-aliphatic residue, a $S(=O)_2—O—C_{1-4}$-aliphatic residue, a $S(=O)_2—NH—C_{1-4}$-aliphatic residue, CN, $CF_3$, CHO, COOH, a $C_{1-4}$-aliphatic residue, a $C(=O)—C_{1-4}$-aliphatic residue, a $C(=O)—O—C_{1-4}$-aliphatic residue, a $C_{3-6}$-cycloaliphatic residue, a 3 to 6 membered heterocycloaliphatic residue, $C(=O)—NH_2$, a $C(=O)—NH(C_{1-4}$ aliphatic residue), and a $C(=O)—N(C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a $NH—C(=O)—C_{1-4}$ aliphatic residue, a $NH—S(=O)_2—C_{1-4}$ aliphatic residue, =O, OH, $OCF_3$, a $O—C_{1-4}$-aliphatic residue, a $O—C(=O)—C_{1-4}$-aliphatic residue, SH, $SCF_3$, a $S—C_{1-4}$-aliphatic residue, $S(=O)_2OH$, a $S(=O)_2—C_{1-4}$-aliphatic residue, a $S(=O)_2—O—C_{1-4}$-aliphatic residue, a $S(=O)_2—NH—C_{1-4}$-aliphatic residue, CN, $CF_3$, CHO, COOH, a $C_{1-4}$-aliphatic residue, a $C(=O)—C_{1-4}$-aliphatic residue, a $C(=O)—O—C_{1-4}$-aliphatic residue, a $C_{3-6}$-cycloaliphatic residue, a 3 to 6 membered heterocycloaliphatic residue, $C(=O)—NH_2$, a $C(=O)—NH(C_{1-4}$ aliphatic residue), and a $C(=O)—N(C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

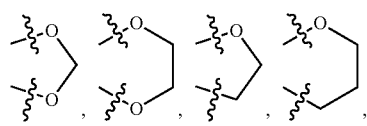

an $NH(C_{1-4}$ aliphatic residue), an $N(C_{1-4}$ aliphatic residue)$_2$, an $NH—C(=O)—C_{1-4}$ aliphatic residue, OH, $OCF_3$, a $O—C_{1-4}$-aliphatic residue, a $O—C(=O)—C_{1-4}$-aliphatic residue, SH, $SCF_3$, a $S—C_{1-4}$-aliphatic residue, $S(=O)_2OH$, a $S(=O)_2—C_{1-4}$-aliphatic residue, a $S(=O)_2—O—C_{1-4}$-aliphatic residue, a $S(=O)_2—NH—C_{1-4}$-aliphatic residue, CN, $CF_3$, $C(=O)H$, $C(=O)OH$, a $C_{1-4}$-aliphatic residue, a $C(=O)—C_{1-4}$-aliphatic residue, a $C(=O)—O—C_{1-4}$-aliphatic residue, a $C_{3-6}$-cycloaliphatic residue, a 3 to 6 membered heterocycloaliphatic residue, benzyl, aryl, heteroaryl, $C(=O)—NH_2$, a $C(=O)—NH(C_{1-4}$ aliphatic residue), and a $C(=O)—N(C_{1-4}$ aliphatic residue)$_2$.

The compounds according to general formula (4-I) are known from WO 2012/205238 A1, which is fully included by reference.

Preferred embodiments of the compound according to general formula (I) have general formulae (4-Ia), (4-Ib), (4-Ic) or (4-Id),

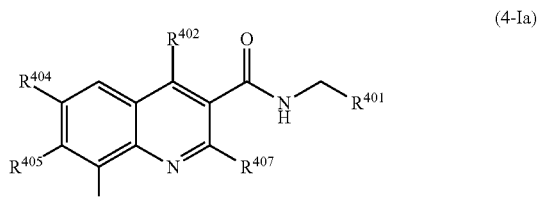

(4-Ia)

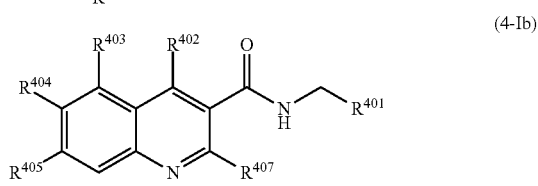

(4-Ib)

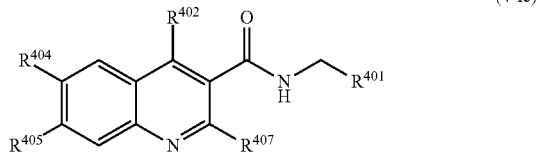

(4-Ic)

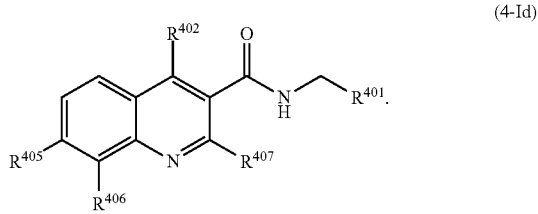

(4-Id)

Another preferred embodiment of present invention is a compound according to general formula (4-I), wherein $R^{401}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an $O—C_{1-4}$-aliphatic residue, $OCF_3$, SH, $SCF_3$, a $S—C_{1-4}$-aliphatic residue, $CF_3$, CN, a $C_{1-4}$-aliphatic residue and $C(=O)—OH$, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted $O—C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C($=$O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C($=$O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C($=$O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C($=$O)—OH, C($=$O)—$CH_3$, C($=$O)—$C_2H_5$, C($=$O)—O—$CH_3$ and C($=$O)—O—$C_2H_5$, a $C_{3-6}$ cycloaliphatic residue, a 3 to 6 membered heterocycloaliphatic residue,

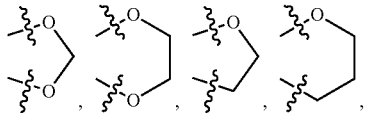

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C($=$O)—OH, C($=$O)—$CH_3$, C($=$O)—$C_2H_5$, C($=$O)—O—$CH_3$ and C($=$O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C($=$O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, $=$O, an O—$C_{1-4}$ aliphatic residue, $OCF_3$, SH, $SCF_3$, a S—$C_{1-4}$ aliphatic residue, $CF_3$, CN and C($=$O)—OH, $R^{402}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted, preferably represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, $=$O, OH, and an unsubstituted O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, $=$O, OH, a $C_{1-4}$-aliphatic residue and an O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, $=$O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, $=$O, OH, an unsubstituted $C_{1-4}$-aliphatic residue and an unsubstituted O—$C_{1-4}$-aliphatic residue, $R^{403}$, $R^{404}$, $R^{405}$ and $R^{406}$ each independently of one another represent H; F; Cl; Br; I; CN; $CF_3$; $OCF_3$; $SCF_3$; C($=$O)H; C($=$O)—OH; C($=$O)—$NH_2$; S($=$O)$_2$—OH; $NO_2$; a $C_{1-4}$-aliphatic residue, a C($=$O)—$C_{1-4}$ aliphatic residue, a C($=$O)—O—$C_{1-4}$ aliphatic residue, a C($=$O)—NH—$C_{1-4}$ aliphatic residue, a C($=$O)—N($C_{1-4}$ aliphatic residue)$_2$, a O—$C_{1-4}$-aliphatic residue, a O—C($=$O)—$C_{1-4}$-aliphatic residue, a S—$C_{1-4}$-aliphatic residue, a S($=$O)$_2$—$C_{1-4}$-aliphatic residue, a $NH(C_{1-4}$ aliphatic residue), a $N(C_{1-4}$ aliphatic residue)$_2$, a NH—C($=$O)—$C_{1-4}$ aliphatic residue, and a NH—S($=$O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, on the condition that at least one of $R^{403}$, $R^{404}$, $R^{405}$ and $R^{406}$ is ≠H, $R^{407}$ denotes a $C_{2-10}$-aliphatic residue, preferably a $C_{2-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{407}$ denotes a 3 to 10 membered heterocycloaliphatic residue, the 3 to 10 membered heterocycloaliphatic residue is linked via a carbon atom.

In a preferred embodiment of the compound according to general formula (4-I), the residue $R^{401}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

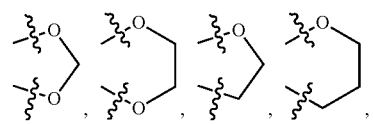

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and C(=O)—OH.

In a further preferred embodiment of the compound according to general formula (4-I), the residue $R^{401}$ represents the partial structure (4-T1)

wherein
m4 denotes 0, 1, 2, 3 or 4, preferably denotes 0, 1, or 2,
$R^{408a}$ and $R^{408b}$ each independently of one another represent H, F, Cl, Br, I, $NO_2$, $NH_2$, a $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH, or together denote =O,
preferably each independently of one another represent H, F, Cl, Br, I, $NH_2$, a $NH(C_{1-4}$ aliphatic residue), a $N(C_{1-4}$ aliphatic residue)$_2$, OH, O—$C_{1-4}$ aliphatic residue or a $C_{1-4}$ aliphatic residue,
more preferably each independently of one another represent H, F, Cl, Br, I, an O—$C_{1-4}$ aliphatic residue or a $C_{1-4}$ aliphatic residue,
even more preferably each independently of one another represent H, F, an O—$C_{1-4}$ aliphatic residue or a $C_{1-4}$ aliphatic residue, and
$R^{408c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes a $C_{3-10}$-cycloaliphatic residue or a 3 to 10 membered heterocycloaliphatic residue, preferably when m4 is ≠0, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes—preferably when m is =0—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

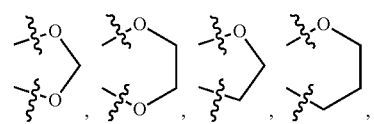

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.
Preferably,
$R^{401}$ represents the partial structure (4-T1),
wherein
m4 denotes 0, 1, or 2,
$R^{408a}$ and $R^{408b}$ each independently of one another represent H, F, Cl, Br, I, an O—$C_{1-4}$ aliphatic residue or a $C_{1-4}$ aliphatic residue,
preferably each independently of one another represent H, F, a O—$C_{1-2}$ aliphatic residue or a $C_{1-2}$ aliphatic residue, and
$R^{408c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue, C(=O)—OH, a $C_{3-6}$ cycloaliphatic residue, and a 3 to 6 membered heterocycloaliphatic residue,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH,
or denotes—preferably when m4 is =0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl or oxazolyl,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$,
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$ a $C_{1-4}$-aliphatic residue and C(=O)—OH.

More preferably,
$R^{401}$ represents the partial structure (4-T1),
wherein
m4 denotes 0, 1, or 2,
$R^{408a}$ and $R^{408b}$ each independently of one another represent H, F, Cl, Br, I, an O—$C_{1-4}$ aliphatic residue or a $C_{1-4}$ aliphatic residue,
preferably each independently of one another represent H, F, a O—$C_{1-2}$ aliphatic residue or a $C_{1-2}$ aliphatic residue, and
$R^{408c}$ denotes a $C_{1-4}$ aliphatic residue, unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue,
  wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue,
  wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue,
or denotes—preferably when m4 is =0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl,
  wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$ a $C_{1-4}$-aliphatic residue and C(=O)—OH.

In a further preferred embodiment of the compound according to general formula (4-I), the residue
$R^{401}$ represents the partial structure (4-T1),
wherein
m4 is 0, 1 or 2 and
$R^{408a}$ and $R^{408b}$ each independently of one another represent H, F, a O—$C_{1-4}$ aliphatic residue or a $C_{1-4}$ aliphatic residue; preferably H, F, $CH_3$ or $OCH_3$;
$R^{408c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or
wherein
m4 is 0,
$R^{408a}$ and $R^{408b}$ each independently of one another represent H, F, a O—$C_{1-4}$ aliphatic residue or a $C_{1-4}$ aliphatic residue; preferably H, F, $CH_3$ or $OCH_3$; and
$R^{408c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$.

Particularly preferred is a compound according to general formula (4-I) which has the following general formula (4-Ie),

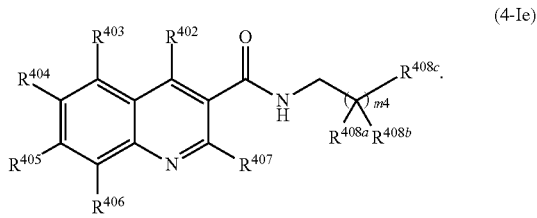
(4-Ie)

In a preferred embodiment of the compound according to general formula (4-I), the residue
$R^{402}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted.

Preferably,
$R^{402}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue,
wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue,
a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue,
wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably,
$R^{402}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue,
wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue,
cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue,
and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably,
$R^{402}$ represents H; F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, and cyclohexyl.

Still more preferably,
$R^{402}$ is selected from the group consisting of H; F; Cl; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$.

In particular,
$R^{402}$ is selected from the group consisting of H; F; Cl; $CF_3$; $CH_3$; $C_2H_5$, iso-propyl; cyclopropyl; and O—$CH_3$; preferably selected from the group consisting of H; F; Cl; $CF_3$; $CH_3$; and O—$CH_3$.

In a particular preferred embodiment of the compound according to general formula (4-I), the residue
$R^{402}$ is ≠H.

In a preferred embodiment of the compound according to general formula (4-I), the residues
$R^{403}$, $R^{404}$, $R^{405}$ and $R^{406}$ each independently of one another represent H; F; Cl; Br; I; CN; $CF_3$; $OCF_3$; $SCF_3$; C(=O)H; C(=O)—OH; C(=O)—$NH_2$; $S(=O)_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—$S(=O)_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—C$_{1-4}$-aliphatic residue; a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and a O—C$_{1-4}$-aliphatic residue, and in each case optionally bridged via an unsubstituted C$_{1-4}$ aliphatic group, on the condition that at least one of R$^{403}$, R$^{404}$, R$^{405}$ and R$^{406}$ is ≠H.

Preferably,

R$^{403}$, R$^{404}$, R$^{405}$ and R$^{406}$ each independently of one another represent H; F; Cl; Br; I; CN; CF$_3$; OCF$_3$; SCF$_3$; C(=O)H; C(=O)—OH; C(=O)—NH$_2$; S(=O)$_2$—OH; NO$_2$; a C$_{1-4}$-aliphatic residue, a C(=O)—C$_{1-4}$ aliphatic residue, a C(=O)—O—C$_{1-4}$ aliphatic residue, a O—C$_{1-4}$-aliphatic residue, a O—C(=O)—C$_{1-4}$-aliphatic residue, a S—C$_{1-4}$-aliphatic residue, a S(=O)$_2$—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and a O—C$_{1-4}$-aliphatic residue; a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and a O—C$_{1-4}$-aliphatic residue, and in each case optionally bridged via an unsubstituted C$_{1-4}$ aliphatic group, on the condition that at least one of R$^{403}$ R$^{404}$, R$^{405}$ and R$^{406}$ is ≠H.

More preferably,

R$^{403}$, R$^{404}$, R$^{405}$ and R$^{406}$ each independently of one another represent H; F; Cl; Br; I; CN; CF$_3$; OCF$_3$; SCF$_3$; C(=O)H; NO$_2$; a C$_{1-4}$-aliphatic residue, a C(=O)—C$_{1-4}$ aliphatic residue, a C(=O)—O—C$_{1-4}$ aliphatic residue, a O—C$_{1-4}$-aliphatic residue, a S—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and a O—C$_{1-4}$-aliphatic residue; a C$_{3-6}$-cycloaliphatic residue, unsubstituted or mono- or polysubstituted with at least one substituent selected from the group consisting of F, Cl, Br, I, =O, OH, a C$_{1-4}$-aliphatic residue and a O—C$_{1-4}$-aliphatic residue, and in each case optionally bridged via an unsubstituted C$_{1-4}$ aliphatic group, on the condition that at least one of R$^{403}$, R$^{404}$, R$^{405}$ and R$^{406}$ is ≠H.

In a further preferred embodiment of the present invention R$^{403}$, R$^{404}$, R$^{405}$ and R$^{406}$ each independently of one another are selected from the group consisting of H; F; Cl; Br; I; NO$_2$; CF$_3$; CN; OCF$_3$; SCF$_3$; a (C=O)—C$_{1-4}$aliphatic residue, a C$_{1-4}$aliphatic residue, O—C$_{1-4}$aliphatic residue, a S—C$_{1-4}$aliphatic residue, wherein the C$_{1-4}$-aliphatic residue in each case may be unsubstituted or mono- or polysubstituted with at least one substituent selected from the group consisting of F, Cl, and O—CH$_3$;

on the condition that at least one of R$^{403}$, R$^{404}$, R$^{405}$ and R$^{406}$ is ≠H.

Preferably,

R$^{403}$, R$^{404}$, R$^{405}$ and R$^{406}$ each independently of one another are selected from the group consisting of H; F; Cl; Br; I; NO$_2$; CF$_3$; CN; OCF$_3$; SCF$_3$; methyl; ethyl; n-propyl; iso-propyl; n-butyl; sec.-butyl; tert.-butyl; cyclopropyl; C(=O)-methyl; C(=O)-ethyl; (C=O)-isopropyl; (C=O)-t-butyl; O-methyl; O-ethyl; O-isopropyl; O-t-butyl; O—(CH$_2$)$_2$—O—CH$_3$; S-Methyl; S-Ethyl;

on the condition that at least one of R$^{403}$, R$^{404}$, R$^{405}$ and R$^{406}$ is ≠H.

In particular,

R$^{403}$, R$^{404}$, R$^{405}$ and R$^{406}$ are each independently of one another are selected from the group consisting of H; F; Cl; Br; I; NO$_2$; CF$_3$; CN; (C=O)-methyl; (C=O)-ethyl; (C=O)-isopropyl; (C=O)-t-butyl; methyl; ethyl; isopropyl; t-butyl; O-methyl; O-Ethyl; O-isopropyl; O-t-butyl; OCF$_3$; S-methyl; S-ethyl; and SCF$_3$;

on the condition that at least one of R$^{403}$, R$^{404}$, R$^{405}$ and R$^{406}$ is ≠H.

More particularly,

R$^{403}$, R$^{404}$, R$^{405}$ and R$^{406}$ are each independently of one another selected from the group consisting of H; F; Cl; Br; CH$_3$; CF$_3$; CN; OCF$_3$ and NO$_2$;

on the condition that at least one of R$^{403}$, R$^{404}$, R$^{405}$ and R$^{406}$ is ≠H.

Most preferred,

R$^{403}$, R$^{404}$ and R$^{406}$ each independently are selected from the group consisting of H and F;

and

R$^{405}$ denotes F; Cl; Br; CH$_3$; CF$_3$; OCF$_3$; CN; or NO$_2$; preferably denotes F, Br, CF$_3$ or CN.

In a particular preferred embodiment of the compound according to general formula (4-I) at least one of the residues R$^{403}$, R$^{404}$, R$^{405}$ and R$^{406}$ is ≠H.

In a preferred embodiment of the compound according to general formula (4-I), the residue R$^{407}$ denotes a C$_{2-10}$-aliphatic residue, preferably a C$_{2-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue, a C(=O)—O—C$_{1-4}$-aliphatic residue, and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C(=O)—O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{407}$ denotes a 3 to 10 membered heterocycloaliphatic residue, the 3 to 10 membered heterocycloaliphatic residue is linked via a carbon atom.

In a further preferred embodiment of the compound according to general formula (4-I), the residue $R^{407}$ denotes a $C_{2-10}$-aliphatic residue, preferably a $C_{2-8}$-aliphatic residue, unsubstituted or mono- or polysubstituted with at least one substituent selected from the group consisting of F, Cl, Br, I, $NO_2$, a $NH(C_{1-4}$ aliphatic residue), a $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, CN, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, and a $C_{1-4}$-aliphatic residue.

on the condition that if $R^{407}$ denotes a 3 to 10 membered heterocycloaliphatic residue, the 3 to 10 membered heterocycloaliphatic residue is linked via a carbon atom.

Preferably, $R^{407}$ denotes a $C_{2-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, a $NH(C_{1-4}$ aliphatic residue), a $N(C_{1-4}$ aliphatic residue)$_2$, SH, $SCF_3$, a S—$C_{1-4}$-aliphatic residue, a C(=O)—O—$C_{1-4}$-aliphatic residue, $CF_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a C(=O)—O—$C_{1-4}$ aliphatic residue, a S—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue.

on the condition that if $R^{407}$ denotes a 3 to 10 membered heterocycloaliphatic residue, the 3 to 10 membered heterocycloaliphatic residue is linked via a carbon atom.

More preferably, $R^{407}$ denotes a $C_{2-8}$-aliphatic residue, preferably a $C_{2-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, a $NH(C_{1-4}$ aliphatic residue), a $N(C_{1-4}$ aliphatic residue)$_2$, SH, $SCF_3$, a S—$C_{1-4}$-aliphatic residue, $CF_3$, a C(=O)—O—$C_{1-4}$-aliphatic residue, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue, on the condition that if $R^{407}$ denotes a 3 to 10 membered heterocycloaliphatic residue, the 3 to 10 membered heterocycloaliphatic residue is linked via a carbon atom.

Even more preferably, $R^{407}$ denotes a $C_{2-8}$-aliphatic residue, preferably a $C_{2-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, an $NH(C_{1-4}$ aliphatic residue), an $N(C_{1-4}$ aliphatic residue)$_2$, SH, $SCF_3$, a S—$C_{1-4}$-aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $CF_3$ and an unsubstituted $O$—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an $O$—$C_{1-4}$ aliphatic residue, $OCF_3$, $SCF_3$, a $S$—$C_{1-4}$ aliphatic residue, a $C(=O)$—$O$—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted $O$—$C_{1-4}$-aliphatic residue, and wherein the $C_{3-10}$-cycloaliphatic residue or the 3 to 10 membered heterocycloaliphatic residue may in each case optionally bridged via a unsubstituted $C_{1-8}$ aliphatic group, preferably an unsubstituted $C_{1-4}$ aliphatic group, on the condition that if $R^{407}$ denotes a 3 to 10 membered heterocycloaliphatic residue, the 3 to 10 membered heterocycloaliphatic residue is linked via a carbon atom.

Still more preferably, $R^{407}$ denotes a $C_{2-6}$-aliphatic residue, unsubstituted or mono- or polysubstituted with at least one substituent selected from the group consisting of F, Cl, Br, I, OH, =O, an $O$—$C_{1-4}$-aliphatic residue, an $NH(C_{1-4}$ aliphatic residue), an $N(C_{1-4}$ aliphatic residue$)_2$, a $C(=O)$—$O$—$C_{1-4}$-aliphatic residue, $OCF_3$, SH, $SCF_3$, a $S$—$C_{1-4}$-aliphatic residue, $CF_3$, and a $C_{1-4}$-aliphatic residue, wherein the $C_{1-4}$-aliphatic residue in each case is unsubstituted, or denotes a $C_{3-10}$-cycloaliphatic residue, preferably a $C_{3-6}$-cycloaliphatic residue, or a 3 to 10 membered heterocycloaliphatic residue, preferably a 3 to 6 membered heterocycloaliphatic residue, in each case unsubstituted or mono- or polysubstituted with at least one substituent selected from the group consisting of F, Cl, Br, I, OH, =O, an $O$—$C_{1-4}$ aliphatic residue, $OCF_3$, $SCF_3$, a $S$—$C_{1-4}$ aliphatic residue, a $C(=O)$—$O$—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with OH or an unsubstituted $O$—$C_{1-4}$-aliphatic residue, and wherein the $C_{3-10}$-cycloaliphatic residue or the 3 to 10 membered heterocycloaliphatic residue may in each case optionally bridged via a unsubstituted $C_{1-4}$ aliphatic group, on the condition that if $R^{407}$ denotes a 3 to 10 membered heterocycloaliphatic residue, the 3 to 10 membered heterocycloaliphatic residue is linked via a carbon atom.

In particular, $R^{407}$ denotes a $C_{2-6}$-aliphatic residue, preferably selected from the group consisting of ethyl, n-propyl, 2-propyl, n-butyl, isobutyl, sec.-butyl, tert.-butyl, n-pentyl, isopentyl, neopentyl, n-hexyl, ethenyl and propenyl ($-CH_2CH=CH_2$, $-CH=CH-CH_3$, $-C(=CH_2)-CH_3$), unsubstituted or mono- or polysubstituted with at least one substituent selected from the group consisting of F, Cl, Br, I, OH, =O, an $O$—$C_{1-4}$-aliphatic residue, an $NH(C_{1-4}$ aliphatic residue), an $N(C_{1-4}$ aliphatic residue$)_2$, a $C(=O)$—$O$—$C_{1-4}$-aliphatic residue, $OCF_3$, SH, $SCF_3$, a $S$—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, OH, an $O$—$C_{1-4}$-aliphatic residue, an $NH(C_{1-4}$ aliphatic residue), an $N(C_{1-4}$ aliphatic residue$)_2$, $CF_3$, and a $C_{1-4}$-aliphatic residue, more preferably in each case unsubstituted or mono- or polysubstituted with at least one substituent selected from the group consisting of F, Cl, OH, an $O$—$C_{1-4}$-aliphatic residue and an $N(C_{1-4}$ aliphatic residue$)_2$, even more preferably in each case unsubstituted or mono- or polysubstituted with at least one substituent selected from the group consisting of O-methyl, OH and $N(methyl)_2$, wherein the $C_{1-4}$-aliphatic residue in each case is unsubstituted, or denotes a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of piperidinyl (preferably piperidin-4-yl or piperidin-3-yl), tetrahydrofuranyl, and tetrahydropyranyl, in each case unsubstituted or mono- or polysubstituted with at least one substituent selected from the group consisting of F, Cl, Br, I, OH, =O, an $O$—$C_{1-4}$-aliphatic residue, a $C(=O)$—$O$—$C_{1-4}$-aliphatic residue, $OCF_3$, SH, $SCF_3$, a $S$—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, OH, an $O$—$C_{1-4}$-aliphatic residue, $CF_3$, and a $C_{1-4}$-aliphatic residue, more preferably in each case unsubstituted or mono- or polysubstituted with at least one substituent selected from the group consisting of F, Cl, and an $O$—$C_{1-4}$-aliphatic residue, preferably O-methyl, wherein the $C_{1-4}$-aliphatic residue in each case is unsubstituted, and wherein the $C_{3-6}$-cycloaliphatic residue or the 3 to 6 membered heterocycloaliphatic residue may in each case optionally bridged via an unsubstituted $C_{1-4}$ aliphatic group, preferably via an unsubstituted $C_{1-2}$ aliphatic group, on the condition that if $R^{407}$ denotes a 3 to 6 membered heterocycloaliphatic residue, the 3 to 6 membered heterocycloaliphatic residue is linked via a carbon atom.

Most preferred, $R^{407}$ denotes ethyl, n-propyl, 2-propyl, n-butyl, isobutyl, sec.-butyl, tert.-butyl, n-pentyl, isopentyl, neopentyl, n-hexyl, ethenyl or propenyl ($-CH_2CH=CH_2$, $-CH=CH-CH_3$, $-C(=CH_2)-CH_3$), in each case unsubstituted or mono- or polysubstituted with at least one substituent selected from the group consisting of F, Cl, OH, $O$—$CH_3$, $CF_3$, and $N(CH_3)_2$, preferably in each case unsubstituted or mono- or polysubstituted with at least one substituent selected from the group consisting of F, Cl, OH, $O$—$CH_3$, and $N(CH_3)_2$, more preferably in each case unsubstituted or mono- or polysubstituted with at least one substituent selected from the group consisting of $O$—$CH_3$, OH and $N(CH_3)_2$, or denotes cyclopropyl, cyclobutyl, cyclopentyl and cyclohexyl, piperidinyl (preferably piperidin-4-yl or piperidin-3-yl), tetrahydrofuranyl, or tetrahydropyranyl, in each case unsubstituted or mono- or polysubstituted with at least one substituent selected from the group consisting of F, Cl, OH, an $O$—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an $O$—$C_{1-4}$-aliphatic residue, preferably O-methyl, wherein the $C_{1-4}$-aliphatic residue in each case is unsubstituted, and wherein cyclopropyl, cyclobutyl, cyclopentyl and cyclohexyl, piperidinyl (preferably piperidin-4-yl or piperidin-3-yl), tetrahydrofuranyl, and tetrahydropyranyl may in each case be optionally bridged, preferably are bridged, via an unsubstituted $C_{1-4}$ aliphatic group, preferably via an unsubstituted $C_{1-2}$ aliphatic group, on the condition that if $R^{407}$ denotes piperidinyl tetrahydrofuranyl, or tetrahydropyranyl, piperidinyl tetrahydrofuranyl, or tetrahydropyranyl, each of these residues is linked via a carbon atom.

Particularly preferred is also a compound according to general formula (4-I), wherein $R^{401}$ represents the partial structure (4-T1),

(4-T1), wherein m4 is 0, 1 or 2 and $R^{408a}$ and $R^{408b}$ each independently of one another represent H, F, a O—$C_{1-4}$ aliphatic residue or a $C_{1-4}$ aliphatic residue; preferably H, F, $CH_3$ or $OCH_3$;

$R^{408c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or wherein m4 is 0, $R^{408a}$ and $R^{408b}$ each independently of one another represent H, F, a O—$C_{1-4}$ aliphatic residue or a $C_{1-4}$ aliphatic residue; preferably H, F, $CH_3$ or $OCH_3$; and $R^{408c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, $C(=O)$—$CH_3$, $C(=O)$—$C_2H_5$, $C(=O)$—$O$—$CH_3$, $C(=O)$—$O$—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, $C(=O)$—$CH_3$, $C(=O)$—$C_2H_5$, $C(=O)$—$O$—$CH_3$ and $C(=O)$—$O$—$C_2H_5$, preferably with at least one substituent selected from the group consisting of F, Cl, $CH_3$, O—$CH_3$, $CF_3$ and $OCF_3$, $R^{402}$ is selected from the group consisting of H; F; Cl; $CF_3$; $CH_3$; $C_2H_5$, iso-propyl; cyclopropyl; and O—$CH_3$, $R^{403}$, $R^{404}$, $R^{405}$ and $R^{406}$ are each independently of one another selected from the group consisting of H; F; Cl; $CF_3$; CN; $OCF_3$ and $NO_2$, on the condition that at least one of $R^{403}$, $R^{404}$, $R^{405}$ and $R^{406}$ is ≠H, $R^{407}$ denotes ethyl, n-propyl, 2-propyl, n-butyl, isobutyl, sec.-butyl, tert.-butyl, n-pentyl, isopentyl, neopentyl, n-hexyl, ethenyl or propenyl (—$CH_2CH=CH_2$, —CH=CH—$CH_3$, —C(=$CH_2$)—$CH_3$), in each case unsubstituted or mono- or polysubstituted with at least one substituent selected from the group consisting of F, Cl, OH, O—$CH_3$, $CF_3$, and $N(CH_3)_2$, preferably in each case unsubstituted or mono- or polysubstituted with at least one substituent selected from the group consisting of F, Cl, OH, O—$CH_3$, and $N(CH_3)_2$, more preferably in each case unsubstituted or mono- or polysubstituted with at least one substituent selected from the group consisting of O—$CH_3$, OH and $N(CH_3)_2$, or denotes cyclopropyl, cyclobutyl, cyclopentyl and cyclohexyl, piperidinyl (preferably piperidin-4-yl or piperidin-3-yl), tetrahydrofuranyl, or tetrahydropyranyl, in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, preferably O-methyl, wherein the $C_{1-4}$-aliphatic residue in each case is unsubstituted, and wherein cyclopropyl, cyclobutyl, cyclopentyl and cyclohexyl, piperidinyl (preferably piperidin-4-yl or piperidin-3-yl), tetrahydrofuranyl, and tetrahydropyranyl may in each case be optionally bridged via an unsubstituted $C_{1-4}$ aliphatic group, preferably via an unsubstituted $C_{1-2}$ aliphatic group, on the condition that if $R^{407}$ denotes piperidinyl, tetrahydrofuranyl, or tetrahydropyranyl, each of these residues is linked via a carbon atom.

Another embodiment of the present invention therefore relates to a compound of general formula (I), wherein the compound is selected from a compound according to general formula (5-I).

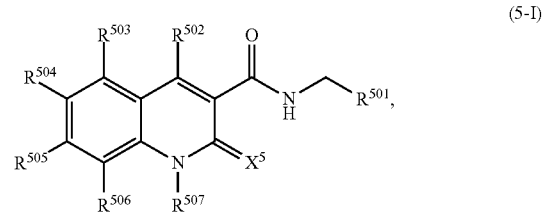

(5-I)

wherein $X^5$ denotes O or S, preferably O, $R^{501}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^{502}$ represents F; Cl; Br; I; CN; $CF_3$; $C(=O)H$; $NO_2$; $OCF_3$; $SCF_3$; a $C_{1-4}$-aliphatic residue, a $C(=O)$—$C_{1-4}$ aliphatic residue, a $C(=O)$—$O$—$C_{1-4}$ aliphatic residue, a $C(=O)$—$NH$—$C_{1-4}$ aliphatic residue, a $C(=O)$—$N(C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—$C(=O)$—$C_{1-4}$-aliphatic residue, a S—$C_{1-4}$-aliphatic residue, a $S(=O)_2$—$C_{1-4}$-aliphatic residue, a $S(=O)_2$—$O$—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{503}$, $R^{504}$, $R^{505}$ and $R^{506}$ each independently of one another represent H; F; Cl; Br; I; CN; $CF_3$; C(=O)H; C(=O)—OH; C(=O)—$NH_2$; $SCF_3$; S(=O)$_2$—OH; $NO_2$; $OCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may be in each case be unsubstituted or mono- or polysubstituted; a NH($C_{1-4}$ aliphatic residue), a N($C_{1-4}$ aliphatic residue)$_2$, a NH—C(=O)—$C_{1-4}$ aliphatic residue, a NH—S(=O)$_2$—$C_{1-4}$-aliphatic residue, a N($C_{1-4}$ aliphatic residue)-C(=O)—$C_{1-4}$ aliphatic residue, or a N($C_{1-4}$ aliphatic residue)-S(=O)$_2$—$C_{1-4}$ aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted; preferably on the condition that at least one of $R^{503}$, $R^{504}$, $R^{505}$ and $R^{506}$ is ≠H, $R^{507}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{507}$ denotes a 3 to 10 membered heterocycloaliphatic residue, the 3 to 10 membered heterocycloaliphatic residue is linked via a carbon atom, in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an NH($C_{1-4}$ aliphatic residue), a NH—C(=O)—$C_{1-4}$ aliphatic residue, a NH—S(=O)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

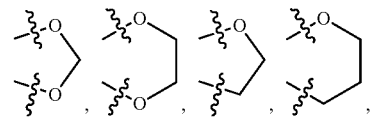

an NH($C_{1-4}$ aliphatic residue), an N($C_{1-4}$ aliphatic residue)$_2$, an NH—C(=O)—$C_{1-4}$ aliphatic residue, an NH—S(=O)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—$NH_2$, a C(=O)—NH($C_{1-4}$ aliphatic residue), and a C(=O)—N($C_{1-4}$ aliphatic residue)$_2$.

The compounds according to general formula (5-I) are known from WO 2012/025239 A1, which is fully included by reference.

Preferred embodiments of the compound according to general formula (5-I) have general formulae (5-I-I), and/or (5-I-II),

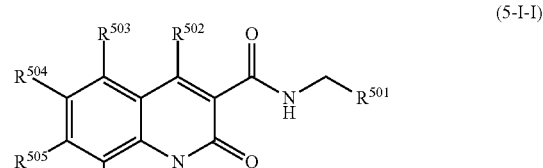

(5-I-I)

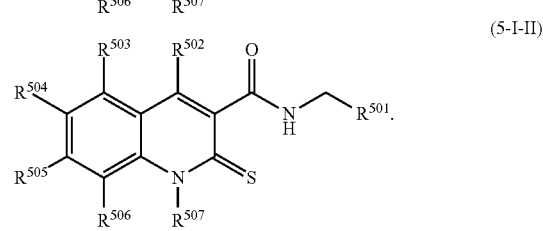

(5-I-II)

Particularly preferred is a compound according to general formula (5-I-I), i.e. a compound according to general formula (5-I), wherein $X^5$ denotes O.

Further preferred embodiments of the compound according to general formula (I) have general formulae (5-Ia), (5-Ib), (5-Ic) and/or (5-Id),

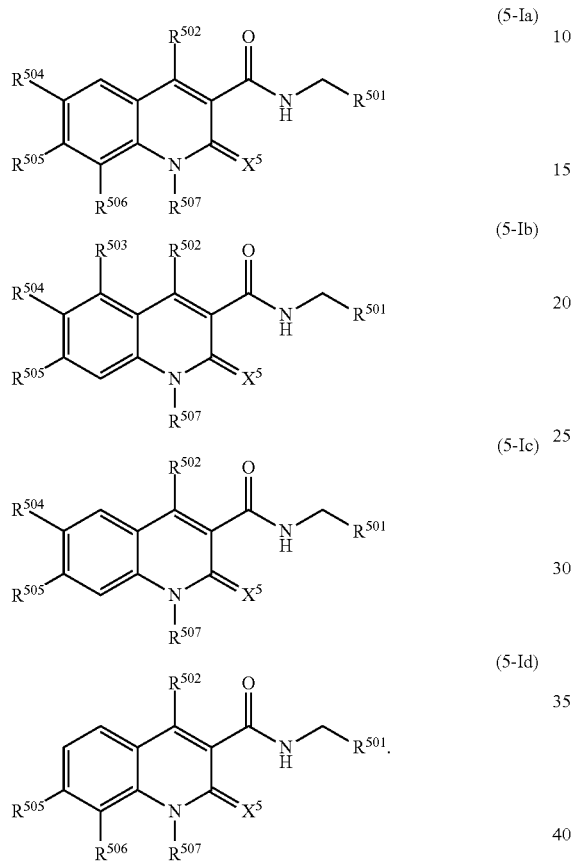

Another preferred embodiment of present invention is a compound according to general formula (5-I), wherein $R^{501}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), OH, an O—C$_{1-4}$-aliphatic residue, OCF$_3$, SH, SCF$_3$, a S—C$_{1-4}$-aliphatic residue, CF$_3$, CN, a $C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a $C_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a $C_{3-6}$ cycloaliphatic residue, a 3 to 6 membered heterocycloaliphatic residue,

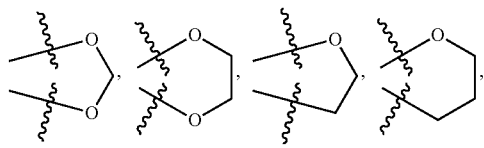

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a $C_{1-4}$-aliphatic residue, C(=O)—OH, C(=O)—CH$_3$, C(=O)—C$_2$H$_5$, C(=O)—O—CH$_3$ and C(=O)—O—C$_2$H$_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN and C(=O)—OH, $X^5$ represents O or S, $R^{502}$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted, preferably represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, OH, an unsubstituted $C_{1-4}$-aliphatic residue and an unsubstituted O—$C_{1-4}$-aliphatic residue, $R^{503}$, $R^{504}$, $R^{505}$ and $R^{506}$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{503}$, $R^{504}$, $R^{505}$ and $R^{506}$ is ≠H, $R^{507}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), OH, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{507}$ denotes a 3 to 10 membered heterocycloaliphatic residue, the 3 to 10 membered heterocycloaliphatic residue is linked via a carbon atom.

In a preferred embodiment of the compound according to general formula (5-I), the residue $R^{501}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), OH, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C($=$O)—OH, a $C_{3-6}$ cycloaliphatic residue, and a 3 to 6 membered heterocycloaliphatic residue,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein the $C_{3-6}$ cycloaliphatic residue and the 3 to 6 membered heterocycloaliphatic residue may in each case may be unsubstituted or mono- or poly-substituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C($=$O)—OH,
  and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C($=$O)—OH,
or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C($=$O)—OH, C($=$O)—$CH_3$, C($=$O)—$C_2H_5$, C($=$O)—O—$CH_3$ and C($=$O)—O—$C_2H_5$, a $C_{3-6}$ cycloaliphatic residue, a 3 to 6 membered heterocycloaliphatic residue,

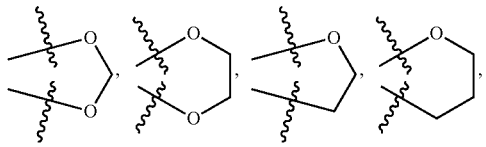

benzyl, phenyl, thienyl, pyridyl, furyl, thiazolyl and oxazolyl,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C($=$O)—OH, C($=$O)—$CH_3$, C($=$O)—$C_2H_5$, C($=$O)—O—$CH_3$ and C($=$O)—O—$C_2H_5$, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C($=$O)—OH,
  and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN and C($=$O)—OH.

In a further preferred embodiment of the compound according to general formula (5-I), the residue $R^{501}$ represents the partial structure (5-T1), $$-(CR^{508a}R^{508b})_{m5}-R^{508c} \qquad (5\text{-}T1),$$

wherein
m5 denotes 0, 1, 2, 3 or 4, preferably denotes 0, 1, or 2,
$R^{508a}$ and $R^{508b}$ each independently of one another represent H, F, Cl, Br, I, $NO_2$, $NH_2$, a $NH(C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C($=$O)—OH,
  preferably each independently of one another represent H, F, Cl, Br, I, $NH_2$, a $NH(C_{1-4}$ aliphatic residue), OH, O—$C_{1-4}$ aliphatic residue or a $C_{1-4}$ aliphatic residue,
  more preferably each independently of one another represent H, F, Cl, Br, I, an O—$C_{1-4}$ aliphatic residue or a $C_{1-4}$ aliphatic residue,
  even more preferably each independently of one another represent H, F, an O—$C_{1-4}$ aliphatic residue or a $C_{1-4}$ aliphatic residue, and
$R^{508c}$ denotes a $C_{1-4}$ aliphatic residue, unsubstituted or mono- or polysubstituted with at least one substituent selected from the group consisting of F, Cl, Br, I, $NO_2$, $NH_2$, an $NH(C_{1-4}$ aliphatic residue), OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C($=$O)—OH,
  or denotes a $C_{3-10}$-cycloaliphatic residue or a 3 to 10 membered heterocycloaliphatic residue, preferably when m is $\neq$0, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, $=$O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C($=$O)—OH, a $C_{3-6}$ cycloaliphatic residue and a 3 to 6 membered heterocycloaliphatic residue,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes—preferably when m5 is =0—an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

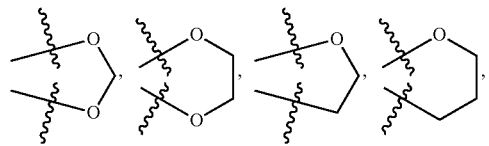

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

Preferably,

R$^{501}$ represents the partial structure (5-T1), wherein m5 denotes 0, 1, or 2, R$^{508a}$ and R$^{508b}$ each independently of one another represent H, F, Cl, Br, I, an O—C$_{1-4}$ aliphatic residue or a C$_{1-4}$ aliphatic residue, preferably each independently of one another represent H, F, a O—C$_{1-2}$ aliphatic residue or a C$_{1-2}$ aliphatic residue, and R$^{508c}$ denotes a C$_{1-4}$ aliphatic residue, unsubstituted or mono- or polysubstituted with at least one substituent selected from the group consisting of F, Cl, Br, I, OH, an O—C$_{1-4}$ aliphatic residue, OCF$_3$, CF$_3$, a C$_{1-4}$-aliphatic residue and C(=O)—OH, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$, a C$_{1-4}$-aliphatic residue and C(=O)—OH, or denotes—preferably when m5 is =0—an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl or oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$ a C$_{1-4}$-aliphatic residue and C(=O)—OH.

More preferably,

R$^{501}$ represents the partial structure (5-T1), wherein m5 denotes 0, 1, or 2, R$^{508a}$ and R$^{508b}$ each independently of one another represent H, F, Cl, Br, I, an O—C$_{1-4}$ aliphatic residue or a C$_{1-4}$ aliphatic residue, preferably each independently of one another represent H, F, a O—C$_{1-2}$ aliphatic residue or a C$_{1-2}$ aliphatic residue, and R$^{508c}$ denotes a C$_{1-4}$ aliphatic residue, unsubstituted or mono- or polysubstituted with at least one substituent selected from the group consisting of F, Cl, Br, I, an O—C$_{1-4}$ aliphatic residue, CF$_3$, and a C$_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes—preferably when m5 is =0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$ a $C_{1-4}$-aliphatic residue and C(=O)—OH.

In a further preferred embodiment of the compound according to general formula (5-I), the residue $R^{501}$ represents the partial structure (5-T1), wherein
m5 is 0, 1 or 2 and
$R^{508a}$ and $R^{508b}$ each independently of one another represent H, F, a O—$C_{1-4}$ aliphatic residue or a $C_{1-4}$ aliphatic residue; preferably H, F, $CH_3$ or $OCH_3$;

$R^{508c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or
wherein
m5 is 0,
$R^{508a}$ and $R^{508b}$ each independently of one another represent H, F, a O—$C_{1-4}$ aliphatic residue or a $C_{1-4}$ aliphatic residue; preferably H, F, $CH_3$ or $OCH_3$; and $R^{508c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$.

Particularly preferred is a compound according to general formula (5-I) which has the following general formula (5-Ie):

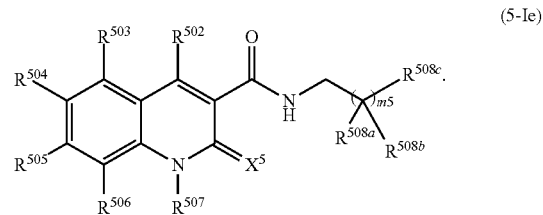

(5-Ie)

In particular,
$R^{501}$ represents aryl, preferably phenyl, or heteroaryl, preferably pyridyl or thienyl, in each case unsubstituted or mono- or disubstituted with at least one substituent selected from the group consisting of F, Cl, Br, I, OH, $OCH_3$, $OCF_3$, $CF_3$, CN, and $CH_3$, preferably represents phenyl, unsubstituted or mono- or disubstituted with at least one substituent selected from the group consisting of F, Cl, Br, I, OH, $OCH_3$, $OCF_3$, $CF_3$, CN, and $CH_3$, or represents an unsubstituted $C_{1-6}$-aliphatic residue.

In a further preferred embodiment of the compound according to general formula (5-I), the residue $X^5$ denotes O.

In another preferred embodiment of the compound according to general formula (5-I), the residue $X^5$ denotes S.

In a preferred embodiment of the compound according to general formula (5-I), the residue $R^{502}$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted. Preferably, $R^{502}$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue, a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue,
and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably,
$R^{502}$ represents F; Cl; Br; I; CN; $CF_3$; $NO_2$; $OCF_3$; $SCF_3$; a $C_{1-4}$-aliphatic residue, a S—$C_{1-4}$-aliphatic residue, or a O—$C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, and an unsubstituted O—$C_{1-4}$-aliphatic residue,
cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue,
and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably,
$R^{502}$ represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, and cyclohexyl.

Still more preferably,
$R^{502}$ is selected from the group consisting of F; Cl; Br; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$.

In particular,
$R^{502}$ is selected from the group consisting of F; Cl; Br; $CF_3$; $CH_3$; $C_2H_5$; iso-propyl; cyclopropyl; and O—$CH_3$.

In a preferred embodiment of the compound according to general formula (5-I), the residues
$R^{503}$, $R^{504}$, $R^{505}$ and $R^{506}$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{503}$, $R^{504}$, $R^{505}$ and $R^{506}$ is ≠H.

Preferably,
$R^{503}$, $R^{504}$, $R^{505}$ and $R^{506}$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group,
preferably on the condition that at least one of $R^{503}$, $R^{504}$, $R^{505}$ and $R^{506}$ is ≠H.

More preferably,
$R^{503}$, $R^{504}$, $R^{505}$ and $R^{506}$ each independently of one another represent H; F; Cl; Br; I; CN; $CF_3$; $OCF_3$; $SCF_3$; C(=O)H; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a S—$C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, and a O—$C_{1-4}$-aliphatic residue; a $C_{3-6}$-cycloaliphatic residue, unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group,
preferably on the condition that at least one of $R^{503}$, $R^{504}$, $R^{505}$ and $R^{506}$ is ≠H.

In a further preferred embodiment of the present invention
$R^{503}$, $R^{504}$, $R^{505}$ and $R^{506}$ each independently of one another are selected from the group consisting of H; F; Cl; Br; I; $NO_2$; $CF_3$; CN; $OCF_3$; $SCF_3$; a (C=O)—$C_{1-4}$aliphatic residue, a $C_{1-4}$aliphatic residue, O—$C_{1-4}$ aliphatic residue, a S—$C_{1-4}$aliphatic residue, wherein the $C_{1-4}$-aliphatic residue in each case may be unsubstituted or mono- or polysubstituted with at least one substituent selected from the group consisting of F, Cl, OH, and O—$CH_3$; preferably on the condition that at least one of $R^{503}$, $R^{504}$, $R^{505}$ and $R^{506}$ is ≠H.

Preferably,
$R^{503}$, $R^{504}$, $R^{505}$ and $R^{506}$ each independently of one another are selected from the group consisting of H; F; Cl; Br; I; $NO_2$; $CF_3$; CN; $OCF_3$; $SCF_3$; methyl; ethyl; n-propyl;

iso-propyl; n-butyl; sec.-butyl; tert-butyl; cyclopropyl; C(=O)-methyl; C(=O)-ethyl; (C=O)-isopropyl; (C=O)-t-butyl; O-methyl; O-ethyl; O-isopropyl; O-t-butyl; O—(CH$_2$)$_2$—O—CH$_3$; S-Methyl; S-Ethyl;

preferably on the condition that at least one of R$^{503}$, R$^{504}$, R$^{505}$ and R$^{506}$ is ≠H.

In particular,

R$^{503}$, R$^{504}$, R$^{505}$ and R$^{506}$ are each independently of one another are selected from the group consisting of H; F; Cl; Br; I; NO$_2$; CF$_3$; CN; (C=O)-methyl; (C=O)-ethyl; (C=O)-isopropyl; (C=O)-t-butyl; methyl; ethyl; isopropyl; t-butyl; O-methyl; O-Ethyl; O-isopropyl; O-t-butyl; OCF$_3$; S-methyl; S-ethyl; and SCF$_3$;

preferably on the condition that at least one of R$^{503}$, R$^{504}$, R$^{505}$ and R$^{506}$ is ≠H.

More particularly,

R$^{503}$, R$^{504}$, R$^{505}$ and R$^{506}$ are each independently of one another selected from the group consisting of H; F; Cl; Br; CF$_3$; CN; OCF$_3$ and NO$_2$;

preferably on the condition that at least one of R$^{503}$, R$^{504}$, R$^{505}$ and R$^{506}$ is ≠H.

Most preferred,

R$^{503}$, R$^{504}$ and R$^{506}$ each independently of one another represent H or F, preferably each denotes H; and R$^{505}$ denotes H; F; Cl; Br; CF$_3$; OCF$_3$; CN; or NO$_2$; preferably denotes F; Cl; Br; CF$_3$; OCF$_3$; or CN.

In a particular preferred embodiment of the compound according to general formula (5-I) at least one of the residues R$^{503}$, R$^{504}$, R$^{505}$ and R$^{506}$ is ≠H.

In another particular preferred embodiment of the compound according to general formula (5-I) at least two of the residues R$^{503}$, R$^{504}$, R$^{505}$ and R$^{506}$ denote H, preferably at least two of R$^{503}$, R$^{504}$ and R$^{506}$ denote H.

In a preferred embodiment of the compound according to general formula (5-I), the residue R$^{507}$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), OH, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue, a C(=O)—O—C$_{1-4}$-aliphatic residue, and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C(=O)—O—C$_{1-4}$-aliphatic residue a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, a C(=O)—O—C$_{1-4}$-aliphatic residue, OCF$_3$, SH, SCF$_3$, a S—C$_{1-4}$ aliphatic residue, CF$_3$, CN, a C$_{1-4}$-aliphatic residue and C(=O)—OH, on the condition that if R$^{507}$ denotes a 3 to 10 membered heterocycloaliphatic residue, the 3 to 10 membered heterocycloaliphatic residue is linked via a carbon atom.

In a further preferred embodiment of the compound according to general formula (5-I), the residue R$^{507}$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, OH, an O—C$_{1-4}$-aliphatic residue, OCF$_3$, SH, SCF$_3$, a S—C$_{1-4}$-aliphatic residue, a C(=O)—O—C$_{1-4}$-aliphatic residue, COOH, CF$_3$, CN, and a C$_{1-4}$-aliphatic residue wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, a C(=O)—O—C$_{1-4}$-aliphatic residue, CF$_3$, CN, a C$_{1-4}$-aliphatic residue, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, CF$_3$, CN, and a C$_{1-4}$-aliphatic residue, and wherein the C$_{3-10}$-cycloaliphatic residue or the 3 to 10 membered heterocycloaliphatic residue may in each case be optionally bridged, preferably is bridged, via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, OH, =O, an O—C$_{1-4}$ aliphatic residue, a C(=O)—O—C$_{1-4}$-aliphatic residue, OCF$_3$, SH, SCF$_3$, a S—C$_{1-4}$ aliphatic residue, CF$_3$, CN, and a C$_{1-4}$-aliphatic residue, on the condition that if $R^{507}$ denotes a 3 to 10 membered heterocycloaliphatic residue, the 3 to 10 membered heterocycloaliphatic residue is linked via a carbon atom.

Preferably, $R^{507}$ denotes a $C_{1-8}$-aliphatic residue, unsubstituted or mono- or polysubstituted with at least one substituent selected from the group consisting of F, Cl, Br, I, OH, an O—$C_{1-4}$-aliphatic residue, OCF$_3$, SH, SCF$_3$, a S—$C_{1-4}$-aliphatic residue, a C(=O)—O—$C_{1-4}$-aliphatic residue, COOH, CF$_3$, and a $C_{1-4}$-aliphatic residue wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a C(=O)—O—$C_{1-4}$-aliphatic residue, a S—$C_{1-4}$ aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, OCF$_3$, SH, SCF$_3$, a S—$C_{1-4}$ aliphatic residue, a C(=O)—O—$C_{1-4}$-aliphatic residue, CF$_3$, CN, and a $C_{1-4}$-aliphatic residue, on the condition that if $R^{507}$ denotes a 3 to 10 membered heterocycloaliphatic residue, the 3 to 10 membered heterocycloaliphatic residue is linked via a carbon atom.

More preferably, $R^{507}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, an O—$C_{1-4}$-aliphatic residue, OCF$_3$, SH, SCF$_3$, a S—$C_{1-4}$-aliphatic residue, COOH, CF$_3$, a C(=O)—O—$C_{1-4}$-aliphatic residue, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, a C(=O)—O—$C_{1-4}$-aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein the $C_{3-10}$-cycloaliphatic residue or the 3 to 10 membered heterocycloaliphatic residue in each case may be bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, OCF$_3$, SH, SCF$_3$, a S—$C_{1-4}$ aliphatic residue, a C(=O)—O—$C_{1-4}$-aliphatic residue, CF$_3$, CN, and a $C_{1-4}$-aliphatic residue, on the condition that if $R^{507}$ denotes a 3 to 10 membered heterocycloaliphatic residue, the 3 to 10 membered heterocycloaliphatic residue is linked via a carbon atom.

Even more preferably, $R^{507}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, an O—$C_{1-4}$-aliphatic residue, OCF$_3$, SH, SCF$_3$, a S—$C_{1-4}$-aliphatic residue, COOH, a C(=O)—O—$C_{1-4}$-aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, a C(=O)—O—$C_{1-4}$-aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein the $C_{3-10}$-cycloaliphatic residue or the 3 to 10 membered heterocycloaliphatic residue may in each case be bridged, preferably is bridged, via a unsubstituted $C_{1-8}$ aliphatic group, preferably an unsubstituted $C_{1-4}$ aliphatic group, on the condition that if $R^{507}$ denotes a 3 to 10 membered heterocycloaliphatic residue, the 3 to 10 membered heterocycloaliphatic residue is linked via a carbon atom.

Still more preferably, $R^{507}$ denotes a $C_{1-6}$-aliphatic residue, unsubstituted or mono- or polysubstituted with at least one substituent selected from the group consisting of F, Cl, Br, I, OH, an O—$C_{1-4}$-aliphatic residue, COOH, a C(=O)—O—$C_{1-4}$-aliphatic residue, OCF$_3$, SH, SCF$_3$, a S—$C_{1-4}$-aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, OH, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, a C(=O)—O—$C_{1-4}$-aliphatic residue, CF$_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue.

and wherein the $C_{3-10}$-cycloaliphatic residue or the 3 to 10 membered heterocycloaliphatic residue in each case may be bridged, preferably is bridged, via a unsubstituted $C_{1-4}$ aliphatic group, on the condition that if $R^{507}$ denotes a 3 to 10 membered heterocycloaliphatic residue, the 3 to 10 membered heterocycloaliphatic residue is linked via a carbon atom.

In particular, $R^{507}$ denotes a $C_{1-6}$-aliphatic residue, unsubstituted or mono- or polysubstituted with at least one substituent selected from the group consisting of F, Cl, Br, I, OH, an O—$C_{1-4}$-aliphatic residue, COOH, a C(=O)—O—$C_{1-4}$-aliphatic residue, OCF$_3$, SH, SCF$_3$, a S—$C_{1-4}$-aliphatic residue, CF$_3$, and a $C_{1-4}$-aliphatic residue, preferably unsubstituted or mono- or polysubstituted with at least one substituent selected from the group consisting of F, Cl, OH, an O—$C_{1-4}$-aliphatic residue, OCF$_3$, CF$_3$, and a $C_{1-4}$-aliphatic residue, wherein the $C_{1-4}$-aliphatic residue in each case may be unsubstituted or mono- or polysubstituted with at least one substituent selected from the group consisting of OH, and an unsubstituted O—$C_{1-4}$-aliphatic residue, or denotes a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, a C(=O)—O—$C_{1-4}$-aliphatic residue, CF$_3$, and a $C_{1-4}$-aliphatic residue, on the condition that if $R^{507}$ denotes a 3 to 6 membered heterocycloaliphatic residue, the 3 to 6 membered heterocycloaliphatic residue is linked via a carbon atom.

Most preferred, $R^{507}$ denotes a $C_{1-6}$-aliphatic residue, unsubstituted or mono- or polysubstituted with at least one substituent selected from the group consisting of F, Cl, OH, a C(=O)—O—$C_{1-4}$-aliphatic residue, COOH and an O—$C_{1-4}$-aliphatic residue, preferably at least one substituent selected from the group consisting of OH, a C(=O)—O—$C_{1-4}$-aliphatic residue, COOH and an O—$C_{1-4}$-aliphatic residue, wherein the $C_{1-4}$-aliphatic residue in each case may be unsubstituted or mono- or polysubstituted with at least one substituent selected from the group consisting of OH, and an unsubstituted O—$C_{1-4}$-aliphatic residue, or denotes a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, a C(=O)—O—$C_{1-4}$-aliphatic residue, CF$_3$, and a $C_{1-4}$-aliphatic residue, on the condition that if $R^{507}$ denotes a 3 to 6 membered heterocycloaliphatic residue, the 3 to 6 membered heterocycloaliphatic residue is linked via a carbon atom.

In particular most preferred $R^{507}$ is selected from the group consisting of CH$_3$, C$_2$H$_5$, C$_3$H$_7$, C$_4$H$_9$, C$_5$H$_{11}$, CH(CH$_3$)$_2$, C$_2$H$_4$—CH(CH$_3$)$_2$, C$_3$H$_6$—CH(CH$_3$)$_2$, CH$_2$OH, C$_2$H$_4$O, CH$_2$—OCH$_3$, C$_2$H$_4$—OCH$_3$, C$_3$H$_6$—OCH$_3$, CH$_2$—O—C$_2$H$_5$, C$_2$H$_4$—O—C$_2$H$_5$, CH$_2$—CH(CH$_3$)(OCH$_3$), CH$_2$—CH(C$_2$H$_5$)(OCH$_3$), CH(CH$_3$)(CH$_2$—OCH$_3$), CH(C$_2$H$_4$—OCH$_3$)$_2$, CH(C$_2$H$_5$)(CH$_2$—OCH$_3$), C$_2$H$_4$—O—C$_2$H$_4$—O—CH$_3$, CH$_2$—O—C$_2$H$_4$—O—CH$_3$, C$_2$H$_4$—O—C$_2$H$_4$—OH, CH$_2$—O—C$_2$H$_4$—OH, CH$_2$—C(=O)O—CH$_3$, C$_2$H$_4$—C(=O)OCH$_3$, C$_2$H$_4$—C(=O)OH, CH$_2$—C(=O)OH, or denotes an unsubstituted $C_{3-6}$-cycloaliphatic residue or an unsubstituted 3 to 6 membered heterocycloaliphatic residue, preferably tetrahydropyranyl or piperidinyl.

Particularly preferred is also a compound according to general formula (I), wherein $R^{501}$ represents the partial structure (5-T1), $$—(CR^{508a}R^{508b})_{m5}—R^{508c} \qquad (5\text{-}T1),$$

wherein m5 is 0, 1 or 2 and $R^{508a}$ and $R^{508b}$ each independently of one another represent H, F, a O—$C_{1-4}$ aliphatic residue or a $C_{1-4}$ aliphatic residue; preferably H, F, CH$_3$ or OCH$_3$;

$R^{508c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, CF$_3$, and an unsubstituted $C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, CF$_3$, and an unsubstituted $C_{1-4}$-aliphatic residue, or wherein m5 is 0, $R^{508a}$ and $R^{508b}$ each independently of one another represent H, F, a O—$C_{1-4}$ aliphatic residue or a $C_{1-4}$ aliphatic residue; preferably H, F, CH$_3$ or OCH$_3$; and $R^{508c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$, C(=O)—O—C$_2$H$_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, $X^5$ represents O or S, preferably O, $R^{502}$ is selected from the group consisting of F; Cl; Br; CF$_3$; CH$_3$; C$_2$H$_5$, iso-propyl; cyclopropyl; and O—CH$_3$, $R^{503}$, $R^{504}$, $R^{505}$ and $R^{506}$ are each independently of one another selected from the group consisting of H; F; Cl; Br; CF$_3$; CN; OCF$_3$ and NO$_2$;

preferably on the condition that at least one of $R^{503}$, $R^{504}$, $R^{505}$ and $R^{506}$ is ≠H, $R^{507}$ denotes a $C_{1-6}$-aliphatic residue, unsubstituted or mono- or polysubstituted with at least one substituent selected from the group consisting of F, Cl, Br, I, OH, an O—$C_{1-4}$-aliphatic residue, COOH, a C(=O)—O—$C_{1-4}$-aliphatic residue, OCF$_3$, SH, SCF$_3$, a S—$C_{1-4}$-aliphatic residue, CF$_3$, and a $C_{1-4}$-aliphatic residue, preferably unsubstituted or mono- or polysubstituted with at least one substituent selected from the group consisting of F, Cl, OH, an O—$C_{1-4}$-aliphatic residue, OCF$_3$, CF$_3$, and a $C_{1-4}$-aliphatic residue, wherein the $C_{1-4}$-aliphatic residue in each case may be unsubstituted or mono- or polysubstituted with at least one substituent selected from the group consisting of OH, and an unsubstituted O—$C_{1-4}$-aliphatic residue, or denotes an unsubstituted $C_{3-6}$-cycloaliphatic residue or an unsubstituted 3 to 6 membered heterocycloaliphatic residue, on the condition that if $R^{507}$ denotes a 3 to 6 membered heterocycloaliphatic residue, the 3 to 6 membered heterocycloaliphatic residue is linked via a carbon atom.

Particularly preferred is also a compound according to general formula (5-I), wherein $R^{501}$ represents aryl, preferably phenyl, or heteroaryl, preferably pyridyl or thienyl, in each case unsubstituted or mono- or disubstituted with at least one substituent selected from the group consisting of F, Cl, Br, I, OH, $OCH_3$, $OCF_3$, $CF_3$, CN, and $CH_3$, preferably represents phenyl, unsubstituted or mono- or disubstituted with at least one substituent selected from the group consisting of F, Cl, Br, I, OH, $OCH_3$, $OCF_3$, $CF_3$, CN, and $CH_3$;

$X^5$ is O;

$R^{502}$ is selected from the group consisting of F, Cl, $CF_3$, $CH_3$, $C_2H_5$, iso-propyl, cyclopropyl, and O—$CH_3$; preferably is selected from the group consisting of $CH_3$, $C_2H_5$, $OCH_3$ and $CF_3$;

$R^{503}$, $R^{504}$, $R^{505}$ and $R^{506}$ are each independently of one another selected from the group consisting of H, F, Cl, Br, $CF_3$, CN, $OCF_3$ and $NO_2$;

preferably on the condition that at least one of $R^{503}$, $R^{504}$, $R^{505}$ and $R^{506}$ is ≠H, more preferably on the condition that $R^{505}$ is ≠H;

$R^{507}$ denotes a saturated $C_{1-6}$-aliphatic residue, unsubstituted or mono- or disubstituted with at least one substituent selected from the group consisting of F, Cl, Br, I, OH, O—$CH_3$, O—$C_2H_5$, $OCF_3$, $OC_2H_4$—O—$CH_3$, COOH, C(=O)$OCH_3$, $SCF_3$, and $CF_3$, preferably denotes a saturated $C_{1-6}$-aliphatic residue, unsubstituted or mono- or disubstituted with at least one substituent selected from the group consisting of OH, O—$CH_3$, O—$C_2H_5$, $OCF_3$, $OC_2H_4$—O—$CH_3$, COOH, and C(=O)$OCH_3$.

Another embodiment of the present invention therefore relates to a compound of general formula (I), wherein the compound is selected from a compound according to general formula (6-I).

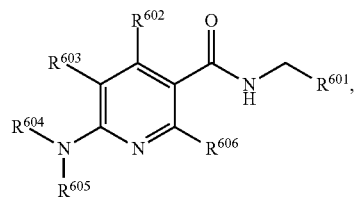

(6-I)

wherein $R^{601}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^{602}$ represents F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may in each case be unsubstituted or mono- or polysubstituted; a $C_{3-8}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{603}$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted; a $C_{3-8}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{604}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged, preferably in each case bridged, via a $C_{1-8}$ aliphatic group, which in turn may be unsubstituted or mono- or polysubstituted;

on the condition that if $R^{604}$ denotes a 3 to 10 membered heterocycloaliphatic residue or a heteroaryl, the 3 to 10 membered heterocycloaliphatic residue or the heteroaryl is linked via a carbon atom;

$R^{605}$ denotes H or a $C_{1-10}$-aliphatic residue, preferably a $C_{1-4}$-aliphatic residue, unsubstituted or mono- or polysubstituted;

or $R^{604}$ and $R^{605}$ form together with the nitrogen atom connecting them a 3 to 10 membered heterocycloaliphatic residue, preferably a 4 to 7 membered heterocycloaliphatic residue, unsubstituted or mono- or polysubstituted, which may optionally be condensed with aryl or heteroaryl, preferably selected from the group consisting of phenyl, pyridyl and thienyl, wherein the aryl or heteroaryl residues condensed in this way can for their part be respectively unsubstituted or mono- or polysubstituted;

$R^{606}$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{606}$ denotes a 3 to 10 membered heterocycloaliphatic residue, the 3 to 10 membered heterocycloaliphatic residue is linked via a carbon atom, or denotes S—$R^{607}$, O—$R^{608}$ or N($R^{609}R^{610}$), wherein $R^{607}$ and $R^{608}$ in each case represent a $C_{1-10}$-aliphatic residue, unsubstituted or mono- or polysubstituted; a C$_{3-10}$-cycloaliphatic residue or a 3 to 10 membered heterocycloaliphatic residue, in each case unsubstituted or mono- or polysubstituted and in each case optionally bridged via a C$_{1-8}$ aliphatic group, which in turn may be unsubstituted or mono- or polysubstituted;

on the condition that if R$^{607}$ or R$^{608}$ denotes a 3 to 10 membered heterocycloaliphatic residue, the 3 to 10 membered heterocycloaliphatic residue is linked via a carbon atom, R$^{609}$ represents a C$_{1-10}$-aliphatic residue, unsubstituted or mono- or polysubstituted; a C$_{3-10}$-cycloaliphatic residue or a 3 to 10 membered heterocycloaliphatic residue, in each case unsubstituted or mono- or polysubstituted and in each case optionally bridged via a C$_{1-8}$ aliphatic group, which in turn may be unsubstituted or mono- or polysubstituted;

on the condition that if R$^{609}$ denotes a 3 to 10 membered heterocycloaliphatic residue, the 3 to 10 membered heterocycloaliphatic residue is linked via a carbon atom;

R$^{610}$ denotes H or a C$_{1-10}$-aliphatic residue, preferably a C$_{1-4}$-aliphatic residue, unsubstituted or mono- or polysubstituted;

or

R$^{609}$ and R$^{610}$ form together with the nitrogen atom connecting them a 3 to 10 membered heterocycloaliphatic residue, preferably a 4 to 7 membered heterocycloaliphatic residue, unsubstituted or mono- or polysubstituted; which may optionally be condensed with aryl or heteroaryl, wherein the aryl or heteroaryl residues condensed in this way can for their part be respectively unsubstituted or mono- or polysubstituted;

in which an "aliphatic group" and an "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a NH—S(=O)$_2$—C$_{1-4}$ aliphatic residue, =O, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, NO$_2$, NH$_2$, an NH(C$_{1-4}$ aliphatic residue), an N(C$_{1-4}$ aliphatic residue)$_2$, a NH—C(=O)—C$_{1-4}$ aliphatic residue, a NH—S(=O)$_2$—C$_{1-4}$ aliphatic residue, =O, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, CHO, COOH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, C(=O)—NH$_2$, a C(=O)—NH(C$_{1-4}$ aliphatic residue), and a C(=O)—N(C$_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO$_2$, NH$_2$,

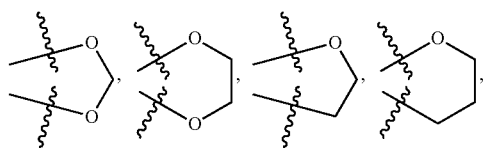

an NH(C$_{1-4}$ aliphatic residue), an N(C$_{1-4}$ aliphatic residue)$_2$, an NH—C(=O)—C$_{1-4}$ aliphatic residue, an NH—S(=O)$_2$—C$_{1-4}$ aliphatic residue, OH, OCF$_3$, a O—C$_{1-4}$-aliphatic residue, a O—C(=O)—C$_{1-4}$-aliphatic residue, SH, SCF$_3$, a S—C$_{1-4}$-aliphatic residue, S(=O)$_2$OH, a S(=O)$_2$—C$_{1-4}$-aliphatic residue, a S(=O)$_2$—O—C$_{1-4}$-aliphatic residue, a S(=O)$_2$—NH—C$_{1-4}$-aliphatic residue, CN, CF$_3$, C(=O)H, C(=O)OH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, benzyl, aryl, heteroaryl, C(=O)—NH$_2$, a C(=O)—NH(C$_{1-4}$ aliphatic residue), and a C(=O)—N(C$_{1-4}$ aliphatic residue)$_2$.

In an particularly preferred embodiment of the compound according to general formula (6-I) radicals R$^{601}$, R$^{602}$, R$^{603}$, R$^{604}$, R$^{605}$ and R$^{606}$ have the meanings described herein in connection with the compounds according to the invention and preferred embodiments thereof, with the proviso that R$^{601}$ comprises at least 4 atoms selected from the group consisting of carbon and heteroatoms, preferably at least 4 atoms selected from the group consisting of carbon atoms and heteroatoms selected from the group consisting of N, O and S.

The compounds according to general formula (6-I) are known from WO 2012/052167 A1, which is fully included by reference.

The present invention further relates to a substituted compound of general formula (6-I),

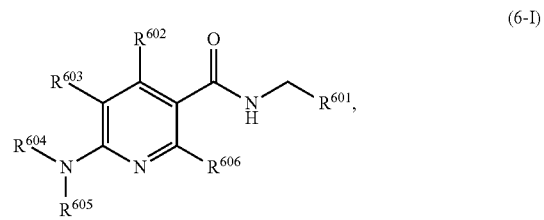

(6-I)

wherein

R$^{601}$ represents a C$_{1-10}$-aliphatic residue, unsubstituted or mono- or polysubstituted; a C$_{3-10}$ cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^{602}$ represents F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{603}$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted; a $C_{3-8}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{604}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged, preferably in each case bridged, via a $C_{1-8}$ aliphatic group, which in turn may be unsubstituted or mono- or polysubstituted;

on the condition that if $R^{604}$ denotes a 3 to 10 membered heterocycloaliphatic residue or a heteroaryl, the 3 to 10 membered heterocycloaliphatic residue or the heteroaryl is linked via a carbon atom;

$R^{605}$ denotes H or a $C_{1-10}$-aliphatic residue, preferably a $C_{1-4}$-aliphatic residue, unsubstituted or mono- or polysubstituted;

or $R^{604}$ and $R^{605}$ form together with the nitrogen atom connecting them a 3 to 10 membered heterocycloaliphatic residue, preferably a 4 to 7 membered heterocycloaliphatic residue, unsubstituted or mono- or polysubstituted;

$R^{606}$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{606}$ denotes a 3 to 10 membered heterocycloaliphatic residue, the 3 to 10 membered heterocycloaliphatic residue is linked via a carbon atom, or denotes S—$R^{607}$, O—$R^{608}$ or N($R^{609}R^{610}$), wherein $R^{607}$ and $R^{608}$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{607}$ or $R^{608}$ denotes a 3 to 10 membered heterocycloaliphatic residue, the 3 to 10 membered heterocycloaliphatic residue is linked via a carbon atom, $R^{609}$ represents a $C_{1-10}$-aliphatic residue, unsubstituted or mono- or poly-substituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{609}$ denotes a 3 to 10 membered heterocycloaliphatic residue, the 3 to 10 membered heterocycloaliphatic residue is linked via a carbon atom;

$R^{610}$ denotes a $C_{1-10}$-aliphatic residue, preferably a $C_{1-4}$-aliphatic residue, unsubstituted or mono- or polysubstituted;

or $R^{609}$ and $R^{610}$ form together with the nitrogen atom connecting them a 3 to 10 membered heterocycloaliphatic residue, preferably a 4 to 7 membered heterocycloaliphatic residue, unsubstituted or mono- or polysubstituted;

in which an "aliphatic group" and an "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)₂—NH—C₁₋₄-aliphatic residue, CN, CF₃, CHO, COOH, a C₁₋₄-aliphatic residue, a C(=O)—C₁₋₄-aliphatic residue, a C(=O)—O—C₁₋₄-aliphatic residue, a C₃₋₆-cycloaliphatic residue, a 3 to 6 membered heterocycloaliphatic residue, C(=O)—NH₂, a C(=O)—NH(C₁₋₄ aliphatic residue), and a C(=O)—N(C₁₋₄ aliphatic residue)₂;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, NO₂, NH₂,

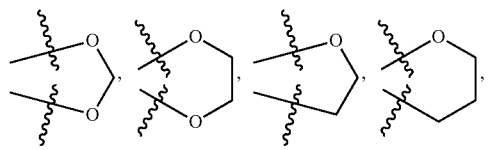

an NH(C₁₋₄ aliphatic residue), an N(C₁₋₄ aliphatic residue)₂, an NH—C(=O)—C₁₋₄ aliphatic residue, an NH—S(=O)₂—C₁₋₄ aliphatic residue, OH, OCF₃, a O—C₁₋₄-aliphatic residue, a O—C(=O)—C₁₋₄-aliphatic residue, SH, SCF₃, a S—C₁₋₄-aliphatic residue, S(=O)₂OH, a S(=O)₂—C₁₋₄-aliphatic residue, a S(=O)₂—O—C₁₋₄-aliphatic residue, a S(=O)₂—NH—C₁₋₄-aliphatic residue, CN, CF₃, C(=O)H, C(=O)OH, a C₁₋₄-aliphatic residue, a C(=O)—C₁₋₄-aliphatic residue, a C(=O)—O—C₁₋₄-aliphatic residue, a C₃₋₆-cycloaliphatic residue, a 3 to 6 membered heterocycloaliphatic residue, benzyl, aryl, heteroaryl, C(=O)—NH₂, a C(=O)—NH(C₁₋₄ aliphatic residue), and a C(=O)—N(C₁₋₄ aliphatic residue)₂.

In another preferred embodiment of the compound according to formula (6-I), preferred substituents of "cycloaliphatic residue" and "heterocycloaliphatic residue" are selected from the group consisting of F, Cl, Br, I, NO₂, NH₂, an NH(C₁₋₄ aliphatic residue), an N(C₁₋₄ aliphatic residue)₂, a NH—C(=O)—C₁₋₄ aliphatic residue, a NH—S(=O)₂—C₁₋₄ aliphatic residue, =O, OH, OCF₃, a O—C₁₋₄-aliphatic residue, a O—C(=O)—C₁₋₄-aliphatic residue, SH, SCF₃, a S—C₁₋₄-aliphatic residue, S(=O)₂OH, a S(=O)₂—C₁₋₄-aliphatic residue, a S(=O)₂—O—C₁₋₄-aliphatic residue, a S(=O)₂—NH—C₁₋₄-aliphatic residue, CN, CF₃, CHO, COOH, a C₁₋₄-aliphatic residue, CH₂OH, CH₂—OCH₃, C₂H₄—OH, C₂H₄—OCH₃CH₂—CF₃, a C(=O)—C₁₋₄-aliphatic residue, a C(=O)—O—C₁₋₄-aliphatic residue, a C₃₋₆-cycloaliphatic residue, a 3 to 6 membered heterocycloaliphatic residue, C(=O)—NH₂, a C(=O)—NH(C₁₋₄ aliphatic residue), and a C(=O)—N(C₁₋₄ aliphatic residue)₂.

In another preferred embodiment of the compound according to formula (6-I), preferred substituents of "aryl" and "heteroaryl" are selected from the group consisting of F, Cl, Br, I, NO₂,

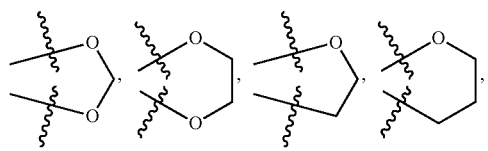

an NH₂, an NH(C₁₋₄ aliphatic residue), an N(C₁₋₄ aliphatic residue)₂, an NH—C(=O)—C₁₋₄ aliphatic residue, an NH—S(=O)₂—C₁₋₄ aliphatic residue, OH, OCFH₂, OCF₂H, OCF₃, a O—C₁₋₄-aliphatic residue, SH, SCF₃, a S—C₁₋₄-aliphatic residue, S(=O)₂OH, a S(=O)₂—C₁₋₄-aliphatic residue, a S(=O)₂—NH—C₁₋₄-aliphatic residue, CN, CF₃, CF₂H, CHF₂, a C₁₋₄-aliphatic residue, CH₂OH, CH₂—OCH₃, C₂H₄—OH, C₂H₄—OCH₃, a C(=O)—C₁₋₄-aliphatic residue, a C(=O)—O—C₁₋₄-aliphatic residue, a C₃₋₆-cycloaliphatic residue, a 3 to 6 membered heterocycloaliphatic residue, CONH₂, a C(=O)—NH(C₁₋₄ aliphatic residue), a C(=O)—N(C₁₋₄ aliphatic residue)₂, aryl, preferably phenyl, or benzyl, in each case unsubstituted or mono- or polysubstituted with at least one substituent selected from the group consisting of F, Cl, Br, I, CN, CF₃, CH₃, C₂H₅, iso-propyl, tert.-butyl, C(=O)—OH, C(=O)—CH₃, C(=O)—C₂H₅, C(=O)—O—CH₃ and C(=O)—O—C₂H₅, O—CH₃, OCF₃, O—CH₂—OH, O—CH₂—O—CH₃, SH, S—CH₃, SCF₃, NO₂, NH₂, N(CH₃)₂, N(CH₃)(C₂H₅) and N(C₂H₅)₂, heteroaryl, preferably pyridyl, thienyl, furyl, thiazolyl or oxazolyl, in each case unsubstituted or mono- or polysubstituted with at least one substituent selected from the group consisting of F, Cl, Br, I, CN, CF₃, CH₃, C₂H₅, iso-propyl, tert.-butyl, C(=O)—OH, C(=O)—CH₃, C(=O)—C₂H₅, C(=O)—O—CH₃ and C(=O)—O—C₂H₅, O—CH₃, OCF₃, O—CH₂—OH, O—CH₂—O—CH₃, SH, S—CH₃, SCF₃, NO₂, NH₂, N(CH₃)₂, N(CH₃)(C₂H₅) and N(C₂H₅)₂.

In yet another preferred embodiment of the compound according to general formula (6-I) the particular radicals R⁶⁰¹-R⁶⁰⁵ have the meanings described herein in connection with the compounds according to the invention and preferred embodiments thereof and R⁶⁰⁶ represents a C₂₋₁₀-aliphatic residue, unsubstituted or mono- or polysubstituted; a C₃₋₁₀-cycloaliphatic residue or a 3 to 10 membered heterocycloaliphatic residue, in each case unsubstituted or mono- or polysubstituted and in each case optionally bridged via a C₁₋₈ aliphatic group, which in turn may be unsubstituted or mono- or polysubstituted;

on the condition that if R⁶⁰⁶ denotes a 3 to 10 membered heterocycloaliphatic residue, the 3 to 10 membered heterocycloaliphatic residue is linked via a carbon atom, or denotes S—R⁶⁰⁷ or O—R⁶⁰⁸ wherein R⁶⁰⁷ and R⁶⁰⁸ in each case represent a C₁₋₁₀-aliphatic residue, unsubstituted or mono- or polysubstituted; a C₃₋₁₀-cycloaliphatic residue or a 3 to 10 membered heterocycloaliphatic residue, in each case unsubstituted or mono- or polysubstituted and in each case optionally bridged via a C₁₋₈ aliphatic group, which in turn may be unsubstituted or mono- or polysubstituted;

on the condition that if R⁶⁰⁷ or R⁶⁰⁸ denotes a 3 to 10 membered heterocycloaliphatic residue, the 3 to 10 membered heterocycloaliphatic residue is linked via a carbon atom.

In another preferred embodiment of the present invention the compound according to general formula (6-I) has the general formula (6-I-a)

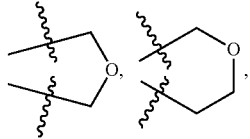

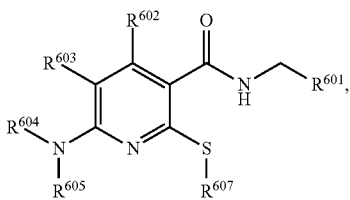

(6-I-a)

wherein
the particular radicals $R^{601}$-$R^{605}$ and $R^{607}$ have the meanings described herein in connection with the compounds according to the invention and preferred embodiments thereof.

In another preferred embodiment of the present invention the compound according to general formula (6-I) has the general formula (6-I-b)

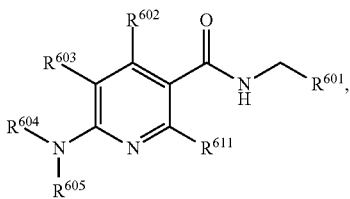

(6-I-b)

wherein the particular radicals $R^{601}$-$R^{605}$ have the meanings described herein in connection with the compounds according to the invention and preferred embodiments thereof, and wherein
$R^{611}$ represents O—$R^{608}$ or $N(R^{809}R^{610})$,
  wherein $R^{608}$, $R^{609}$ and $R^{610}$ have the meanings described herein in connection with the compounds according to the invention and preferred embodiments thereof,
  or represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
  on the condition that if $R^{611}$ denotes a 3 to 10 membered heterocycloaliphatic residue, the binding is carried out via a carbon atom of the 3 to 10 membered heterocycloaliphatic residue.

In a particular preferred embodiment of the present invention, radical $R^{611}$ in general formula (6-I-b) and radical $R^{606}$ in general formula (6-I) represents O—$R^{608}$, wherein $R^{608}$ has the meanings described herein in connection with the compounds according to the invention and preferred embodiments thereof.

In another particular preferred embodiment of the present invention, radical $R^{611}$ in general formula (6-I-b) and radical $R^{606}$ in general formula (6-I) represents $N(R^{609}R^{610})$ wherein $R^{609}$ and $R^{610}$ have the meanings described herein in connection with the compounds according to the invention and preferred embodiments thereof.

In yet another particular preferred embodiment of the present invention, radical $R^{611}$ in general formula (6-I-b) and radical $R^{606}$ in general formula (6-I) represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted,
on the condition that if $R^{611}$ denotes a 3 to 10 membered heterocycloaliphatic residue, the binding is carried out via a carbon atom of the 3 to 10 membered heterocycloaliphatic residue.

Another preferred embodiment of the compound according to general formula (6-I) has the general formula (6-I-c),

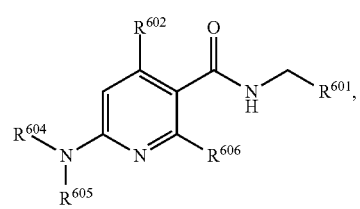

(6-I-c)

wherein the particular radicals $R^{601}$, $R^{602}$, $R^{604}$, $R^{605}$ and $R^{606}$ have the meanings described herein in connection with the compounds according to the invention and preferred embodiments thereof.

Another preferred embodiment of the compound according to general formula (6-I) has the general formula (6-I-e) or (6-I-f),

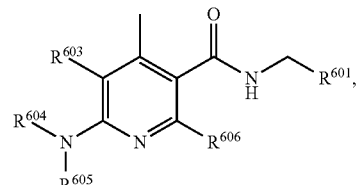

(6-I-e)

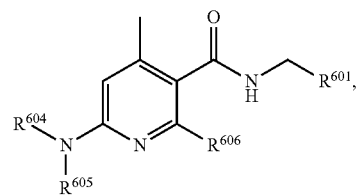

(6-I-f)

wherein the particular radicals $R^{601}$, $R^{603}$, $R^{604}$, $R^{605}$ and $R^{606}$ or $R^{601}$, $R^{604}$, $R^{605}$ and $R^{606}$, respectively, have the meanings described herein in connection with the compounds according to the invention and preferred embodiments thereof.

In yet another preferred embodiment of the compound according to general formula (6-I) radicals $R^{602}$, $R^{603}$, $R^{604}$, $R^{605}$ and $R^{606}$ have the meanings described herein in connection with the compounds according to the invention and preferred embodiments thereof, and $R^{601}$ represents aryl or heteroaryl, in each case unsubstituted or mono- or polysubstituted.

In case $R^{604}$ and $R^{605}$ of the compound of general formula (6-I) form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl or with a $C_{3-10}$ cycloaliphatic residue or with a 3 to 10 membered heterocycloaliphatic residue, wherein the aryl, heteroaryl, $C_{3-10}$ cycloaliphatic or 3 to 10 membered heterocycloaliphatic residues condensed in this way can for their part be respectively unsubstituted or mono- or polysubstituted. Preferably, said heterocycloaliphatic residue formed by $R^{604}$ and $R^{605}$ of the compound of general formula (6-I) together with the nitrogen atom connecting them may optionally be condensed with aryl or heteroaryl, wherein the aryl, or heteroaryl, preferably selected from the group consisting of phenyl, pyridyl and thienyl condensed in this way can for their part be respectively unsubstituted or mono- or polysubstituted.

Particularly preferably, in case $R^{604}$ and $R^{605}$ form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl, preferably selected from the group consisting of phenyl, pyridyl and thienyl, wherein the aryl or heteroaryl residues condensed in this way can for their part be respectively unsubstituted or mono- or polysubstituted.

In case $R^{609}$ and $R^{610}$ of the compound of general formula (6-I) form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl or with a $C_{3-10}$ cycloaliphatic residue or with a 3 to 10 membered heterocycloaliphatic residue, wherein the aryl, heteroaryl, $C_{3-10}$ cycloaliphatic or 3 to 10 membered heterocycloaliphatic residues condensed in this way can for their part be respectively unsubstituted or mono- or polysubstituted. Preferably, said heterocycloaliphatic residue formed by $R^{609}$ and $R^{610}$ of the compound of general formula (6-I) together with the nitrogen atom connecting them may optionally be condensed with aryl or heteroaryl, wherein the aryl, or heteroaryl, preferably selected from the group consisting of phenyl, pyridyl and thienyl condensed in this way can for their part be respectively unsubstituted or mono- or polysubstituted.

Particularly preferably, in case $R^{609}$ and $R^{610}$ form together with the nitrogen atom connecting them a 3 to 10 membered heterocycloaliphatic residue, preferably a 4 to 7 membered heterocycloaliphatic residue, unsubstituted or mono- or polysubstituted, said heterocycloaliphatic residue may optionally be condensed with aryl or heteroaryl, preferably selected from the group consisting of phenyl, pyridyl and thienyl, wherein the aryl or heteroaryl residues condensed in this way can for their part be respectively unsubstituted or mono- or polysubstituted.

Yet another preferred embodiment of present invention is a compound according to general formula (6-I), wherein $R^{601}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCF_3$, SH, $SCF_3$, a S—$C_{1-4}$-aliphatic residue, a $S(=O)_2$—$C_{1-4}$-aliphatic residue, $CF_3$, CN, a $C_{1-4}$-aliphatic residue and C(=O)—OH, preferably denotes a $C_{1-10}$-aliphatic residue, more preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, a $S(=O)_2$—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

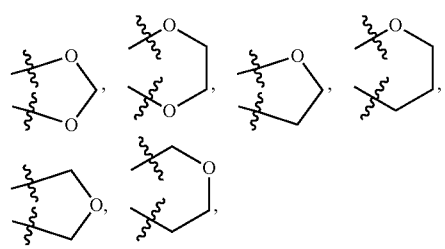

benzyl, phenyl, thienyl, pyridyl, furyl, thiazolyl and oxazolyl, preferably in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

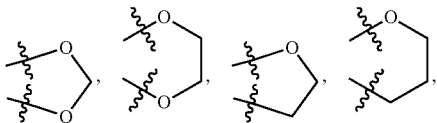

benzyl, phenyl, thienyl, pyridyl, furyl, thiazolyl and oxazolyl,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein benzyl, phenyl, thienyl, pyridyl, furyl, thiazolyl and oxazolyl may in each case be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
  and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN and C(=O)—OH,
$R^{602}$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted, preferably represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue; a $C_{3-6}$-cycloali-phatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-8}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue,
$R^{603}$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue,
  wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue;
  a $C_{3-8}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue,
  wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue,
  and wherein the $C_{3-8}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue,
$R^{604}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
  or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—C$_{1-4}$-aliphatic residue a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, a C(=O)—O—C$_{1-4}$-aliphatic residue, OCF$_3$, SH, SCF$_3$, a S—C$_{1-4}$ aliphatic residue, CF$_3$, CN, a C$_{1-4}$-aliphatic residue and C(=O)—OH, on the condition that if R$^{604}$ denotes a 3 to 10 membered heterocycloaliphatic residue, the 3 to 10 membered heterocycloaliphatic residue is linked via a carbon atom, or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

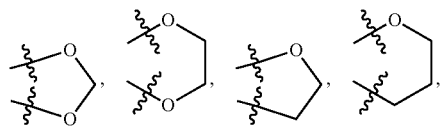

benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or poly-substituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the aryl or the heteroaryl residue may in each case be optionally bridged, preferably in each case is bridged, via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN and C(=O)—OH, R$^{605}$ denotes H or a C$_{1-10}$-aliphatic residue, preferably a C$_{1-4}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or R$^{604}$ and R$^{605}$ form together with the nitrogen atom connecting them a 3 to 10 membered heterocycloaliphatic residue, preferably a 4 to 7 membered heterocycloaliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a &C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, =O, OCF$_3$, CF$_3$ and an unsubstituted O—C$_{1-4}$-aliphatic residue, preferably selected from the group consisting of F, Cl, Br, I, OH, OCF$_3$, CF$_3$ and an unsubstituted O—C$_{1-4}$-aliphatic residue and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the 3 to 10 membered heterocycloaliphatic residue formed by R$^4$ and R$^5$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

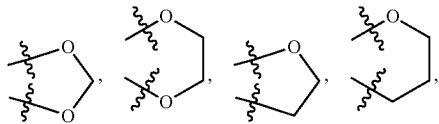

benzyl, phenyl, thienyl, pyridyl, furyl, thiazolyl and oxazolyl, and wherein the 3 to 10 membered heterocycloaliphatic residue formed by R$^4$ and R$^5$ together with the nitrogen atom connecting them may optionally be condensed with a C$_{3-10}$ cycloaliphatic residue or a 3 to 10 membered heterocycloaliphatic residue, wherein the C$_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, =O, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, R$^{606}$ denotes a C$_{2-10}$-aliphatic residue, preferably a C$_{2-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, on the condition that if R$^{606}$ denotes a 3 to 10 membered heterocycloaliphatic residue, the 3 to 10 membered heterocycloaliphatic residue is linked via a carbon atom, or R$^{606}$ denotes S—R$^{607}$, O—R$^{608}$ or N(R$^{609}$R$^{610}$), wherein R$^{607}$ and R$^{608}$ in each case represent a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, or in each case represent a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{607}$ or $R^{608}$ denotes a 3 to 10 membered heterocycloaliphatic residue, the 3 to 10 membered heterocycloaliphatic residue is linked via a carbon atom of the 3 to 10 membered heterocycloaliphatic residue, $R^{609}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{609}$ denotes a 3 to 10 membered heterocycloaliphatic residue, the 3 to 10 membered heterocycloaliphatic residue is linked via a carbon atom of the 3 to 10 membered heterocycloaliphatic residue, $R^{610}$ denotes H or a $C_{1-10}$-aliphatic residue, preferably a $C_{1-4}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH; preferably denotes a $C_{1-10}$-aliphatic residue, more preferably a $C_{1-4}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or $R^{609}$ and $R^{610}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the 3 to 10 membered heterocycloaliphatic residue formed by $R^{609}$ and $R^{610}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

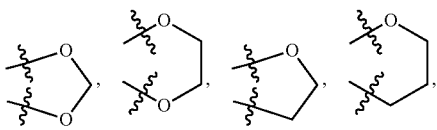

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

In a preferred embodiment of the compound according to general formula (6-I), the residue $R^{601}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCF_3$, SH, $SCF_3$, a S—$C_{1-4}$-aliphatic residue, a $S(=O)_2$—$C_{1-4}$-aliphatic residue, $CF_3$, CN, a $C_{1-4}$-aliphatic residue and C(=O)—OH, preferably denotes a $C_{1-10}$-aliphatic residue, more preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or poly-substituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, a $S(=O)_2$—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

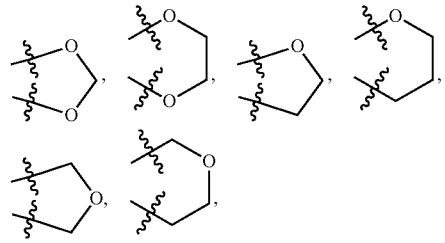

benzyl, phenyl, thienyl, pyridyl, furyl, thiazolyl and oxazolyl, preferably in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

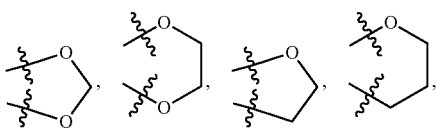

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
and wherein the aryl or the heteroaryl residue may in each case may be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and C(=O)—OH.

In a further preferred embodiment of the compound according to general formula (6-I), the residue $R^{601}$ represents the partial structure (6-T1)

—(CR$^{612a}$R$^{612b}$)$_{m6}$—R$^{612c}$     (6-T1), wherein
m6 denotes 0, 1, 2, 3 or 4, preferably denotes 0, 1, 2 or 3, more preferably denotes 0, 1, or 2,
$R^{612a}$ and $R^{612b}$ each independently of one another represent H, F, Cl, Br, I, $NO_2$, $NH_2$, a NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH, or together denote =O, preferably each independently of one another represent H, F, Cl, Br, I, $NH_2$, a NH($C_{1-4}$ aliphatic residue), a N($C_{1-4}$ aliphatic residue)$_2$, OH, O—$C_{1-4}$ aliphatic residue or a $C_{1-4}$ aliphatic residue, or together denote =O,
more preferably each independently of one another represent H, F, Cl, Br, I, OH, an O—$C_{1-4}$ aliphatic residue or a $C_{1-4}$ aliphatic residue, or together denote =O,
even more preferably each independently of one another represent H, F, OH, an O—$C_{1-4}$ aliphatic residue or a $C_{1-4}$ aliphatic residue, or together denote =O, and
$R^{612c}$ denotes a $C_{1-4}$ aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, a S(=O)$_2$—$C_{1-4}$ aliphatic residue, $CF_3$, CN, a $C_{1-4}$-aliphatic residue and C(=O)—OH, preferably denotes a $C_{1-4}$ aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue, preferably when m6 is ≠0,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes—preferably when m6 is 0 or 2, more preferably when m6 is 0—an aryl or heteroaryl, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, a S(=O)$_2$—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

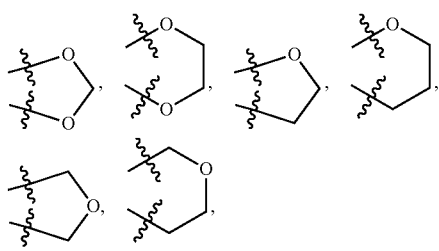

benzyl, phenyl, thienyl, pyridyl, furyl, thiazolyl and oxazolyl, preferably denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

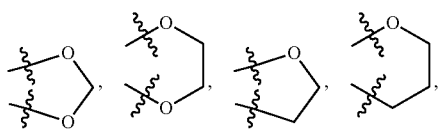

benzyl, phenyl, thienyl, pyridyl, furyl, thiazolyl and oxazolyl, preferably when m6 is =0,
- wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
- wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
- wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

Preferably,
$R^{601}$ represents the partial structure (6-T1),
wherein
m6 denotes 0, 1, 2 or 3, preferably denotes 0, 1 or 2,
$R^{612a}$ and $R^{612b}$ each independently of one another represent H, F, Cl, Br, I, OH, an O—$C_{1-4}$ aliphatic residue or a $C_{1-4}$ aliphatic residue, or together denote =O,
preferably each independently of one another represent H, F, OH, a O—$C_{1-2}$ aliphatic residue or a $C_{1-2}$ aliphatic residue, or together denote =O, and
$R^{612c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCF_3$, $CF_3$, CN, a $C_{1-4}$-aliphatic residue, a $S(=O)_2$—$C_{1-4}$-aliphatic residue and C(=O)—OH, preferably denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue, C(=O)—OH, a $C_{3-6}$ cycloaliphatic residue, and a 3 to 6 membered heterocycloaliphatic residue,
- wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
- wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes—preferably when m6 is 0 or 2, more preferably when m6 is 0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, SH, $SCF_3$, a S—$C_{1-4}$ aliphatic residue, a $S(=O)_2$—$C_{1-4}$ aliphatic residue, $NO_2$, $N(C_{1-4}$ aliphatic residue)$_2$, $CF_3$, CN, a $C_{1-4}$-aliphatic residue, C(=O)—OH, C(=O)—$CH_3$, C(=O)—$C_2H_5$, C(=O)—O—$CH_3$, C(=O)—O—$C_2H_5$,

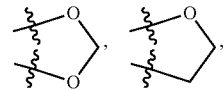

a $C_{3-6}$ cycloaliphatic residue, a 3 to 6 membered heterocycloaliphatic residue, benzyl, phenyl, thienyl, pyridyl, furyl, thiazolyl or oxazolyl, preferably denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$, C(=O)—O—$C_2H_5$,
a $C_{3-6}$ cycloaliphatic residue, a 3 to 6 membered heterocycloaliphatic residue, benzyl, phenyl, thienyl, pyridyl, furyl, thiazolyl or oxazolyl, preferably when m6 is 0,
- wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
- wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$ a $C_{1-4}$-aliphatic residue and C(=O)—OH.

More preferably, $R^{601}$ represents the partial structure (6-T1),
wherein
m6 denotes 0, 1, 2 or 3, preferably denotes 0, 1 or 2,
$R^{612a}$ and $R^{612b}$ each independently of one another represent H, F, Cl, Br, I, OH, an O—$C_{1-4}$ aliphatic residue or a $C_{1-4}$ aliphatic residue, or together denote =O, preferably each independently of one another represent H, F, OH, a O—$C_{1-2}$ aliphatic residue or a $C_{1-2}$ aliphatic residue, or together denote =O, and
$R^{612c}$ denotes a $C_{1-4}$ aliphatic residue, unsubstituted or mono- or polysubstituted with at least one substituent selected from the group consisting of F, Cl, Br, I, OH, an O—$C_{1-4}$ aliphatic residue, CF$_3$, CN, a S(=O)$_2$—$C_{1-4}$-aliphatic residue and a $C_{1-4}$-aliphatic residue, preferably denotes a $C_{1-4}$ aliphatic residue, unsubstituted or mono- or polysubstituted with at least one substituent selected from the group consisting of F, Cl, Br, I, an O—$C_{1-4}$ aliphatic residue, CF$_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, CF$_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, CF$_3$, and a $C_{1-4}$-aliphatic residue,
wherein the $C_{1-4}$-aliphatic residue in each case may be unsubstituted or mono- or polysubstituted with at least one substituent selected from the group consisting of F, Cl, CF$_3$ and an unsubstituted O—$C_{1-4}$-aliphatic residue,
or denotes—preferably when m6 is 0 or 2, more preferably when m6 is 0—an aryl or heteroaryl, in each case unsubstituted or mono- or polysubstituted with at least one substituent selected from the group consisting of F, Cl, Br, I, OH, an O—$C_{1-4}$ aliphatic residue, OCF$_2$H, OCF$_3$, CF$_3$, CN, a $C_{1-4}$-aliphatic residue, C(=O)—CH$_3$, C(=O)—C$_2$H$_5$, CH$_2$—OH, CH$_2$—OCH$_3$, S(=O)$_2$—CH$_3$, SCF$_3$, NO$_2$, N($C_{1-4}$ aliphatic residue)$_2$,

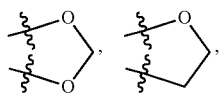

C(=O)—O—CH$_3$ and C(=O)—O—C$_2$H$_5$, a $C_{3-6}$ cycloaliphatic residue, a 3 to 6 membered heterocycloaliphatic residue, benzyl, phenyl, thienyl or pyridyl, preferably denotes—preferably when m6 is 0 or 2, more preferably when m6 is 0—an aryl or heteroaryl, in each case unsubstituted or mono- or polysubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$ and C(=O)—O—C$_2$H$_5$, a $C_{3-6}$ cycloaliphatic residue, a 3 to 6 membered heterocycloaliphatic residue, benzyl, phenyl, thienyl or pyridyl,
wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, OCF$_3$, CF$_3$, CN, a $C_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, OCF$_3$, CF$_3$ a $C_{1-4}$-aliphatic residue and C(=O)—OH.

In a further preferred embodiment of the compound according to general formula (6-I), the residue $R^{601}$ represents the partial structure (6-T1),
wherein
m6 is 0, 1 or 2, preferably 0 or 2, more preferably 2, and
$R^{612a}$ and $R^{612b}$ each independently of one another represent H, F, OH, a O—$C_{1-4}$ aliphatic residue or a $C_{1-4}$ aliphatic residue or together denote =O; preferably H, F, OH, CH$_3$ or OCH$_3$ or together denote =O;
$R^{612c}$ denotes a $C_{1-4}$ aliphatic residue, unsubstituted or mono- or polysubstituted with at least one substituent selected from the group consisting of F, Cl, Br, I, CN, OH, an unsubstituted O—$C_{1-4}$ aliphatic residue, an unsubstituted S(=O)$_2$—$C_{1-4}$ aliphatic residue, CF$_3$, and an unsubstituted $C_{1-4}$-aliphatic residue, preferably denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, CF$_3$, and an unsubstituted $C_{1-4}$-aliphatic residue
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, CF$_3$, and an unsubstituted $C_{1-4}$-aliphatic residue,
or
wherein
m6 is 0 or 2, more preferably 0, and
$R^{612a}$ and $R^{612b}$ each independently of one another represent H, F, OH, a O—$C_{1-4}$ aliphatic residue or a $C_{1-4}$ aliphatic residue; preferably H, F, OH, CH$_3$ or OCH$_3$; and
$R^{612c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, OCF$_3$, OCF$_2$H, CH$_2$—OH, CH$_2$—OCH$_3$, S(=O)$_2$—CH$_3$, SCF$_3$, NO$_2$, N($C_{1-4}$ aliphatic residue)$_2$,

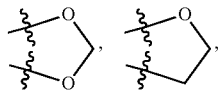

CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, preferably denotes an aryl or heteroaryl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$.

Preferably,

R$^{601}$ represents the partial structure (6-T1),
wherein
m6 is 0, 1 or 2, preferably 0 or 2, more preferably 2, and R$^{612a}$ and R$^{612b}$ each independently of one another represent H, F, OH, CH$_3$ or OCH$_3$ or together denote =O, more preferably H, F, OH or CH$_3$, even more preferably H, R$^{612c}$ denotes a C$_{1-4}$ aliphatic residue, preferably methyl, ethyl, n-propyl, 2-propyl, n-butyl, isobutyl, sec-butyl, or tert-butyl, unsubstituted or mono- or polysubstituted with at least one substituent selected from the group consisting of F, Cl, Br, I, CN, OH, S(=O)$_2$—CH$_3$, an unsubstituted O—C$_{1-4}$ aliphatic residue, preferably O-methyl and O-tert.-butyl, and CF$_3$, preferably denotes a C$_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, an unsubstituted O—C$_{1-4}$ aliphatic residue, preferably O-methyl and O-tert-butyl, and CF$_3$, or denotes a C$_{3-10}$-cycloaliphatic residue or a 3 to 10 membered heterocycloaliphatic residue, preferably cyclopropyl, cyclopentyl, cyclohexyl, morpholinyl, oxetanyl, or tetrahydropyranyl, in each case unsubstituted or mono- or polysubstituted with at least one substituent selected from the group consisting of F, Cl, Br, I, an unsubstituted O—C$_{1-4}$ aliphatic residue, preferably O-methyl and O-ethyl, CF$_3$, and an unsubstituted C$_{1-4}$-aliphatic residue, preferably methyl or ethyl, or
wherein
m6 is 0 or 2, more preferably 0, and
R$^{612a}$ and R$^{612b}$ each independently of one another represent H, F, OH, CH$_3$ or OCH$_3$; preferably H, OH or CH$_3$, and
R$^{612c}$ denotes an aryl or heteroaryl, preferably phenyl or pyridyl, in each case unsubstituted or mono- or polysubstituted with at least one substituent selected from the group consisting of F, Cl, Br, I, OH, an O—C$_{1-4}$ aliphatic residue, preferably OCH$_3$, OCF$_3$, OCF$_2$H, CH$_2$—OH, CH$_2$—OCH$_3$, S(=O)$_2$—CH$_3$, SCF$_3$, NO$_2$, N(CH$_3$)$_2$,

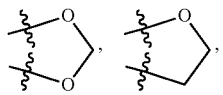

CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, preferably denotes an aryl or heteroaryl, preferably phenyl or pyridyl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$.

Particularly preferred is a compound according to general formula (I) which has the following general formula (6-I-d),

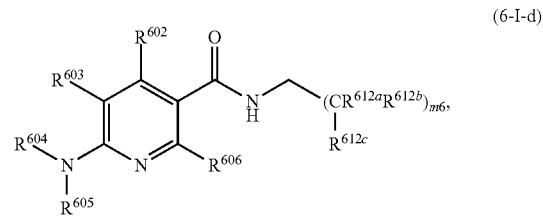

(6-I-d)

wherein the particular radicals and parameters have the meanings described herein in connection with the compounds according to the invention and preferred embodiments thereof.

In a preferred embodiment of the compound according to general formula (6-I), the residue R$^{602}$ represents F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$ aliphatic residue may be in each case be unsubstituted or mono- or polysubstituted; a C$_{3-6}$-cycloaliphatic residue or a 3 to 6 membered heterocycloaliphatic residue, in each case unsubstituted or mono- or polysubstituted and in each case optionally bridged via a C$_{1-4}$ aliphatic group, which in turn may be unsubstituted or mono- or polysubstituted.

Preferably,

R$^{602}$ represents F; Cl; Br; I; CN; CF$_3$; NO$_2$; OCF$_3$; SCF$_3$; a C$_{1-4}$-aliphatic residue, a S—C$_{1-4}$-aliphatic residue, a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—C$_{1-4}$-aliphatic residue, a C$_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a C$_{1-4}$-aliphatic residue and a O—C$_{1-4}$-aliphatic residue, wherein the C$_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably, $R^{602}$ represents F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, cyclopropyl, cyclobutyl, cyclopentyl, cyclohexyl, pyrrolidinyl, piperazinyl, 4-nnethylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably, $R^{602}$ represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; $CH_2$—OH; $CH_2$—O—$CH_3$; $CH_2$—$CH_2$—OH; $CH_2$—$CH_2$—$OCH_3$; O-methyl; O-ethyl; O—$(CH_2)_2$—O—$CH_3$; O—$(CH_2)_2$—OH; S-Methyl; S-ethyl; cyclopropyl, cyclobutyl, cyclopentyl, and cyclohexyl; preferably represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-ethyl; cyclopropyl, cyclobutyl, cyclopentyl, and cyclohexyl.

Still more preferably, $R^{602}$ is selected from the group consisting of F; Cl; $CF_3$; CN; $SCF_3$; $OCF_3$; $CH_3$; $C_2H_5$; n-propyl; iso-propyl; t-butyl; $CH_2$—OH; $CH_2$—O—$CH_3$; cyclopropyl; O—$CH_3$ and O—$C_2H_5$; preferably is selected from the group consisting of F; Cl; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$.

In particular, $R^{602}$ is selected from the group consisting of F; Cl; $CF_3$; $CH_3$; $C_2H_5$, iso-propyl; $CH_2$—O—$CH_3$; cyclopropyl; and O—$CH_3$; preferably is selected from the group consisting of F; Cl; $CF_3$; $CH_3$; $C_2H_5$, iso-propyl; cyclopropyl; and O—$CH_3$.

More particular, $R^{602}$ is selected from the group consisting of $CF_3$; $CH_3$; $C_2H_5$, iso-propyl; $0H_2$—O—$CH_3$; and O—$CH_3$; preferably is selected from the group consisting of $CH_3$; $C_2H_5$, iso-propyl; $CH_2$—O—$CH_3$; and O—$CH_3$.

In a particular preferred embodiment of the compound according to general formula (6-I), the residue $R^{602}$ denotes $CH_3$ or $CF_3$, most preferably $R^{602}$ denotes $CH_3$.

In a further preferred embodiment of the compound according to general formula (6-I), the residue $R^{603}$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue;

a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

Preferably, $R^{603}$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted with at least one substituent selected from the group consisting of F, Cl, Br, I, =O, OH, and an unsubstituted O—$C_{1-4}$-aliphatic residue.

More preferably, $R^{603}$ represents H; F; Cl; Br; I; CN; $CF_3$; $SCF_3$; $NO_2$; $OCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; or S-Ethyl.

Even more preferably $R^{603}$ represents H; F; Cl; Br; I; CN; $CF_3$; $SCF_3$; $OCF_3$; methyl; ethyl; O-methyl; or O-ethyl, preferably represents H; F; Cl; Br; I; $CF_3$; $SCF_3$; $OCF_3$; methyl; ethyl; O-methyl; or O-ethyl.

Still more preferably $R^{603}$ represents H; F; Cl; Br; CN; $CF_3$; $SCF_3$; $OCF_3$; O-methyl or methyl, preferably represents H; F; Cl; $CF_3$; $SCF_3$; $OCF_3$; O-methyl or methyl.

In particular $R^{603}$ represents H; F; Cl; Br; CN; or methyl, preferably H, F, Cl, Br or CN, more preferably H, Cl or Br, most preferably H.

In a further preferred embodiment of the compound according to general formula (6-I), the residue $R^{604}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$- aliphatic residue, $CF_3$, CN, a $C_{1-4}$-aliphatic residue, a $C(=O)$—O—$C_{1-4}$-aliphatic residue, and $C(=O)$—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, $C(=O)$—OH, a $C(=O)$—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and $C(=O)$—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, a $C(=O)$—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and $C(=O)$—OH, on the condition that if $R^{604}$ denotes a 3 to 10 membered heterocycloaliphatic residue, the 3 to 10 membered heterocycloaliphatic residue is linked via a carbon atom, or denotes an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, $C(=O)$—OH, $C(=O)$—$CH_3$, $C(=O)$—$C_2H_5$, $C(=O)$—O—$CH_3$ and $C(=O)$—O—$C_2H_5$, a $C_{3-6}$ cycloaliphatic residue, a 3 to 6 membered heterocycloaliphatic residue,

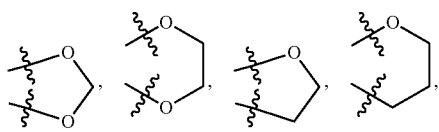

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, $C(=O)$—OH, $C(=O)$—$CH_3$, $C(=O)$—$C_2H_5$, $C(=O)$—O—$CH_3$ and $C(=O)$—O—$C_2H_5$, and wherein the $C_{3-5}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and $C(=O)$—OH, and wherein the aryl or the heteroaryl residue may in each case be optionally bridged, preferably in each case is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and $C(=O)$—OH, $R^{605}$ denotes H or a $C_{1-10}$-aliphatic residue, preferably a $C_{1-4}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and $C(=O)$—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or $R^{604}$ and $R^{605}$ form together with the nitrogen atom connecting them a 3 to 10 membered heterocycloaliphatic residue, preferably a 4 to 7 membered heterocycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, $C(=O)$—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, =O, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, and wherein the 3 to 10 membered heterocycloaliphatic residue formed by R$^4$ and R$^5$ together with the nitrogen atom connecting them may optionally be condensed with aryl or heteroaryl, preferably with phenyl, pyridyl or thienyl, wherein the aryl or heteroaryl residues condensed in this way can for their part be respectively unsubstituted or mono- or polysubstituted with at least one substituent selected from the group consisting of F, Cl, Br, I, NO$_2$, NH$_2$, an NH(C$_1$-4 aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

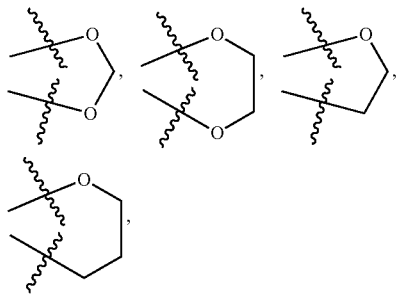

benzyl, phenyl, thienyl, pyridyl, furyl, thiazolyl and oxazolyl, and wherein the 3 to 10 membered heterocycloaliphatic residue formed by R$^4$ and R$^5$ together with the nitrogen atom connecting them may optionally be condensed with a C$_{3-10}$ cycloaliphatic residue or a 3 to 10 membered heterocycloaliphatic residue, wherein the C$_{3-10}$ cycloaliphatic residue or a 3 to 10 membered heterocycloaliphatic residue condensed in this way can for their part be respectively unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, =O, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue, benzyl, phenyl, thienyl, pyridyl, furyl, thiazolyl and oxazolyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

In a further preferred embodiment of the compound according to general formula (6-I), the residue R$^{604}$ represents the partial structure (6-T2)

wherein n6 denotes 0, 1, 2, or 3, preferably denotes 1, 2 or 3, more preferably denotes 1 or 2, even more preferably denotes 1, R$^{613a}$ and R$^{613b}$ each independently of one another represent H, F, Cl, Br, I, NO$_2$, NH$_2$, a NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$ aliphatic residue or C(=O)—OH, or together denote =O, preferably each independently of one another represent H, F, Cl, Br, I, NH$_2$, a NH(C$_{1-4}$ aliphatic residue), a N(C$_{1-4}$ aliphatic residue)$_2$, OH, O—C$_{1-4}$ aliphatic residue or a C$_{1-4}$ aliphatic residue or together denote =O, more preferably each independently of one another represent H, F, Cl, Br, I, an O—C$_{1-4}$ aliphatic residue or a C$_{1-4}$ aliphatic residue or together denote =O, even more preferably each independently of one another represent H, F, an O—C$_{1-4}$ aliphatic residue or a C$_{1-4}$ aliphatic residue or together denote =O, and R$^{613c}$ denotes a C$_{1-4}$ aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH, or denotes—preferably when n6 is ≠0, more preferably when n is 1—a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue and a 3 to 6 membered heterocycloaliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when n6 is ≠0, more preferably when n6 is 1,—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

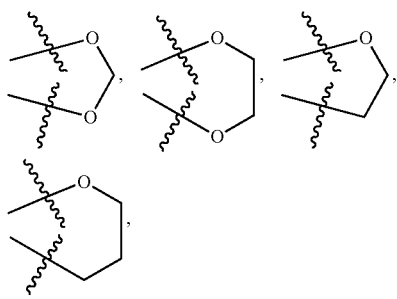

benzyl, phenyl, thienyl, pyridyl, furyl, thiazolyl and oxazolyl,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
  wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, $R^{605}$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, or
$R^{604}$ and $R^{605}$ form together with the nitrogen atom connecting them a 3 to 10 membered heterocycloaliphatic residue, preferably a 4 to 7 membered heterocycloaliphatic residue, or preferably selected from the group consisting of morpholinyl, piperidinyl, pyrrolidinyl, azetidinyl, piperazinyl, 4-methylpiperazinyl, oxazepanyl, thiomorpholinyl, azepanyl,

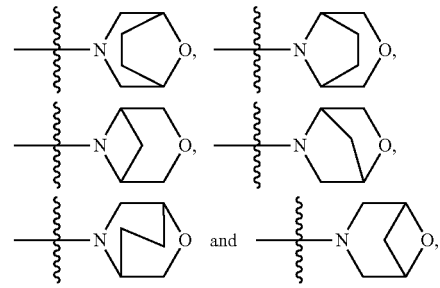

more preferably selected from the group consisting of morpholinyl, piperidinyl, pyrrolidinyl, azetidinyl, piperazinyl, 4-methylpiperazinyl, oxazepanyl, in each case unsubstituted or mono- or polysubstituted with at least one substituent selected from the group consisting of F, Cl, Br, I, $NO_2$, OH, =O, C(=O)—OH, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, a $C_{3-6}$ cycloaliphatic residue, preferably cyclopropyl, cyclobutyl or cyclopentyl, and a 3 to 6 membered heterocycloaliphatic residue,
  wherein the $C_{1-4}$-aliphatic residue in each case may be unsubstituted or mono- or polysubstituted with at least one substituent selected from the group consisting of F, Cl, Br, I, =O, OH, $CF_3$ and an unsubstituted O—$C_{1-4}$-aliphatic residue, preferably selected from the group consisting of F, Cl, Br, I, OH, $CF_3$ and an unsubstituted O—$C_{1-4}$-aliphatic residue,
  wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the 3 to 10 membered heterocycloaliphatic residue formed by $R^4$ and $R^5$ together with the nitrogen atom connecting them may optionally be condensed with aryl or heteroaryl, preferably with phenyl, pyridyl or thienyl, wherein the aryl or heteroaryl residues condensed in this way can for their part be respectively unsubstituted or mono- or polysubstituted with at least one substituent selected from the group consisting of F, Cl, Br, I, $NO_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, a 3 to 6 membered heterocycloaliphatic residue,

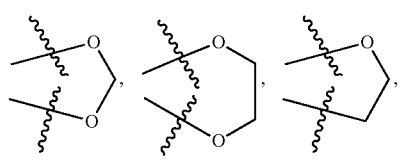

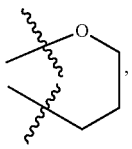

benzyl, phenyl, thienyl, and pyridyl,
and wherein the 3 to 10 membered heterocycloaliphatic residue formed by $R^4$ and $R^5$ together with the nitrogen atom connecting them may optionally be condensed with a $C_{3-10}$ cycloaliphatic residue, preferably cyclopropyl, cyclobutyl or cyclopentyl, or a 3 to 10 membered heterocycloaliphatic residue, preferably oxetanyl or oxiranyl, wherein the $C_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, =O, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein benzyl, phenyl, thienyl, and pyridyl, may in each case may be unsubstituted or mono- or polysubstituted with at least one substituent selected from the group consisting of F, Cl, Br, I, $NO_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, and C(=O)—OH, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.
Preferably,
$R^{604}$ represents the partial structure (6-T2),
wherein
n6 denotes 0, 1, 2, or 3, preferably denotes 1, 2 or 3, more preferably denotes 1 or 2, even more preferably denotes 1,
$R^{613a}$ and $R^{613b}$ each independently of one another represent H, F, Cl, Br, I, an O—$C_{1-4}$ aliphatic residue or a $C_{1-4}$ aliphatic residue or together denote =O, preferably each independently of one another represent H, F, a O—$C_{1-2}$ aliphatic residue or a $C_{1-2}$ aliphatic residue or together denote =O, and
$R^{613c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes—preferably when n6 is ≠0, more preferably when n6 is 1—a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue, C(=O)—OH, a $C_{3-6}$ cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH,
or denotes—preferably when n6 is ≠0, more preferably when n6 is 1—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl or oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$,
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$ a $C_{1-4}$-aliphatic residue and C(=O)—OH,
$R^{605}$ denotes H or a $C_{1-6}$-aliphatic residue, preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue,
wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
or
$R^{604}$ and $R^{605}$ form together with the nitrogen atom connecting them a 3 to 10 membered heterocycloaliphatic residue, preferably a 4 to 7 membered heterocycloaliphatic residue, or preferably selected from the group consisting of morpholinyl, piperidinyl, pyrrolidinyl, azetidinyl, piperazinyl, 4-methylpiperazinyl, oxazepanyl, thiomorpholinyl, azepanyl,

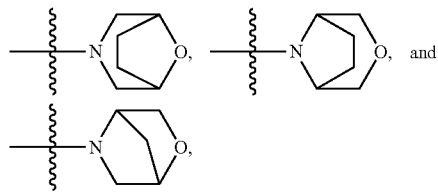

more preferably selected from the group consisting of morpholinyl, piperidinyl, pyrrolidinyl, azetidinyl, piperazinyl, 4-methylpiperazinyl, oxazepanyl, unsubstituted or mono- or polysubstituted with at least one substituent selected from the group consisting of F, Cl, Br, I, OH, =O, C(=O)—OH, an O—$C_{1-4}$ aliphatic residue, $OCF_3$, $SCF_3$, a S—$C_{1-4}$ aliphatic residue, $CF_3$, and a $C_{1-4}$-aliphatic residue, and a $C_{3-6}$ cycloaliphatic residue, preferably cyclopropyl, cyclobutyl or cyclopentyl, wherein the $C_{1-4}$-aliphatic residue in each case may be unsubstituted or mono- or polysubstituted with at least one substituent selected from the group consisting of F, Cl, Br, I, OH, =O, $CF_3$ and an unsubstituted O—$C_{1-4}$-aliphatic residue, preferably selected from the group consisting of F, Cl, Br, I, OH, $CF_3$ and an unsubstituted O—$C_{1-4}$-aliphatic residue, wherein the $C_{3-6}$ cycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, $CF_3$, CN, a $C_{1-4}$-aliphatic residue and C(=O)—OH, and wherein the 3 to 10 membered heterocycloaliphatic residue formed by $R^{604}$ and $R^{605}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, OH, an O—$C_{1-4}$ aliphatic residue, $OCF_3$, $SCF_3$, a S—$C_{1-4}$ aliphatic residue, $CF_3$, a $C_{1-4}$-aliphatic residue, C(=O)—OH, a $C_{3-6}$ cycloaliphatic residue, benzyl, phenyl, thienyl, and pyridyl, and wherein the 3 to 10 membered heterocycloaliphatic residue formed by $R^{604}$ and $R^{605}$ together with the nitrogen atom connecting them may optionally be condensed with a $C_{3-10}$ cycloaliphatic residue, preferably cyclopropyl, cyclobutyl or cyclopentyl, or a 3 to 10 membered heterocycloaliphatic residue, preferably oxetanyl or oxiranyl, wherein the $C_{3-10}$ cycloaliphatic residue or the 3 to 10 membered heterocycloaliphatic residue condensed in this way can for their part be respectively unsubstituted or mono- or polysubstituted with at least one substituent selected from the group consisting of F, Cl, Br, I, =O, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, OH, an O—$C_{1-4}$ aliphatic residue, $OCF_3$, O—$CH_2$—OH, O—$CH_2$—O—$CH_3$, $SCF_3$, a S—$C_{1-4}$ aliphatic residue, $CF_3$, CN, a $C_{1-4}$-aliphatic residue, and C(=O)—OH, and wherein the $C_{3-6}$ cycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, $CF_3$, a $C_{1-4}$-aliphatic residue and C(=O)—OH.

More preferably, $R^{604}$ represents the partial structure (6-T2), wherein n6 denotes 0, 1, 2 or 3, preferably denotes 1 or 2, more preferably denotes 1, $R^{613a}$ and $R^{613b}$ each independently of one another represent H, F, Cl, Br, I, an O—$C_{1-4}$ aliphatic residue or a $C_{1-4}$ aliphatic residue or together denote =O, preferably each independently of one another represent H, F, a O—$C_{1-2}$ aliphatic residue or a $C_{1-2}$ aliphatic residue or together denote =O, and $R^{613c}$ denotes a $C_{1-4}$ aliphatic residue, unsubstituted or mono- or polysubstituted with at least one substituent selected from the group consisting of F, Cl, Br, I, =O, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, CH$_3$, O—CH$_3$, CF$_3$ and OCF$_3$, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, CF$_3$ a C$_{1-4}$-aliphatic residue and C(=O)—OH, R$^{605}$ denotes H or an unsubstituted C$_{1-4}$-aliphatic residue or a C$_{1-4}$-aliphatic residue monosubstituted with O-methyl, wherein the C$_{1-4}$-aliphatic residue is in each case preferably selected from the group consisting of methyl, ethyl, n-propyl, 2-propyl, n-butyl, isobutyl, sec.-butyl and tert.-butyl, more preferably selected from the group consisting of methyl and ethyl, or R$^{604}$ and R$^{605}$ form together with the nitrogen atom connecting them a 3 to 10 membered heterocycloaliphatic residue, more preferably selected from the group consisting of morpholinyl, piperidinyl, pyrrolidinyl, azetidinyl, piperazinyl, 4-methylpiperazinyl, oxazepanyl, thiomorpholinyl, azepanyl,

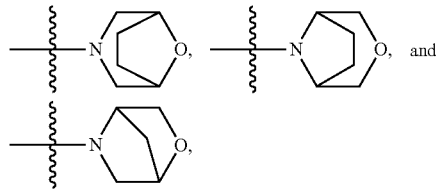

in each case unsubstituted or mono- or polysubstituted with at least one substituent selected from the group consisting of F, Cl, Br, I, OH, =O, C(=O)—OH, an O—C$_{1-4}$ aliphatic residue, OCF$_3$, SCF$_3$, a S—C$_{1-4}$ aliphatic residue, CF$_3$, and a C$_{1-4}$-aliphatic residue, cyclopropyl, cyclobutyl and cyclopentyl, wherein the C$_{1-4}$-aliphatic residue is in each case unsubstituted or mono- or polysubstituted with at least one substituent selected from the group consisting of F, Cl, OH, =O, CF$_3$ and an unsubstituted O—C$_{1-4}$-aliphatic residue, preferably is in each case unsubstituted, and wherein the 3 to 10 membered heterocycloaliphatic residue formed by R$^{604}$ and R$^{605}$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, Br, I, OH, an O—C$_{1-4}$ aliphatic residue, OCF$_3$, SCF$_3$, a S—C$_{1-4}$ aliphatic residue, CF$_3$, a C$_{1-4}$-aliphatic residue, C(=O)—OH, and a C$_{3-6}$ cycloaliphatic residue, wherein the C$_{1-4}$-aliphatic residue in each case may be unsubstituted or mono- or polysubstituted with at least one substituent selected from the group consisting of F, Cl, OH, OCF$_3$, CF$_3$ and an unsubstituted O—C$_{1-4}$-aliphatic residue, and wherein the C$_{3-6}$ cycloaliphatic residue may in each case may be unsubstituted or mono- or polysubstituted with at least one substituent selected from the group consisting of F, Cl, Br, I, OH, =O, an O—C$_{1-4}$ aliphatic residue, OCF$_3$, SCF$_3$, a S—C$_{1-4}$ aliphatic residue, CF$_3$, a C$_{1-4}$-aliphatic residue and C(=O)—OH, and wherein the 3 to 10 membered heterocycloaliphatic residue formed by R$^{604}$ and R$^{605}$ together with the nitrogen atom connecting them may optionally be condensed with a C$_{3-6}$ cycloaliphatic residue, preferably cyclopropyl, cyclobutyl or cyclopentyl, or a 4 to 7 membered heterocycloaliphatic residue, preferably oxetanyl or oxiranyl, wherein the C$_{3-6}$ cycloaliphatic residue or the 4 to 7 membered heterocycloaliphatic residue condensed in this way can for their part be respectively unsubstituted or mono- or polysubstituted with at least one substituent selected from the group consisting of F, Cl, Br, I, =O, OH, an O—C$_{1-4}$ aliphatic residue, OCF$_3$, SCF$_3$CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$.

Even more preferably,

R$^{604}$ represents the partial structure (I-T2), wherein n6 denotes 0, 1, 2 or 3, preferably denotes 1 or 2, more preferably denotes 1, R$^{613a}$ and R$^{613b}$ each independently of one another represent H, F, a O—C$_{1-4}$ aliphatic residue or a C$_{1-4}$ aliphatic residue or together denote =O; preferably each independently of one another represent H, F, CH$_3$ or OCH$_3$ or together denote =O;

R$^{613c}$ denotes a C$_{1-4}$ aliphatic residue, unsubstituted or mono- or polysubstituted with at least one substituent selected from the group consisting of F, Cl, Br, I, =O, an unsubstituted O—C$_{1-4}$ aliphatic residue, CF$_3$, and an unsubstituted C$_{1-4}$-aliphatic residue, or denotes a C$_{3-10}$-cycloaliphatic residue, preferably selected from the group consisting of cyclopropyl, cyclobutyl, cyclopentyl and cyclohexyl, or a 3 to 10 membered heterocycloaliphatic residue, preferably selected from the group consisting of pyrrolidinyl, morpholinyl, piperazinyl, piperidinyl and tetrahydropyranyl, more preferably tetrahydropyranyl, in each case unsubstituted or mono- or polysubstituted with at least one substituent selected from the group consisting of F, Cl, Br, I, an unsubstituted O—C$_{1-4}$ aliphatic residue, CF$_3$, and an unsubstituted C$_{1-4}$-aliphatic residue, or denotes an aryl or heteroaryl, preferably phenyl or pyridyl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, R$^{605}$ denotes H or an unsubstituted C$_{1-4}$-aliphatic residue or a C$_{1-4}$-aliphatic residue, which is monosubstituted with OCH$_3$, preferably H, methyl, ethyl, n-propyl, 2-propyl, n-butyl, isobutyl, sec.-butyl or tert.-butyl or CH$_2$—OCH$_3$, C$_2$H$_4$—OCH$_3$ or C$_3$H$_6$—OCH$_3$, more preferably H, methyl or ethyl, preferably denotes H or an unsubstituted $C_{1-4}$-aliphatic residue, preferably H, methyl, ethyl, n-propyl, 2-propyl, n-butyl, isobutyl, sec.-butyl or tert.-butyl, more preferably H, methyl or ethyl, or $R^{604}$ and $R^{605}$ form together with the nitrogen atom connecting them a morpholinyl, piperidinyl, pyrrolidinyl, azetidinyl, piperazinyl, 4-methylpiperazinyl, oxazepanyl, thiomorpholinyl, azepanyl,

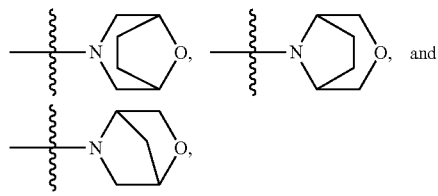

tetrahydroquinolinyl, tetrahydroisoquinolinyl, tetrahydroinnidazo[1,2-a]pyrazinyl, octahydropyrrolo[1,2-a]pyrazinyl,

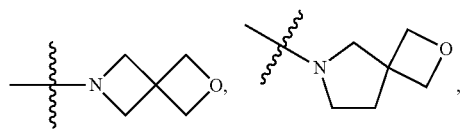 [SMILES: *N1CC2(COC2)C1 ; *N1CCC2(COC2)C1 ; ","]

dihydroindolinyl, or dihydroisoindolyl, preferably a morpholinyl, piperidinyl, pyrrolidinyl, azetidinyl, piperazinyl, 4-methylpiperazinyl, oxazepanyl, tetrahydroquinolinyl, tetrahydroisoquinolinyl, dihydroindolinyl, or dihydroisoindolyl, in each case unsubstituted or mono- or polysubstituted with at least one substituent selected from the group consisting of F, Cl, Br, I, OH, =O, C(=O)—OH, an O—$C_{1-4}$ aliphatic residue, $OCF_3$, $SCF_3$, a S—$C_{1-4}$ aliphatic residue, $CF_3$, and a $C_{1-4}$-aliphatic residue, cyclopropyl, cyclobutyl and cyclopentyl, wherein the $C_{1-4}$-aliphatic residue is in each case unsubstituted or mono- or polysubstituted with at least one substituent selected from the group consisting of F, OH, =O, $CF_3$ and an unsubstituted O—$C_{1-4}$-aliphatic residue, preferably is in each case unsubstituted.

Still more preferably, $R^{604}$ represents the partial structure (6-T2), wherein n6 denotes 0, 1, 2 or 3, preferably denotes 1 or 2, more preferably denotes 1, $R^{613a}$ and $R^{613b}$ each independently of one another represent H, F, $CH_3$ or $OCH_3$ or together denote =O, preferably each independently of one another represent H or $CH_3$, more preferably H, $R^{613c}$ denotes a $C_{1-4}$ aliphatic residue, preferably methyl, ethyl, n-propyl, 2-propyl, n-butyl, isobutyl, sec-butyl, or tert-butyl, unsubstituted or mono- or polysubstituted with at least one substituent selected from the group consisting of F, Cl, Br, I, =O, an unsubstituted O—$C_{1-4}$ aliphatic residue, and $CF_3$, or denotes cyclopropyl, cyclobutyl, cyclopentyl or cyclohexyl, pyrrolidinyl, morpholinyl, piperazinyl, piperidinyl and tetrahydropyranyl, more preferably tetrahydropyranyl or morpholinyl, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or denotes an aryl or heteroaryl, preferably phenyl or pyridyl, more preferably phenyl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, and a $C_{1-4}$-aliphatic residue, $R^{605}$ denotes H, methyl or ethyl or $C_2H_4OCH_3$ or $C_3H_6OCH_3$, more preferably H or methyl or ethyl, even more preferably methyl, or $R^{604}$ and $R^{605}$ form together with the nitrogen atom connecting them a morpholinyl, piperidinyl, pyrrolidinyl, azetidinyl, oxazepanyl, tetrahydroquinolinyl, tetrahydroisoquinolinyl, thiomorpholinyl, azepanyl,

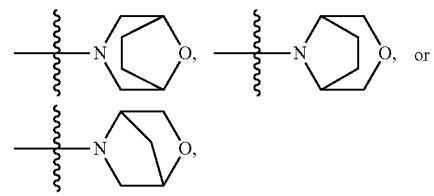

tetrahydroinnidazo[1,2-a]pyrazinyl, octahydropyrrolo[1,2-a]pyrazinyl,

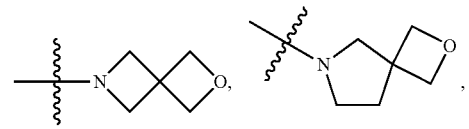 [SMILES: *N1CC2(COC2)C1 ; *N1CCC2(COC2)C1 ; ","]

dihydroindolinyl, or dihydroisoindolyl, preferably a a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, more preferably a morpholinyl, piperidinyl, pyrrolidinyl, azetidinyl, oxazepanyl, tetrahydroquinolinyl, tetrahydroisoquinolinyl, more preferably a morpholinyl, oxazepanyl, tetrahydroquinolinyl, or tetrahydroisoquinolinyl, in each case unsubstituted or mono- or polysubstituted with at least one substituent selected from the group consisting of F, Cl, OH, =O, C(=O)—OH, C(=O)—$CH_3$, C(=O)—$OCH_3$, O-methyl, O-ethyl, $OCF_3$, $SCF_3$, $CF_3$, methyl, $CH_2CF_3$, $CH_2OH$, $CH_2$—$OCH_3$, $CH_2CH_2$—$OCH_3$, ethyl, n-propyl, 2-propyl, cyclopropyl, and cyclobutyl, preferably selected from the group consisting of F, Cl, OH, =O, C(=O)—OH, O-methyl, O-ethyl, $OCF_3$, $SCF_3$, $CF_3$, methyl, ethyl, n-propyl, 2-propyl, cyclopropyl, and cyclobutyl.

In a preferred embodiment of the compound according to general formula (6-I), the residue $R^{606}$ denotes a $C_{2-10}$-aliphatic residue, preferably a $C_{2-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{606}$ denotes a 3 to 10 membered heterocycloaliphatic residue, the binding is carried out via a carbon atom of the 3 to 10 membered heterocycloaliphatic residue, or $R^{606}$ denotes S—$R^{607}$, O—$R^{608}$ or $N(R^{609}R^{610})$, wherein $R^{607}$ and $R^{608}$ in each case represent a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or in each case represent a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{607}$ or $R^{608}$ denotes a 3 to 10 membered heterocycloaliphatic residue, the binding is carried out via a carbon atom of the 3 to 10 membered heterocycloaliphatic residue, $R^{609}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{609}$ denotes a 3 to 10 membered heterocycloaliphatic residue, the binding is carried out via a carbon atom of the 3 to 10 membered heterocycloaliphatic residue, $R^{610}$ denotes H or a $C_{1-10}$-aliphatic residue, preferably a $C_{1-4}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, preferably denotes a $C_{1-10}$-aliphatic residue, more preferably a $C_{1-4}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or $R^{609}$ and $R^{610}$ form together with the nitrogen atom connecting them a 3 to 10 membered heterocycloaliphatic residue, preferably a 3 to 6 membered heterocycloaliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the 3 to 10 membered heterocycloaliphatic residue formed by $R^{609}$ and $R^{610}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

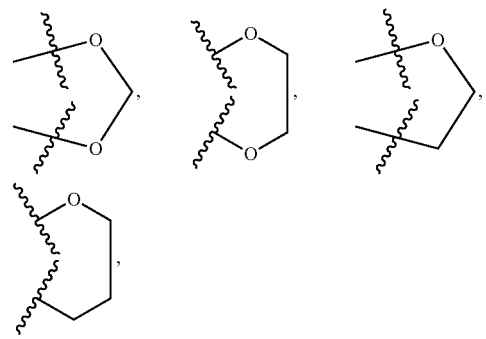

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue$)_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

Preferably, $R^{606}$ denotes a $C_{2-10}$-aliphatic residue, preferably a $C_m$-aliphatic residue, unsubstituted or mono- or polysubstituted with at least one substituent selected from the group consisting of F, Cl, Br, I, $NO_2$, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, NO$_2$, OH, =O, an O—$C_{1-4}$ aliphatic residue, a C(=O)—O—$C_{1-4}$-aliphatic residue, OCF$_3$, SH, SCF$_3$, a S—$C_{1-4}$ aliphatic residue, CF$_3$, CN, and a $C_{1-4}$-aliphatic residue.

on the condition that if $R^{606}$ denotes a 3 to 10 membered heterocycloaliphatic residue, the 3 to 10 membered heterocycloaliphatic residue is linked via a carbon atom, or $R^{606}$ denotes S—$R^{607}$ or O—$R^{608}$, wherein $R^{607}$ and $R^{608}$ in each case represent a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, OCF$_3$, SH, SCF$_3$, a S—$C_{1-4}$-aliphatic residue, an NH($C_{1-4}$ aliphatic residue), an N($C_{1-4}$ aliphatic residue)$_2$, a C(=O)—O—$C_{1-4}$-aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue, or in each case denote a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a C(=O)—O—$C_{1-4}$-aliphatic residue, a S—$C_{1-4}$ aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, OCF$_3$, SH, SCF$_3$, a S—$C_{1-4}$ aliphatic residue, a C(=O)—O—$C_{1-4}$-aliphatic residue, CF$_3$, CN, and a $C_{1-4}$-aliphatic residue.

on the condition that if $R^{607}$ or $R^{608}$ denotes a 3 to 10 membered heterocycloaliphatic residue, the 3 to 10 membered heterocycloaliphatic residue is linked via a carbon atom, or $R^{606}$ denotes N($R^{609}R^{610}$), wherein $R^{609}$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, OCF$_3$, SH, SCF$_3$, a S—$C_{1-4}$-aliphatic residue, a C(=O)—O—$C_{1-4}$-aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a C(=O)—O—$C_{1-4}$-aliphatic residue, a S—$C_{1-4}$ aliphatic residue, CF$_3$, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, OCF$_3$, SH, SCF$_3$, a S—$C_{1-4}$ aliphatic residue, a C(=O)—O—$C_{1-4}$-aliphatic residue, CF$_3$, CN, and a $C_{1-4}$-aliphatic residue, on the condition that if $R^{609}$ denotes a 3 to 10 membered heterocycloaliphatic residue, the 3 to 10 membered heterocycloaliphatic residue is linked via a carbon atom, and $R^{610}$ denotes H or a $C_{1-10}$-aliphatic residue, preferably a $C_{1-6}$-aliphatic residue, unsubstituted or mono- or polysubstituted with at least one substituent selected from the group consisting of F, Cl, Br, I, NO$_2$, OH, =O, an O—$C_{1-4}$ aliphatic residue, OCF$_3$, SH, SCF$_3$, a S—$C_{1-4}$ aliphatic residue, CF$_3$, CN, and a $C_{1-4}$-aliphatic residue, preferably denotes a $C_{1-10}$-aliphatic residue, more preferably a $C_{1-6}$-aliphatic residue, unsubstituted or mono- or polysubstituted with at least one substituent selected from the group consisting of F, Cl, Br, I, NO$_2$, OH, =O, an O—$C_{1-4}$ aliphatic residue, OCF$_3$, SH, SCF$_3$, a S—$C_{1-4}$ aliphatic residue, CF$_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue, or $R^{609}$ and $R^{610}$ form together with the nitrogen atom connecting them a 3 to 10 membered heterocycloaliphatic residue, preferably a 3 to 6 membered heterocycloaliphatic residue, more preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, NO$_2$, OH, =O, an O—$C_{1-4}$ aliphatic residue, OCF$_3$, SH, SCF$_3$, a S—$C_{1-4}$ aliphatic residue, CF$_3$, CN, and a $C_{1-4}$-aliphatic residue, wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—C$_{1-4}$-aliphatic residue, and wherein the 3 to 10 membered heterocycloaliphatic residue formed by R$^{609}$ and R$^{610}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, NO$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, a 3 to 6 membered heterocycloaliphatic residue,

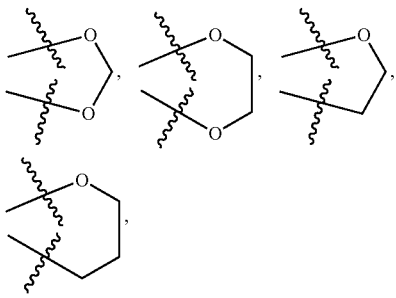

benzyl, phenyl, thienyl, and pyridyl, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein benzyl, phenyl, thienyl, and pyridyl, may in each case may be unsubstituted or mono- or polysubstituted with at least one substituent selected from the group consisting of F, Cl, Br, I, NO$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, and C(=O)—OH, and wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH.

More preferably,

R$^{606}$ denotes a C$_{2-8}$-aliphatic residue, unsubstituted or mono- or polysubstituted with at least one substituent selected from the group consisting of F, Cl, Br, I, OH, =O, an O—C$_{1-4}$-aliphatic residue, OCF$_3$, SH, SCF$_3$, a S—C$_{1-4}$-aliphatic residue, a C(=O)—O—C$_{1-4}$-aliphatic residue, CF$_3$, and a C$_{1-4}$-aliphatic residue, wherein the C$_{1-4}$-aliphatic residue in each case may be unsubstituted or mono- or polysubstituted with at least one substituent selected from the group consisting of F, Cl, Br, I, OH, CF$_3$ and an unsubstituted O—C$_{1-4}$-aliphatic residue, or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—C$_{1-4}$ aliphatic residue, OCF$_3$, SCF$_3$, a C(=O)—O—C$_{1-4}$-aliphatic residue, a S—C$_{1-4}$ aliphatic residue, CF$_3$, and a C$_{1-4}$-aliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-10}$-cycloaliphatic residue or the 3 to 10 membered heterocycloaliphatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, OH, =O, an O—C$_{1-4}$ aliphatic residue, OCF$_3$, SH, SCF$_3$, a S—C$_{1-4}$ aliphatic residue, a C(=O)—O—C$_{1-4}$-aliphatic residue, CF$_3$, CN, and a C$_{1-4}$-aliphatic residue, on the condition that if R$^{606}$ denotes a 3 to 10 membered heterocycloaliphatic residue, the 3 to 10 membered heterocycloaliphatic residue is linked via a carbon atom, or R$^{606}$ denotes S—R$^{607}$ or O—R$^{608}$, wherein R$^{607}$ and R$^{608}$ in each case denote a C$_{1-8}$-aliphatic residue, preferably a C$_{1-6}$-aliphatic residue, unsubstituted or mono- or polysubstituted with at least one substituent selected from the group consisting of F, Cl, Br, I, OH, =O, an O—C$_{1-4}$-aliphatic residue, OCF$_3$, SH, SCF$_3$, a S—C$_{1-4}$-aliphatic residue, an NH(C$_{1-4}$ aliphatic residue), an N(C$_{1-4}$ aliphatic residue)$_2$, CF$_3$, a C(=O)—O—C$_{1-4}$-aliphatic residue, and a C$_{1-4}$-aliphatic residue, wherein the C$_{1-4}$-aliphatic residue in each case may be unsubstituted or mono- or polysubstituted with at least one substituent selected from the group consisting of F, Cl, Br, I, OH, CF$_3$ and an unsubstituted O—C$_{1-4}$-aliphatic residue, or in each case denote a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—C$_{1-4}$ aliphatic residue, OCF$_3$, SCF$_3$, a S—C$_{1-4}$ aliphatic residue, a C(=O)—O—C$_{1-4}$-aliphatic residue, CF$_3$, and a C$_{1-4}$-aliphatic residue, wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and wherein the C$_{3-10}$-cycloaliphatic residue or the 3 to 10 membered heterocycloaliphatic residue may be bridged, preferably is bridged, via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, OH, =O, an O—C$_{1-4}$ aliphatic residue, OCF$_3$, SH, SCF$_3$, a S—C$_{1-4}$ aliphatic residue, a C(=O)—O—C$_{1-4}$-aliphatic residue, CF$_3$, CN, and a C$_{1-4}$-aliphatic residue, on the condition that if R$^{607}$ or R$^{608}$ denotes a 3 to 10 membered heterocycloaliphatic residue, the 3 to 10 membered heterocycloaliphatic residue is linked via a carbon atom, or R$^{606}$ denotes N(R$^{609}$R$^{610}$), wherein
$R^{609}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, $CF_3$, a C(=O)—O—$C_{1-4}$-aliphatic residue, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-10}$-cycloaliphatic residue or the 3 to 10 membered heterocycloaliphatic residue may in each case be bridged, preferably is bridged, via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue,
on the condition that if $R^{609}$ denotes a 3 to 10 membered heterocycloaliphatic residue, the 3 to 10 membered heterocycloaliphatic residue is linked via a carbon atom,
and
$R^{610}$ denotes H or a $C_{1-6}$-aliphatic residue, preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue, preferably denotes a $C_{1-6}$-aliphatic residue, more preferably a $C_{1-4}$-aliphatic residue, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
or
$R^{609}$ and $R^{610}$ form together with the nitrogen atom connecting them a 3 to 10 membered heterocycloaliphatic residue, preferably selected from the group consisting of morpholinyl, piperidinyl, pyrrolidinyl, azetidinyl and piperazinyl, unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue,
  wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
and wherein the 3 to 10 membered heterocycloaliphatic residue formed by $R^{609}$ and $R^{610}$ together with the nitrogen atom connecting them may optionally be condensed with aryl or heteroaryl, preferably with phenyl or pyridyl, wherein the aryl or heteroaryl residues condensed in this way can for their part be respectively unsubstituted or mono- or polysubstituted with at least one substituent selected from the group consisting of F, Cl, Br, I, $NO_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, residue,

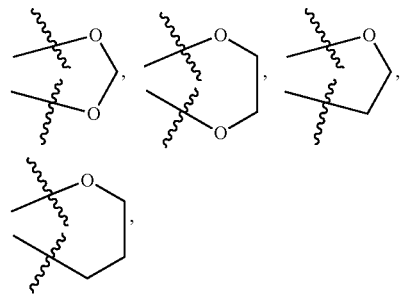

benzyl, phenyl, thienyl, and pyridyl,
  wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue, and
  wherein benzyl, phenyl, thienyl, and pyridyl, may in each case may be unsubstituted or mono- or polysubstituted with at least one substituent selected from the group consisting of F, Cl, Br, I, $NO_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, and C(=O)—OH.
Even more preferably,
$R^{606}$ denotes a $C_{2-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue
  wherein the $C_{1-4}$-aliphatic residue in each case is unsubstituted,
or denotes a $C_{3-10}$-cycloaliphatic residue, preferably a $C_{3-6}$-cycloaliphatic residue, or a 3 to 10 membered heterocycloaliphatic residue, preferably a 3 to 6 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue,
and wherein the $C_{3-10}$-cycloaliphatic residue or the 3 to 10 membered heterocycloaliphatic residue may in each case optionally bridged via a unsubstituted $C_{1-4}$ aliphatic group,
on the condition that if $R^{606}$ denotes a 3 to 10 membered heterocycloaliphatic residue, the 3 to 10 membered heterocycloaliphatic residue is linked via a carbon atom,
or
$R^{606}$ denotes S—$R^{607}$ or O—$R^{608}$,
   wherein
   $R^{607}$ and $R^{608}$ in each case denote a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, OCF$_3$, SH, SCF$_3$, a S—$C_{1-4}$-aliphatic residue, an NH($C_{1-4}$ aliphatic residue), an N($C_{1-4}$ aliphatic residue)$_2$, a C(=O)—O—$C_{1-4}$-aliphatic residue, CF$_3$, and a $C_{1-4}$-aliphatic residue,
      wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue,
   or in each case denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, a C(=O)—O—$C_{1-4}$-aliphatic residue, CF$_3$, and a $C_{1-4}$-aliphatic residue,
      wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and
   wherein the $C_{3-10}$-cycloaliphatic residue or the 3 to 10 membered heterocycloaliphatic residue in each case may be bridged, preferably is bridged, via an unsubstituted $C_{1-8}$ aliphatic group, preferably an unsubstituted $C_{1-4}$ aliphatic group,
   on the condition that if $R^{607}$ or $R^{608}$ denotes a 3 to 10 membered heterocycloaliphatic residue, the 3 to 10 membered heterocycloaliphatic residue is linked via a carbon atom,
or
$R^{606}$ denotes N($R^{609}R^{610}$),
   wherein
   $R^{609}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, OCF$_3$, SH, SCF$_3$, a S—$C_{1-4}$-aliphatic residue, a C(=O)—O—$C_{1-4}$-aliphatic residue, CF$_3$, and a $C_{1-4}$-aliphatic residue,
      wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue,
   or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, OCF$_3$, SCF$_3$, a S—$C_{1-4}$ aliphatic residue, a C(=O)—O—$C_{1-4}$-aliphatic residue, CF$_3$, and a $C_{1-4}$-aliphatic residue,
      wherein the $C_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—$C_{1-4}$-aliphatic residue, and
   wherein the $C_{3-10}$-cycloaliphatic residue or the 3 to 10 membered heterocycloaliphatic residue is in each case bridged via a unsubstituted $C_{1-8}$ aliphatic group, preferably an unsubstituted $C_{1-4}$ aliphatic group,
   on the condition that if $R^{609}$ denotes a 3 to 10 membered heterocycloaliphatic residue, the 3 to 10 membered heterocycloaliphatic residue is linked via a carbon atom, and
   $R^{610}$ denotes H or an unsubstituted $C_{1-4}$-aliphatic residue, preferably selected from the group consisting of methyl, ethyl, n-propyl, 2-propyl, n-butyl, isobutyl, sec.-butyl and tert.-butyl, more preferably selected from the group consisting of methyl and ethyl, preferably denotes an unsubstituted $C_{1-4}$-aliphatic residue, preferably selected from the group consisting of methyl, ethyl, n-propyl, 2-propyl, n-butyl, isobutyl, sec.-butyl and tert.-butyl, more preferably selected from the group consisting of methyl and ethyl,
or
$R^{609}$ and $R^{610}$ form together with the nitrogen atom connecting them a 3 to 6 membered heterocycloaliphatic residue, preferably selected from the group consisting of morpholinyl, piperidinyl, pyrrolidinyl, and azetidinyl, unsubstituted or mono- or polysubstituted with at least one substituent selected from the group consisting of F, Cl, Br, I, NO$_2$, OH, =O, an O—$C_{1-4}$ aliphatic residue, OCF$_3$, SH, SCF$_3$, a S—$C_{1-4}$ aliphatic residue, CF$_3$, CN, and a $C_{1-4}$-aliphatic residue,
   wherein the $C_{1-4}$-aliphatic residue in each case may be unsubstituted or mono- or polysubstituted with at least one substituent selected from the group consisting of F, Cl, Br, I, OH, CF$_3$ and an unsubstituted O—$C_{1-4}$-aliphatic residue,
and wherein the 3 to 6 membered heterocycloaliphatic residue formed by $R^{609}$ and $R^{610}$ together with the nitrogen atom connecting them may optionally be condensed with phenyl or pyridyl, wherein the phenyl or pyridyl residues condensed in this way can for their part be respectively unsubstituted or mono- or polysubstituted with at least one substituent selected from the group consisting of F, Cl, Br, I, OH, an O—$C_{1-4}$ aliphatic residue, OCF$_3$, SH, SCF$_3$, a S—$C_{1-4}$ aliphatic residue, CF$_3$, CN, a $C_{1-4}$-aliphatic residue, C(=O)—OH, residue, benzyl, phenyl, and pyridyl,
   wherein the $C_{1-4}$-aliphatic residue in each case may be unsubstituted or mono- or polysubstituted with at least one substituent selected from the group consisting of F, Cl, OH, and an unsubstituted O—$C_{1-4}$-aliphatic residue, and
   wherein benzyl, phenyl, and pyridyl, may in each case may be unsubstituted or mono- or polysubstituted with at least one substituent selected from the group consisting of F, Cl, Br, I, OCH$_3$, OCF$_3$, O—CH$_2$—OH, O—CH$_2$—O—CH$_3$, SH, SCF$_3$, CF$_3$, and a $C_{1-4}$-aliphatic residue.
Still more preferably,
$R^{606}$ denotes a $C_{2-6}$-aliphatic residue, preferably selected from the group consisting of ethyl, n-propyl, 2-propyl, n-butyl, isobutyl, sec.-butyl, tert.-butyl, n-pentyl, isopentyl, neopentyl, n-hexyl, ethenyl and propenyl (—$CH_2CH=CH_2$, —$CH=CH—CH_3$, —$C(=CH_2)$—$CH_3$), unsubstituted or mono- or polysubstituted with at least one substituent selected from the group consisting of F, Cl, Br, I, OH, =O, an O—$C_{1-4}$-aliphatic residue, a $C(=O)$—O—$C_{1-4}$-aliphatic residue, $OCF_3$, SH, $SCF_3$, a S—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, more preferably in each case unsubstituted or mono- or polysubstituted with at least one substituent selected from the group consisting of F, Cl, and an O—$C_{1-4}$-aliphatic residue, preferably O-methyl, even more preferably in each case unsubstituted, wherein the $C_{1-4}$-aliphatic residue in each case is unsubstituted, or denotes a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of piperidinyl (preferably piperidin-4-yl or piperidin-3-yl), tetrahydrofuranyl, and tetrahydropyranyl, in each case unsubstituted or mono- or polysubstituted with at least one substituent selected from the group consisting of F, Cl, Br, I, OH, =O, an O—$C_{1-4}$-aliphatic residue, a $C(=O)$—O—$C_{1-4}$-aliphatic residue, $OCF_3$, SH, $SCF_3$, a S—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, more preferably in each case unsubstituted or mono- or polysubstituted with at least one substituent selected from the group consisting of F, Cl, and an O—$C_{1-4}$-aliphatic residue, preferably O-methyl, even more preferably in each case unsubstituted, wherein the $C_{1-4}$-aliphatic residue in each case is unsubstituted, and wherein the $C_{3-6}$-cycloaliphatic residue or the 3 to 6 membered heterocycloaliphatic residue may in each case optionally bridged via an unsubstituted $C_{1-4}$ aliphatic group, preferably via an unsubstituted $C_{1-2}$ aliphatic group, on the condition that if $R^{606}$ a 3 to 6 membered heterocycloaliphatic residue, the 3 to 6 membered heterocycloaliphatic residue is linked via a carbon atom, or $R^{606}$ denotes S—$R^{607}$ or O—$R^{608}$, wherein $R^{607}$ and $R^{608}$ in each case denote a $C_{1-6}$-aliphatic residue, preferably selected from the group consisting of methyl, ethyl, n-propyl, 2-propyl, n-butyl, isobutyl, sec-butyl, tert-butyl, n-pentyl, isopentyl, neopentyl, n-hexyl, ethenyl and propenyl (—$CH_2CH=CH_2$, —$CH=CH—CH_3$, —$C(=CH_2)$—$CH_3$), unsubstituted or mono- or polysubstituted with at least one substituent selected from the group consisting of F, Cl, Br, I, OH, =O, an O—$C_{1-4}$-aliphatic residue, a $C(=O)$—O—$C_{1-4}$-aliphatic residue, $OCF_3$, SH, $SCF_3$, a S—$C_{1-4}$-aliphatic residue, an $NH(C_{1-4}$ aliphatic residue), an $N(C_{1-4}$ aliphatic residue)$_2$, $CF_3$, and a $C_{1-4}$-aliphatic residue, more preferably in each case unsubstituted or mono- or polysubstituted with at least one substituent selected from the group consisting of F, Cl, OH, and an O—$C_{1-4}$-aliphatic residue, wherein the $C_{1-4}$-aliphatic residue in each case is unsubstituted, or denotes a $C_{3-6}$-cycloaliphatic residue, preferably cyclopropyl, or a 3 to 6 membered heterocycloaliphatic residue, preferably oxetanyl, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a $C(=O)$—O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, wherein the $C_{1-4}$-aliphatic residue in each case may be unsubstituted or mono- or polysubstituted with OH or an unsubstituted O—$C_{1-4}$-aliphatic residue, and wherein the $C_{3-10}$-cycloaliphatic residue or the 3 to 10 membered heterocycloaliphatic residue in each case may be bridged, preferably is bridged, via an unsubstituted $C_{1-4}$ aliphatic group, on the condition that if $R^{607}$ or $R^{608}$ denotes a 3 to 10 membered heterocycloaliphatic residue, the 3 to 10 membered heterocycloaliphatic residue is linked via a carbon atom, or $R^{606}$ denotes $N(R^{609}R^{610})$, wherein $R^{609}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a $C(=O)$—O—$C_{1-4}$-aliphatic residue, $OCF_3$, SH, $SCF_3$, a S—$C_{1-4}$-aliphatic residue, $CF_3$, and a $C_{1-4}$-aliphatic residue, preferably an unsubstituted $C_{1-6}$-aliphatic residue, more preferably selected from the group consisting of methyl, ethyl, n-propyl, 2-propyl, n-butyl, isobutyl, sec.-butyl, tert.-butyl, n-pentyl, isopentyl, neopentyl, and n-hexyl, wherein the $C_{1-4}$-aliphatic residue in each case is unsubstituted, or denotes a $C_{3-6}$-cycloaliphatic residue, preferably selected from the group consisting of cyclopropyl, cyclobutyl, cyclopentyl and cyclohexyl, or a 3 to 6 membered heterocycloaliphatic residue, preferably selected from the group consisting of piperidinyl (preferably piperidin-4-yl or piperidin-3-yl), tetrahydrofuranyl, and tetrahydropyranyl, in each case unsubstituted or mono- or polysubstituted with at least one substituent selected from the group consisting of F, Cl, a $C_{1-4}$-aliphatic residue and an O—$C_{1-4}$-aliphatic residue, even more preferably in each case unsubstituted, wherein the $C_{1-4}$-aliphatic residue in each case is unsubstituted, and wherein the $C_{3-6}$-cycloaliphatic residue or the 3 to 6 membered heterocycloaliphatic residue may in each case optionally bridged via an unsubstituted $C_{1-4}$ aliphatic group, on the condition that if $R^{609}$ denotes a 3 to 6 membered heterocycloaliphatic residue, the 3 to 10 membered heterocycloaliphatic residue is linked via a carbon atom, $R^{610}$ denotes H or an unsubstituted $C_{1-4}$-aliphatic residue, preferably represents an unsubstituted $C_{1-4}$-aliphatic residue, or denotes H, methyl, ethyl, n-propyl, 2-propyl, n-butyl, isobutyl, sec-butyl or tert-butyl, preferably denotes methyl, ethyl, n-propyl, 2-propyl, n-butyl, isobutyl, sec-butyl or tert-butyl, or $R^{609}$ and $R^{610}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue wherein the $C_{1-4}$-aliphatic residue in each case may be unsubstituted or mono- or polysubstituted with OH or an unsubstituted O—$C_{1-4}$-aliphatic residue.

Most preferred, $R^{606}$ denotes ethyl, n-propyl, 2-propyl, n-butyl, isobutyl, sec.-butyl, tert.-butyl, n-pentyl, isopentyl, neopentyl, n-hexyl, ethenyl or propenyl (—$CH_2CH$=$CH_2$, —CH=CH—$CH_3$, —C(=$CH_2$)—$CH_3$), in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, preferably O-methyl, more preferably in each case unsubstituted, wherein the $C_{1-4}$-aliphatic residue in each case is unsubstituted, or denotes cyclopropyl, cyclobutyl, cyclopentyl and cyclohexyl, piperidinyl, tetrahydrofuranyl, or tetrahydropyranyl, preferably denotes cyclopropyl or tetrahydropyranyl, more preferably cyclopropyl, in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, preferably O-methyl, more preferably in each case unsubstituted, wherein the $C_{1-4}$-aliphatic residue in each case is unsubstituted, and wherein cyclopropyl, cyclobutyl, cyclopentyl and cyclohexyl, piperidinyl, tetrahydrofuranyl, and tetrahydropyranyl may in each case be optionally bridged via an unsubstituted $C_{1-4}$ aliphatic group, preferably via an unsubstituted $C_{1-2}$ aliphatic group, on the condition that if $R^{606}$ denotes piperidinyl, tetrahydrofuranyl, or tetrahydropyranyl, piperidinyl, tetrahydrofuranyl, or tetrahydropyranyl is linked via a carbon atom, or $R^{606}$ denotes S—$R^{607}$ or O—$R^{608}$, wherein $R^{607}$ and $R^{608}$ in each case denote methyl, ethyl, n-propyl, 2-propyl, n-butyl, isobutyl, sec.-butyl, tert.-butyl, n-pentyl, isopentyl, n-hexyl, ethenyl and propenyl (—$CH_2CH$=$CH_2$, —CH=CH—$CH_3$, —C(=$CH_2$)—$CH_3$), in each case unsubstituted or mono- or polysubstituted with at least one substituent selected from the group consisting of F, Cl, OH, N($C_{1-4}$ aliphatic residue)$_2$ and an O—$C_{1-4}$-aliphatic residue, wherein the $C_{1-4}$-aliphatic residue in each case is unsubstituted, or in each case denote cyclopropyl, cyclobutyl, cyclopentyl cyclohexyl, oxetanyl, piperidinyl, tetrahydrofuranyl, or tetrahydropyranyl, preferably cyclopropyl or oxetanyl, in each case unsubstituted or mono- or polysubstituted with at least one substituent selected from the group consisting of F, Cl, OH, an O—$C_{1-4}$-aliphatic residue, $CF_3$, and a $C_{1-4}$-aliphatic residue, preferably in each case unsubstituted or mono- or polysubstituted with at least one substituent selected from the group consisting of F, Cl, and an O—$C_{1-4}$-aliphatic residue, more preferably in each case unsubstituted, wherein the $C_{1-4}$-aliphatic residue in each case is unsubstituted, and wherein cyclopropyl, cyclobutyl, cyclopentyl and cyclohexyl, oxetanyl, piperidinyl, tetrahydrofuranyl, and tetrahydropyranyl may in each case be optionally bridged via an unsubstituted $C_{1-4}$ aliphatic group, on the condition that if $R^{607}$ or $R^{608}$ denotes piperidinyl, oxetanyl, tetrahydrofuranyl, or tetrahydropyranyl, each of these residues is linked via a carbon atom, or $R^{606}$ denotes N($R^{609}R^{610}$), wherein $R^{609}$ denotes a $C_{1-6}$-aliphatic residue, unsubstituted or mono- or polysubstituted with at least one substituent selected from the group consisting of F, Cl, =O, OH, and O-methyl, preferably unsubstituted or mono- or polysubstituted with at least one substituent selected from the group consisting of F, Cl, and O-methyl, more preferably unsubstituted or mono- or polysubstituted with at least one substituent selected from the group consisting of F and O-methyl, preferably denotes an unsubstituted $C_{1-6}$-aliphatic residue, more preferably selected from the group consisting of methyl, ethyl, n-propyl, 2-propyl, n-butyl, isobutyl, sec.-butyl, tert.-butyl, n-pentyl, isopentyl, neopentyl, and n-hexyl, $R^{610}$ denotes H, methyl, ethyl, n-propyl, 2-propyl, n-butyl, isobutyl, sec-butyl or tert-butyl, preferably methyl, ethyl, n-propyl, 2-propyl, n-butyl, isobutyl, sec-butyl or tert-butyl, more preferably methyl or ethyl, or $R^{609}$ and $R^{610}$ form together with the nitrogen atom connecting them a morpholinyl, piperidinyl, pyrrolidinyl, or azetidinyl, in each case unsubstituted or mono- or polysubstituted with at least one substituent selected from the group consisting of F, Cl, Br, I, OH, an O—$C_{1-4}$ aliphatic residue, and a $C_{1-4}$-aliphatic residue, more preferably unsubstituted or mono- or polysubstituted with at least one substituent selected from the group consisting of F, Cl and a O—$C_{1-4}$ aliphatic residue, preferably form together with the nitrogen atom connecting them a morpholinyl, piperidinyl, pyrrolidinyl, or azetidinyl, in each case unsubstituted.

In particular, $R^{606}$ denotes ethyl, n-propyl, 2-propyl, n-butyl, isobutyl, sec.-butyl, tert.-butyl, n-pentyl, isopentyl, neopentyl, n-hexyl, $CH_2$—CH($CH_3$)($C_2H_5$), C($CH_3$)$_2$($C_2H_5$), ethenyl or propenyl (—$CH_2CH$=$CH_2$, —CH=CH—$CH_3$, —C(=$CH_2$)—$CH_3$), $CH_2$—$OCH_3$, $C_2H_4$—$OCH_3$, $C_3H_6$—$OCH_3$, cyclopropyl, cyclobutyl, or tetrahydropyranyl, in each case unsubstituted, or $R^{606}$, denotes S—$R^{607}$ or O—$R^{608}$, wherein $R^{607}$ and $R^{608}$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, a N($C_{1-4}$ aliphatic residue)$_2$, and an O—$C_{1-4}$-aliphatic residue, preferably with at least one substituent selected from the group consisting of F, OH, N(CH$_3$)$_2$, O-methyl and O-ethyl, or in each case denote CH$_2$-cyclopropyl or oxetanyl, preferably, R$^7$ and R$^8$ in each case denote methyl, ethyl, n-propyl, 2-propyl, n-butyl, isobutyl, sec.-butyl, tert.-butyl, n-pentyl, isopentyl, neopentyl, or n-hexyl, CH$_2$—CH$_2$—F, CH$_2$CHF$_2$, CH2-OCH3, CH$_2$CH$_2$—OCH$_3$, CH$_2$CH$_2$—N(CH$_3$)$_2$, CH$_2$-cyclopropyl or oxetanyl, wherein the C$_{1-4}$-aliphatic residue in each case is unsubstituted, or R$^{606}$ denotes N(R$^{609}$R$^{610}$), wherein R$^{609}$ denotes methyl, ethyl, C(=O)—CH$_3$, n-propyl, 2-propyl, n-butyl, isobutyl, sec.-butyl, tert.-butyl, n-pentyl, isopentyl, neopentyl, or n-hexyl, R$^{610}$ denotes H, methyl or ethyl, preferably methyl or ethyl, or R$^{609}$ and R$^{610}$ form together with the nitrogen atom connecting them a morpholinyl, piperidinyl, pyrrolidinyl, or azetidinyl, in each case unsubstituted.

Particularly preferred is a compound according to general formula (6-I), wherein R$^{601}$ represents the partial structure (6-T1), —(CR$^{612a}$R$^{612b}$)$_{m6}$—R$^{612c}$      (6-T1), wherein m6 is 0, 1 or 2, preferably 0 or 2, more preferably 2, and R$^{612a}$ and R$^{612b}$ each independently of one another represent H, F, OH, CH$_3$ or OCH$_3$ or together denote =O, more preferably H, F, OH or CH$_3$, even more preferably H, R$^{612c}$ denotes a C$_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, CN, OH, S(=O)$_2$—CH$_3$, an unsubstituted O—C$_{1-4}$ aliphatic residue, preferably O-methyl and O-tert.-butyl, and CF$_3$, preferably denotes a C$_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, an unsubstituted O—C$_{1-4}$ aliphatic residue, preferably O-methyl and O-tert.-butyl, and CF$_3$, or denotes a C$_{3-10}$-cycloaliphatic residue or a 3 to 10 membered heterocycloaliphatic residue, preferably cyclopropyl, cyclopentyl, cyclohexyl, morpholinyl, oxetanyl or tetrahydropyranyl, in each case unsubstituted or mono- or polysubstituted with at least one substituent selected from the group consisting of F, Cl, Br, I, an unsubstituted O—C$_{1-4}$ aliphatic residue, preferably O-methyl and O-ethyl, CF$_3$, and an unsubstituted C$_{1-4}$-aliphatic residue, preferably methyl or ethyl, or wherein m6 is 0 or 2, more preferably 0, and R$^{612a}$ and R$^{612b}$ each independently of one another represent H, F, CH$_3$ or OCH$_3$; and R$^{612c}$ denotes an aryl or heteroaryl, preferably phenyl or pyridyl, in each case unsubstituted or mono- or polysubstituted with at least one substituent selected from the group consisting of F, Cl, Br, I, OH, an O—C$_{1-4}$ aliphatic residue. OCF$_3$, OCF$_2$H, CH$_2$—OH, CH$_2$—OCH$_3$, S(=O)$_2$—CH$_3$, SCF$_3$, NO$_2$, N(CH$_3$)$_2$,

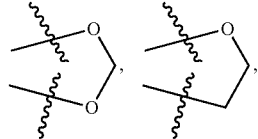 [SMILES: *OCO* ; *CCO*]

CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, preferably denotes an aryl or heteroaryl, preferably phenyl or pyridyl, in each case unsubstituted or mono- or polysubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$, C(=O)—O—C$_2$H$_5$ and phenyl, wherein phenyl may be unsubstituted or mono- or polysubstituted, preferably unsubstituted or mono- or disubstituted with at least one substituent selected from the group consisting of F, Cl, Br, I, OH, an O—C$_{1-4}$ aliphatic residue, OCF$_3$, CF$_3$, CN, a C$_{1-4}$-aliphatic residue, C(=O)—CH$_3$, C(=O)—C$_2$H$_5$, C(=O)—O—CH$_3$ and C(=O)—O—C$_2$H$_5$, preferably with at least one substituent selected from the group consisting of F, Cl, CH$_3$, O—CH$_3$, CF$_3$ and OCF$_3$, R$^{602}$ represents F; Cl; Br; I; CN; CF$_3$; NO$_2$; OCF$_3$; SCF$_3$; methyl; ethyl; n-propyl; iso-propyl; n-butyl; sec.-butyl; tert.-butyl; CH$_2$—OH; CH$_2$—O—CH$_3$; CH$_2$—CH$_2$—OH; CH$_2$—CH$_2$—OCH$_3$; O-methyl; O-ethyl; O—(CH$_2$)$_2$—O—CH$_3$; O—(CH$_2$)$_2$—OH; S-Methyl; S-Ethyl; cyclopropyl, cyclobutyl, cyclopentyl, or cyclohexyl; preferably represents F; Cl; Br; I; CN; CF$_3$; NO$_2$; OCF$_3$; SCF$_3$; methyl; ethyl; n-propyl; iso-propyl; n-butyl; sec.-butyl; tert.-butyl; CH$_2$—OH; O-methyl; O-ethyl; O—(CH$_2$)$_2$—O—CH$_3$; O—(CH$_2$)$_2$—OH; S-Methyl; S-Ethyl; cyclopropyl, cyclobutyl, cyclopentyl, or cyclohexyl, R$^{603}$ represents H; F; Cl; Br; I; CN; CF$_3$; SCF$_3$; NO$_2$; OCF$_3$; methyl; ethyl; n-propyl; iso-propyl; n-butyl; sec.-butyl; tert.-butyl; O-methyl; O-ethyl; O—(CH$_2$)$_2$—O—CH$_3$; O—(CH$_2$)$_2$—OH; S-Methyl; or S-Ethyl, R$^{604}$ represents the partial structure (6-T2), —(CR$^{613a}$R$^{613b}$)$_{n6}$—R$^{613c}$      (6-T2), wherein n6 denotes 0, 1, 2 or 3, preferably denotes 1 or 2, more preferably denotes 1, R$^{613a}$ and R$^{613b}$ each independently of one another represent H, F, CH$_3$ or OCH$_3$, or together denote =O, preferably each independently of one another represent H or CH$_3$, more preferably H, R$^{613c}$ denotes a C$_{1-4}$ aliphatic residue, preferably methyl, ethyl, n-propyl, 2-propyl, n-butyl, isobutyl, sec.-butyl, or tert.-butyl, unsubstituted or mono- or polysubstituted with at least one substituent selected from the group consisting of F, Cl, Br, I, =O, an unsubstituted O—C$_{1-4}$ aliphatic residue, and CF$_3$, or denotes cyclopropyl, cyclobutyl, cyclopentyl or cyclohexyl, pyrrolidinyl, morpholinyl, piperazinyl, piperidinyl and tetrahydropyranyl, more preferably tetrahydropyranyl or morpholinyl, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or denotes an aryl or heteroaryl, preferably phenyl or pyridyl, more preferably phenyl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, and a $C_{1-4}$-aliphatic residue, $R^{605}$ denotes H, methyl or ethyl, $C_2H_4OCH_3$ or $C_3H_6OCH_3$, more preferably H or methyl, even more preferably methyl, or $R^{604}$ and $R^{605}$ form together with the nitrogen atom connecting them a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, preferably a morpholinyl, piperidinyl, pyrrolidinyl, azetidinyl, oxazepanyl, tetrahydroquinolinyl, tetrahydroisoquinolinyl, thiomorpholinyl, azepanyl,

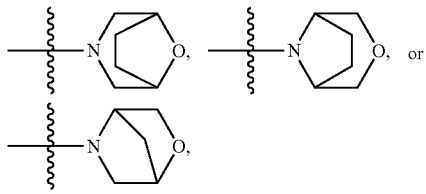

tetrahydroinnidazo[1,2-a]pyrazinyl, octahydropyrrolo[1,2-a]pyrazinyl,

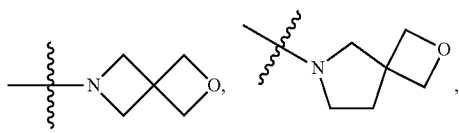 [SMILES: *N1CC2(COC2)C1 ; *N1CCC2(COC2)C1 ; ","]

dihydroindolinyl, or dihydroisoindolyl, preferably a a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, more preferably a morpholinyl, oxazepanyl, tetrahydroquinolinyl, or tetrahydroisoquinolinyl, in each case unsubstituted or mono- or polysubstituted with at least one substituent selected from the group consisting of F, Cl, OH, =O, C(=O)—OH, O-methyl, O-ethyl, $OCF_3$, $SCF_3$, $CF_3$, C(=O)—$CH_3$, C(=O)—$OCH_3$, $CH_2CF_3$, $CH_2OH$, $CH_2$—$OCH_3$, $CH_2CH_2$—$OCH_3$, methyl, ethyl, n-propyl, 2-propyl, cyclopropyl, and cyclobutyl, preferably selected from the group consisting of F, Cl, OH, =O, C(=O)—OH, O-methyl, O-ethyl, $OCF_3$, $SCF_3$, $CF_3$, methyl, ethyl, n-propyl, 2-propyl, cyclopropyl, and cyclobutyl, $R^{606}$ denotes ethyl, n-propyl, 2-propyl, n-butyl, isobutyl, sec.-butyl, tert.-butyl, n-pentyl, isopentyl, neopentyl, n-hexyl, $CH_2$—CH($CH_3$)($C_2H_5$), C($CH_3$)$_2$($C_2H_5$), ethenyl or propenyl (—$CH_2CH$=$CH_2$, —CH=CH—$CH_3$, —C(=$CH_2$)—$CH_3$), $CH_2$—$OCH_3$, $C_2H_4$—$OCH_3$, $C_3H_6$—$OCH_3$, cyclopropyl, cyclobutyl, or tetrahydropyranyl, in each case unsubstituted, or $R^{606}$ denotes S—$R^{607}$ or O—$R^{608}$, wherein $R^{607}$ and $R^{608}$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, a N($C_{1-4}$ aliphatic residue)$_2$, and an O—$C_{1-4}$-aliphatic residue, preferably with at least one substituent selected from the group consisting of F, OH, N($CH_3$)$_2$, O-methyl and O-ethyl, or in each case denote $CH_2$-cyclopropyl or oxetanyl, preferably, $R^7$ and $R^8$ in each case denote methyl, ethyl, n-propyl, 2-propyl, n-butyl, isobutyl, sec.-butyl, tert.-butyl, n-pentyl, isopentyl, neopentyl, or n-hexyl, $CH_2$—$CH_2$—F, $CH_2CHF_2$, CH2-OCH3, $CH_2CH_2$—$OCH_3$, $CH_2CH_2$—N($CH_3$)$_2$, $CH_2$-cyclopropyl or oxetanyl, wherein the $C_{1-4}$-aliphatic residue in each case is unsubstituted, or $R^{606}$ denotes N($R^{609}R^{610}$), wherein $R^{609}$ denotes methyl, C(=O)—$CH_3$, ethyl, n-propyl, 2-propyl, n-butyl, isobutyl, sec.-butyl, tert.-butyl, n-pentyl, isopentyl, neopentyl, or n-hexyl, $R^{610}$ denotes H, methyl or ethyl, preferably methyl or ethyl, or $R^{609}$ and $R^{610}$ form together with the nitrogen atom connecting them a morpholinyl, piperidinyl, pyrrolidinyl, or azetidinyl, in each case unsubstituted.

In another particularly preferred embodiment of the compound according to general formula (6-I), $R^{601}$ represents phenyl or pyridyl, preferably phenyl, in each case unsubstituted or mono- or disubstituted with at least one substituent selected from the group consisting of F, Cl, Br, OH, $OCH_3$, $OCF_3$, $CF_3$, and $CH_3$, $R^{602}$ represents H; $CF_3$; methyl; ethyl; iso-propyl; O-methyl; or cyclopropyl, $R^{603}$ represents H; F; Cl; Br; I; CN; $CF_3$; methyl; or O-methyl, $R^{604}$ and $R^{605}$ form together with the nitrogen atom connecting them a morpholinyl, piperidinyl, pyrrolidinyl, azetidinyl, oxazepanyl, tetrahydroquinolinyl, tetrahydroisoquinolinyl, dihydroindolinyl, or dihydroisoindolyl, in each case unsubstituted, $R^{606}$ denotes ethyl, n-propyl, 2-propyl (iso-propyl), tert.-butyl, cyclopropyl, cyclobutyl or cyclopentyl or tetrahydropyranyl, or $R^{606}$ denotes S—$R^{607}$ or O—$R^{608}$, wherein $R^{607}$ and $R^{608}$ in each case denote methyl, ethyl, 2-propyl, or tert-butyl, or $R^{606}$ denotes N($R^{609}R^{610}$), wherein $R^{609}$ denotes methyl, ethyl, n-propyl, 2-propyl, or tert-butyl, $R^{610}$ denotes H, methyl or ethyl, preferably methyl or ethyl, or $R^{609}$ and $R^{610}$ form together with the nitrogen atom connecting them a morpholinyl, piperidinyl, pyrrolidinyl, or azetidinyl.

Another embodiment of the present invention relates to a compound of general formula (I), wherein the compound is selected from a compound according to general formula (7-I).

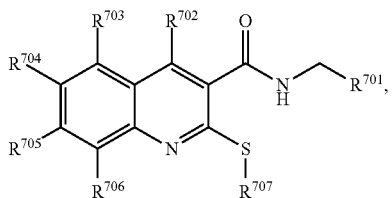

(7-I)

wherein $R^{701}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^{702}$ represents H; F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may be in each case be unsubstituted or mono- or polysubstituted; a $C_{3-8}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{703}$, $R^{704}$, $R^{705}$ and $R^{706}$ each independently of one another represent H; F; Cl; Br; I; CN; $CF_3$; C(=O)H; C(=O)—OH; C(=O)—$NH_2$; $SCF_3$; S(=O)$_2$—OH; $NO_2$; $OCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a S(=O)$_2$—O—$C_{1-4}$-aliphatic residue, wherein the $C_{1-4}$ aliphatic residue may be in each case be unsubstituted or mono- or polysubstituted; a NH($C_{1-4}$ aliphatic residue), a N($C_{1-4}$ aliphatic residue)$_2$, a NH—C(=O)—$C_{1-4}$ aliphatic residue, a NH—S(=O)$_2$—$C_{1-4}$-aliphatic residue, a N($C_{1-4}$ aliphatic residue)-C(=O)—$C_{1-4}$ aliphatic residue, or a N($C_{1-4}$ aliphatic residue)-S(=O)$_2$—$C_{1-4}$ aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{707}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;

on the condition that if $R^{707}$ denotes a 3 to 10 membered heterocycloaliphatic residue, the 3 to 10 membered heterocycloaliphatic residue is linked via a carbon atom, in which an "aliphatic group" and "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an NH($C_{1-4}$ aliphatic residue), an N($C_{1-4}$ aliphatic residue)$_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

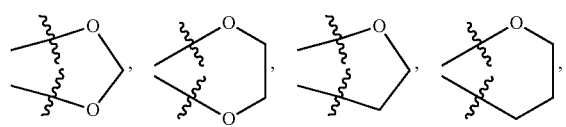 [SMILES: *OCO* ; *OCCO* ; *CCO* ; *CCCO*]

an NH($C_{1-4}$ aliphatic residue), an N($C_{1-4}$ aliphatic residue)$_2$, an NH—C(=O)—$C_{1-4}$ aliphatic residue, an NH—S(=O)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, CF$_3$, C(=O)H, C(=O)OH, a C$_{1-4}$-aliphatic residue, a C(=O)—C$_{1-4}$-aliphatic residue, a C(=O)—O—C$_{1-4}$-aliphatic residue, a C$_{3-6}$-cycloaliphatic residue, a 3 to 6 membered heterocycloaliphatic residue, benzyl, aryl, heteroaryl, C(=O)—NH$_2$, a C(=O)—NH(C$_{1-4}$ aliphatic residue), and a C(=O)—N(C$_{1-4}$ aliphatic residue)$_2$.

The compounds according to general formula (7-I) are known from WO 2010/102811 A1, which is fully included by reference.

Preferred embodiments of the compound according to general formula (7-I) have general formulae (7-Ia), (7-Ib), (7-Ic) or (7-Id):

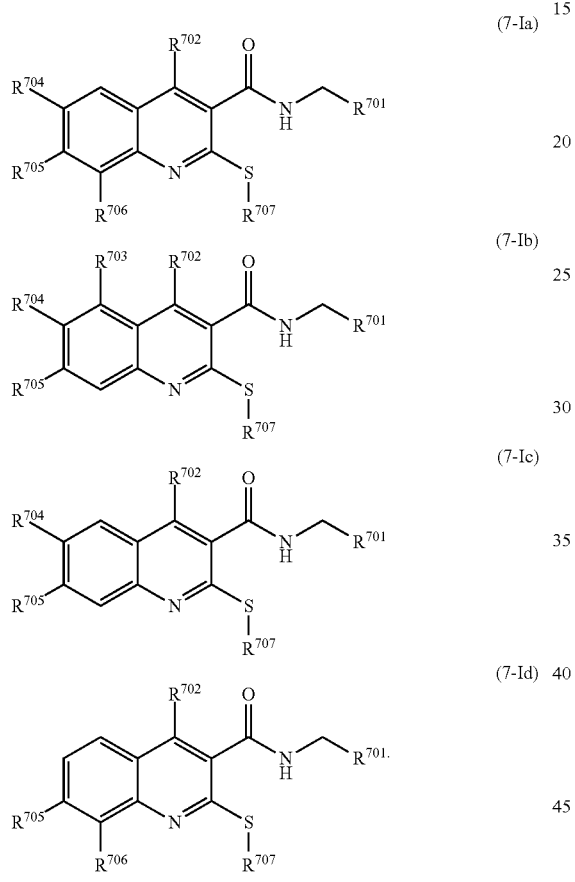

Another preferred embodiment of present invention is a compound according to general formula (7-I), wherein R$^{701}$ denotes a C$_{1-10}$-aliphatic residue, preferably a C$_{1-8}$-aliphatic residue, unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$-aliphatic residue, OCF$_3$, SH, SCF$_3$, a S—C$_{1-4}$-aliphatic residue, CF$_3$, CN, a C$_{1-4}$-aliphatic residue and C(=O)—OH,
 wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue,
 or denotes a C$_{3-10}$-cycloaliphatic residue or a 3 to 10 membered heterocycloaliphatic residue, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, a C$_{3-6}$ cycloaliphatic residue, and a 3 to 6 membered heterocycloaliphatic residue,
 wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
 wherein the C$_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH,
 and wherein the C$_{3-10}$-cycloaliphatic residue or the 3 to 10 membered heterocycloalipatic residue may in each case optionally bridged via a C$_{1-8}$ aliphatic group, preferably a C$_{1-4}$ aliphatic group, which in turn may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, =O, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue and C(=O)—OH,
 or denotes an aryl or heteroaryl, in each case unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, a C$_{3-6}$ cycloaliphatic residue, a 3 to 6 membered heterocycloaliphatic residue,

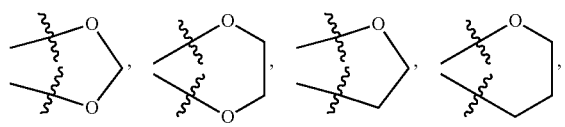 [SMILES: *OCO* ; *OCCO* ; *CCO* ; *CCCO*]

benzyl, phenyl, thienyl, pyridyl, furyl, thiazolyl and oxazolyl,
 wherein the C$_{1-4}$-aliphatic residue in each case may be unsubstituted or mono- or polysubstituted with at least one substituent selected from the group consisting of F, Cl, Br, I, OH, OCF$_3$, CF$_3$ and an unsubstituted O—C$_{1-4}$-aliphatic residue, and
 wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, NO$_2$, NH$_2$, an NH(C$_{1-4}$ aliphatic residue), an N(C$_{1-4}$ aliphatic residue)$_2$, OH, an O—C$_{1-4}$ aliphatic residue, OCF$_3$, O—CH$_2$—OH, O—CH$_2$—O—CH$_3$, SH, SCF$_3$, a S—C$_{1-4}$ aliphatic residue, CF$_3$, CN, a C$_{1-4}$-aliphatic residue, C(=O)—OH, C(=O)—CH$_3$, C(=O)—C$_2$H$_5$, C(=O)—O—CH$_3$ and C(=O)—O—C$_2$H$_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and C(=O)—OH, $R^{702}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted, preferably represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and an O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, $R^{703}$, $R^{704}$, $R^{705}$ and $R^{706}$ each independently of one another represent H; F; Cl; Br; I; CN; $CF_3$; $OCF_3$; $SCF_3$; C(=O)H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{703}$, $R^{704}$, $R^{705}$ and $R^{706}$ is ≠H, $R^{707}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, on the condition that if $R^{707}$ denotes a 3 to 10 membered heterocycloaliphatic residue, the 3 to 10 membered heterocycloaliphatic residue is linked via a carbon atom.

In a preferred embodiment of the compound according to general formula (2-I), the residue $R^{701}$ denotes a $C_{1-10}$-aliphatic residue, preferably a $C_{1-5}$-aliphatic residue, unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue and C(=O)—OH,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes an aryl or heteroaryl, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

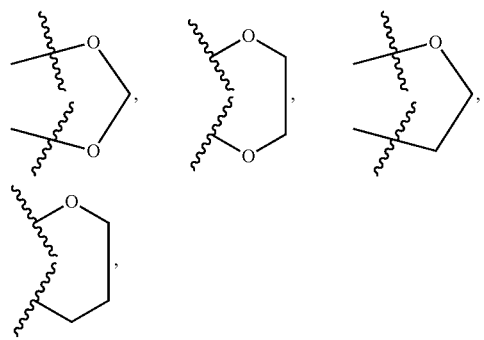

benzyl, phenyl, thienyl, pyridyl, furyl, thiazolyl and oxazolyl,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, an O—$C_{1-4}$ aliphatic residue, $OCF_3$, O—$CH_2$—OH, O—$CH_2$—O—$CH_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
and wherein the aryl or the heteroaryl residue may in each case be optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN and C(=O)—OH.

In a further preferred embodiment of the compound according to general formula (7-I), the residue $R^{701}$ represents the partial structure (7-T1)

$$—(CR^{708a}R^{708b})_{m7}—R^{708c} \qquad (7\text{-}T1),$$

wherein
m7 denotes 0, 1, 2, 3 or 4, preferably denotes 0, 1, or 2,
$R^{708a}$ and $R^{708b}$ each independently of one another represent H, F, Cl, Br, I, $NO_2$, $NH_2$, a NH($C_{1-4}$ aliphatic residue), an N($C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$ aliphatic residue or C(=O)—OH, or together denote =O,
preferably each independently of one another represent H, F, Cl, Br, I, $NH_2$, a NH($C_{1-4}$ aliphatic residue), a N($C_{1-4}$ aliphatic residue)$_2$, OH, O—$C_{1-4}$ aliphatic residue or a $C_{1-4}$ aliphatic residue,
more preferably each independently of one another represent H, F, Cl, Br, I, an O—$C_{1-4}$ aliphatic residue or a $C_{1-4}$ aliphatic residue,
even more preferably each independently of one another represent H, F, an O—$C_{1-4}$ aliphatic residue or a $C_{1-4}$ aliphatic residue, and
$R^{708c}$ denotes a $C_{1-4}$ aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
or denotes a $C_{3-10}$-cycloaliphatic residue or a 3 to 10 membered heterocycloaliphatic residue, preferably when m2 is ≠0, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a $C_{3-6}$ cycloaliphatic residue and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH, or denotes—preferably when m2 is =0—an aryl or heteroaryl, in each case unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue,

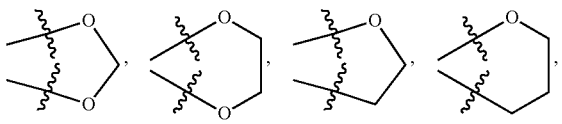 [SMILES: *OCO* ; *OCCO* ; *CCO* ; *CCCO*]

benzyl, phenyl, thienyl, pyridyl, furyl, thiazolyl and oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an $NH(C_{1-4}$ aliphatic residue), an $N(C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH.

Preferably, $R^{701}$ represents the partial structure (7-T1), wherein m7 denotes 0, 1, or 2, $R^{708a}$ and $R^{708b}$ each independently of one another represent H, F, Cl, Br, I, an O—$C_{1-4}$ aliphatic residue or a $C_{1-4}$ aliphatic residue, preferably each independently of one another represent H, F, a O—$C_{1-2}$ aliphatic residue or a $C_{1-2}$ aliphatic residue, and $R^{708c}$ denotes a $C_{1-4}$ aliphatic residue, unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue, C(=O)—OH, a $C_{3-6}$ cycloaliphatic residue, and a 3 to 6 membered heterocycloaliphatic residue, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH, or denotes—preferably when m7 is =0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl, pyridyl, furyl, thiazolyl or oxazolyl, wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein benzyl, phenyl, thienyl, pyridyl, furyl, thiazolyl and oxazolyl may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—OH, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH.

More preferably, $R^{701}$ represents the partial structure (7-T1), wherein m7 denotes 0, 1, or 2, $R^{708a}$ and $R^{708b}$ each independently of one another represent H, F, Cl, Br, I, an O—$C_{1-4}$ aliphatic residue or a $C_{1-4}$ aliphatic residue, preferably each independently of one another represent H, F, a O—$C_{1-2}$ aliphatic residue or a $C_{1-2}$ aliphatic residue, and $R^{708c}$ denotes a $C_{1-4}$ aliphatic residue, unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an O—$C_{1-4}$ aliphatic residue, $CF_3$, and a $C_{1-4}$-aliphatic residue, wherein the $C_{1-4}$-aliphatic residue in each case may be unsubstituted or mono- or polysubstituted with at least one substituent selected from the group consisting of F, Cl, $CF_3$ and an unsubstituted O—$C_{1-4}$-aliphatic residue, or denotes—preferably when m7 is =0—an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, a $C_{3-6}$ cycloaliphatic residue, a 3 to 6 membered heterocycloaliphatic residue, benzyl, phenyl, thienyl or pyridyl, wherein benzyl, phenyl, thienyl and pyridyl, may in each case may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, and wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, OH, =O, an O—$C_{1-4}$ aliphatic residue, $OCF_3$, $CF_3$, a $C_{1-4}$-aliphatic residue and C(=O)—OH.

In a further preferred embodiment of the compound according to general formula (7-I), the residue $R^{701}$ represents the partial structure (7-T1), wherein m7 is 0, 1 or 2 and $R^{708a}$ and $R^{708b}$ each independently of one another represent H, F, a O—$C_{1-4}$ aliphatic residue or a $C_{1-4}$ aliphatic residue; preferably H, F, $CH_3$ or $OCH_3$;

$R^{708c}$ denotes a $C_{1-4}$ aliphatic residue, unsubstituted or mono- or polysubstituted with at least one substituent selected from the group consisting of F, Cl, Br, I, an unsubstituted aliphatic residue, $CF_3$, and an unsubstituted $C_{1-4}$-aliphatic residue, or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted aliphatic residue, $CF_3$, and an unsubstituted $C_{1-4}$-aliphatic residue, or wherein m7 is 0, $R^{708a}$ and $R^{708b}$ each independently of one another represent H, F, a O—$C_{1-4}$ aliphatic residue or a $C_{1-4}$ aliphatic residue; preferably H, F, $CH_3$ or $OCH_3$; and $R^{708c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl, wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$.

Particularly preferred is a compound according to general formula (7-I) which has the following general formula (7-Ie):

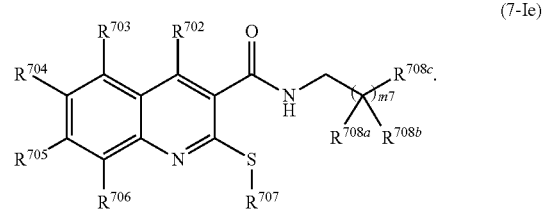

(7-Ie)

In a preferred embodiment of the compound according to general formula (7-I), the residue $R^{702}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted.

Preferably, $R^{702}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, and wherein the $C_{3-6}$-cycloaliphatic residue or the 3 to 6 membered heterocycloaliphatic residue may in each case be optionally bridged via a $C_{1-4}$ aliphatic group, which in turn may be unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue.

More preferably, $R^{702}$ represents H; F; Cl; Br; I; CN; $CF_3$; $NO_2$; $OCF_3$; $SCF_3$; a $C_{1-4}$-aliphatic residue, a S—$C_{1-4}$-aliphatic residue, a O—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and an unsubstituted O—$C_{1-4}$-aliphatic residue, cyclopropyl, cyclobutyl, cyclopentyl, cyclohexyl, pyrrolidinyl, piperazinyl, 4-methylpiperazinyl, morpholinyl, or piperidinyl, preferably cyclopropyl, cyclobutyl, cyclopentyl or cyclohexyl, in each case unsubstituted or mono- or polysubstituted with at least one substituent selected from the group consisting of F, Cl, Br, I, =O, OH, an unsubstituted $C_{1-4}$-aliphatic residue and an unsubstituted O—$C_{1-4}$-aliphatic residue, and wherein cyclopropyl, cyclobutyl, cyclopentyl, cyclohexyl, pyrrolidinyl, piperazinyl, 4-methylpiperazinyl, morpholinyl or piperidinyl may in each case be optionally bridged via an $C_{1-4}$ aliphatic group, which in turn may be unsubstituted or mono- or polysubstituted with at least one substituent selected from the group consisting of F, Cl, OH, an unsubstituted $C_{1-4}$-aliphatic residue and an unsubstituted O—$C_{1-4}$-aliphatic residue.

Even more preferably, $R^{702}$ represents H; F; Cl; Br; I; CN; $CF_3$; $NO_2$; $OCF_3$; $SCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, and cyclohexyl.

Still more preferably, $R^{702}$ is selected from the group consisting of H; F; Cl; $CF_3$; CN; $SCF_3$; $OCF_3$; $CH_3$; $C_2H_5$; n-propyl; iso-propyl; t-butyl; cyclopropyl; O—$CH_3$ and O—$C_2H_5$;

In particular, $R^{702}$ is selected from the group consisting of H; F; Cl; $CF_3$; $CH_3$; $C_2H_5$, iso-propyl; cyclopropyl; and O—$CH_3$;

In a particular preferred embodiment of the compound according to general formula (7-I), the residue $R^{702}$ is ≠H.

In a preferred embodiment of the compound according to general formula (7-I), the residues $R^{703}$, $R^{704}$, $R^{705}$ and $R^{706}$ each independently of one another represent H; F; Cl; Br; I; CN; $CF_3$; $OCF_3$; $SCF_3$; C(=O) H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, a NH($C_{1-4}$ aliphatic residue), a N($C_{1-4}$ aliphatic residue)$_2$, a NH—C(=O)—$C_{1-4}$ aliphatic residue, and a NH—S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{703}$, $R^{704}$, $R^{705}$ and $R^{706}$ is ≠H.

Preferably, $R^{703}$, $R^{704}$, $R^{705}$ and $R^{706}$ each independently of one another represent H; F; Cl; Br; I; CN; $CF_3$; $OCF_3$; $SCF_3$; C(=O) H; C(=O)—OH; C(=O)—$NH_2$; S(=O)$_2$—OH; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a O—C(=O)—$C_{1-4}$-aliphatic residue, a S—$C_{1-4}$-aliphatic residue, a S(=O)$_2$—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue or a 3 to 6 membered heterocycloaliphatic residue, in each case unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{703}$, $R^{704}$, $R^{705}$ and $R^{706}$ is ≠H.

More preferably, $R^{703}$, $R^{704}$, $R^{705}$ and $R^{706}$ each independently of one another represent H; F; Cl; Br; I; CN; $CF_3$; $OCF_3$; $SCF_3$; C(=O) H; $NO_2$; a $C_{1-4}$-aliphatic residue, a C(=O)—$C_{1-4}$ aliphatic residue, a C(=O)—O—$C_{1-4}$ aliphatic residue, a O—$C_{1-4}$-aliphatic residue, a S—$C_{1-4}$-aliphatic residue, wherein the $C_{1-4}$-aliphatic residue in each case may be unsubstituted or mono- or polysubstituted with at least one substituent selected from the group consisting of F, Cl, Br, I, =O, OH, and a O—$C_{1-4}$-aliphatic residue; a $C_{3-6}$-cycloaliphatic residue, unsubstituted or mono- or polysubstituted with at least one substituent selected from the group consisting of F, Cl, Br, I, =O, OH, a $C_{1-4}$-aliphatic residue and a O—$C_{1-4}$-aliphatic residue, and in each case optionally bridged via an unsubstituted $C_{1-4}$ aliphatic group, preferably on the condition that at least one of $R^{703}$, $R^{704}$, $R^{705}$ and $R^{706}$ is ≠H.

In a further preferred embodiment of the present invention, $R^{703}$, $R^{704}$, $R^{705}$ and $R^{706}$ each independently of one another are selected from the group consisting of H; F; Cl; Br; I; $NO_2$; $CF_3$; CN; $OCF_3$; $SCF_3$; a (C=O)—$C_{1-4}$ aliphatic residue, a $C_{1-4}$ aliphatic residue, O—$C_{1-4}$ aliphatic residue, a S—$C_{1-4}$ aliphatic residue, wherein the $C_{1-4}$-aliphatic residue in each case may be unsubstituted or mono- or polysubstituted with at least one substituent selected from the group consisting of F, Cl, and O—$CH_3$;
preferably on the condition that at least one of $R^{703}$, $R^{704}$, $R^{705}$ and $R^{706}$ is ≠H.

Preferably,
$R^{703}$, $R^{704}$, $R^{705}$ and $R^{706}$ each independently of one another are selected from the group consisting of H; F; Cl; Br; I; $NO_2$; $CF_3$; CN; $OCF_3$; $SCF_3$; methyl; ethyl; n-propyl; iso-propyl; n-butyl; sec.-butyl; tert.-butyl; cyclopropyl; C(=O)-methyl; C(=O)-ethyl; (C=O)-isopropyl; (C=O)-t-butyl; O-methyl; O-ethyl; O-isopropyl; O-t-butyl; O—$(CH_2)_2$—O—$CH_3$; S-Methyl; S-Ethyl;
preferably on the condition that at least one of $R^{703}$, $R^{704}$, $R^{705}$ and $R^{706}$ is ≠H.

In particular,
$R^{703}$, $R^{704}$, $R^{705}$ and $R^{706}$ are each independently of one another are selected from the group consisting of H; F; Cl; Br; I; $NO_2$; $CF_3$; CN; (C=O)-methyl; (C=O)-ethyl; (C=O)-isopropyl; (C=O)-t-butyl; methyl; ethyl; isopropyl; t-butyl; O-methyl; O-Ethyl; O-isopropyl; O-t-butyl; $OCF_3$; S-methyl; S-ethyl; and $SCF_3$;
preferably on the condition that at least one of $R^{703}$, $R^{704}$, $R^{705}$ and $R^{706}$ is ≠H.

More particularly,
$R^{703}$, $R^{704}$, $R^{705}$ and $R^{706}$ are each independently of one another selected from the group consisting of H; F; Cl; Br; $CF_3$; CN; $OCF_3$ and $NO_2$;
preferably on the condition that at least one of $R^{703}$, $R^{704}$, $R^{705}$ and $R^{706}$ is ≠H.

Most preferred,
$R^{703}$, $R^{704}$ and $R^{706}$ each independently of one another are selected from the group consisting of H and F; and
$R^{705}$ denotes F; Br; $CF_3$; $OCF_3$; CN; or $NO_2$;

In a particular preferred embodiment of the compound according to general formula (7-I) at least one of the residues $R^{703}$, $R^{704}$, $R^{705}$ and $R^{706}$ is ≠H.

In a preferred embodiment of the compound according to general formula (7-I), the residue
$R^{707}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$-aliphatic residue, $OCF_3$, SH, $SCF_3$, a S—$C_{1-4}$-aliphatic residue, $CF_3$, CN, a $C_{1-4}$-aliphatic residue, a C(=O)—O—$C_{1-4}$-aliphatic residue, and C(=O)—OH,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue, C(=O)—OH, a C(=O)—O—$C_{1-4}$-aliphatic residue a $C_{3-6}$ cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, $OCF_3$, SH, $SCF_3$, a S—$C_{1-4}$ aliphatic residue, $CF_3$, CN, a $C_{1-4}$-aliphatic residue and C(=O)—OH,
and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, $NH_2$, an NH($C_{1-4}$ aliphatic residue), an N($C_{1-4}$ aliphatic residue)$_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, a $C_{1-4}$-aliphatic residue and C(=O)—OH,
on the condition that if $R^{207}$ denotes a 3 to 10 membered heterocycloaliphatic residue, the 3 to 10 membered heterocycloaliphatic residue is linked via a carbon atom.

In a further preferred embodiment of the compound according to general formula (7-I), the residue
$R^{707}$ denotes a $C_{1-10}$-aliphatic residue, preferably a $C_{1-8}$-aliphatic residue, unsubstituted or mono- or polysubstituted with at least one substituent selected from the group consisting of F, Cl, Br, I, $NO_2$, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, CN, and a $C_{1-4}$-aliphatic residue
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, a $C_{1-4}$-aliphatic residue, a $C_{3-6}$ cycloaliphatic residue, and a 3 to 6 membered heterocycloaliphatic residue,
wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-6}$ cycloaliphatic residue and the 3 to 6 membered heterocycloaliphatic residue may in each case may be unsubstituted or mono- or polysubstituted with at least one substituent selected from the group consisting of F, Cl, Br, I, $NO_2$, OH, =O, an O—$C_{1-4}$ aliphatic residue, $OCF_3$, SH, $SCF_3$, a S—$C_{1-4}$ aliphatic residue, $CF_3$, CN, and a $C_{1-4}$-aliphatic residue,
and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, $NO_2$, OH, =O, an O—$C_{1-4}$ aliphatic residue, a C(=O)—O—$C_{1-4}$-aliphatic residue, $OCF_3$, SH, $SCF_3$, a S—$C_{1-4}$ aliphatic residue, $CF_3$, CN, and a $C_{1-4}$-aliphatic residue.
on the condition that if $R^{707}$ denotes a 3 to 10 membered heterocycloaliphatic residue, the 3 to 10 membered heterocycloaliphatic residue is linked via a carbon atom.
Preferably,
$R^{707}$ denotes a $C_{1-8}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue
 wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a C(=O)—O—$C_{1-4}$-aliphatic residue, a S—$C_{1-4}$ aliphatic residue, $CF_3$, and a $C_{1-4}$-aliphatic residue,
 wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
and wherein the $C_{3-10}$-cycloaliphatic residue or the 3 to 10 membered heterocycloaliphatic residue may in each case optionally bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue.
on the condition that if $R^{707}$ denotes a 3 to 10 membered heterocycloaliphatic residue, the 3 to 10 membered heterocycloaliphatic residue is linked via a carbon atom.
More preferably,
$R^{707}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, $CF_3$, a C(=O)—O—$C_{1-4}$-aliphatic residue, and a $C_{1-4}$-aliphatic residue
 wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue,
 wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and wherein the $C_{3-10}$-cycloaliphatic residue or the 3 to 10 membered heterocycloaliphatic residue is bridged via a $C_{1-8}$ aliphatic group, preferably a $C_{1-4}$ aliphatic group, which in turn may be unsubstituted or mono- or polysubstituted with at least one substituent selected from the group consisting of F, Cl, Br, I, OH, =O, an O—$C_{1-4}$ aliphatic residue, $OCF_3$, SH, $SCF_3$, a S—$C_{1-4}$ aliphatic residue, a C(=O)—O—$C_{1-4}$-aliphatic residue, $CF_3$, CN, and a $C_{1-4}$-aliphatic residue.
Even more preferably,
$R^{707}$ denotes a $C_{1-8}$-aliphatic residue, preferably a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, $OCF_3$, SH, $SCF_3$, a S—$C_{1-4}$-aliphatic residue, a C(=O)—O—$C_{1-4}$-aliphatic residue, $CF_3$, and a $C_{1-4}$-aliphatic residue
 wherein the $C_{1-4}$-aliphatic residue in each case may be unsubstituted or mono- or polysubstituted with at least one substituent selected from the group consisting of F, Cl, Br, I, OH, $CF_3$ and an unsubstituted O—$C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue,
 wherein the $C_{1-4}$-aliphatic residue in each case may be unsubstituted or mono- or polysubstituted with at least one substituent selected from the group consisting of F, Cl, Br, I, OH, $OCF_3$, $CF_3$ and an unsubstituted O—$C_{1-4}$-aliphatic residue, and
wherein the $C_{3-10}$-cycloaliphatic residue or the 3 to 10 membered heterocycloaliphatic residue is in each case bridged via a unsubstituted $C_{1-8}$ aliphatic group, preferably an unsubstituted $C_{1-4}$ aliphatic group.
Still more preferably,
$R^{707}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue
 wherein the $C_{1-4}$-aliphatic residue in each case is unsubstituted,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, OH, =O, an O—$C_{1-4}$ aliphatic residue, $OCF_3$, $SCF_3$, a S—$C_{1-4}$ aliphatic residue, a C(=O)—O—$C_{1-4}$-aliphatic residue, $CF_3$, and a $C_{1-4}$-aliphatic residue,
 wherein the $C_{1-4}$-aliphatic residue in each case may be unsubstituted or mono- or polysubstituted with OH or an unsubstituted O—$C_{1-4}$-aliphatic residue.
and wherein the $C_{3-10}$-cycloaliphatic residue or the 3 to 10 membered heterocycloaliphatic residue is in each case bridged via a unsubstituted $C_{1-4}$ aliphatic group
In particular,
$R^{707}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue wherein the $C_{1-4}$-aliphatic residue in each case is unsubstituted.

Most preferred,
$R^{707}$ denotes a $C_{1-6}$-aliphatic residue, unsubstituted or mono- or polysubstituted with at least one substituent selected from the group consisting of F, $CF_3$, Cl, OH, and O-methyl.

Preferred is also a compound according to general formula (7-I), wherein
$R^{701}$ represents the partial structure (7-T1),

(7-T1), wherein
m7 is 0, 1 or 2 and
$R^{708a}$ and $R^{708b}$ each independently of one another represent H, F, a O—$C_{1-4}$ aliphatic residue or a $C_{1-4}$ aliphatic residue; preferably H, F, $CH_3$ or $OCH_3$;
$R^{708c}$ denotes a $C_{1-4}$ aliphatic residue, unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue,
or
wherein
m7 is 0,
$R^{708a}$ and $R^{708b}$ each independently of one another represent H, F, a O—$C_{1-4}$ aliphatic residue or a $C_{1-4}$ aliphatic residue; preferably H, F, $CH_3$ or $OCH_3$; and
$R^{708c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted, preferably unsubstituted or mono- or disubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, preferably with at least one substituent selected from the group consisting of F, Cl, $CH_3$, O—$CH_3$, $CF_3$ and $OCF_3$, $R^{702}$ is selected from the group consisting of H; F; Cl; $CF_3$; $CH_3$; $C_2H_5$, iso-propyl; cyclopropyl; and O—$CH_3$;
$R^{703}$, $R^{704}$, $R^{705}$ and $R^{706}$ are each independently of one another selected from the group consisting of H; F; Cl; Br; $CF_3$; CN; $OCF_3$ and $NO_2$;
preferably on the condition that at least one of $R^{203}$, $R^{204}$, $R^{205}$ and $R^{206}$ is ≠H,
$R^{707}$ denotes a $C_{1-6}$-aliphatic residue, unsubstituted or mono- or polysubstituted with at least one substituent selected from the group consisting of F, Cl, Br, I, OH, =O, an O—$C_{1-4}$-aliphatic residue, a C(=O)—O—$C_{1-4}$-aliphatic residue, $OCF_3$, SH, $SCF_3$, a S—$C_{1-4}$-aliphatic residue, $CF_3$, and a $C_{1-4}$-aliphatic residue
wherein the $C_{1-4}$-aliphatic residue in each case is unsubstituted.

Particularly preferred is also a compound according to general formula (7-I), wherein $R^{701}$ represents aryl, preferably phenyl, or heteroaryl, preferably pyridyl or thienyl, in each case unsubstituted or mono- or disubstituted with at least one substituent selected from the group consisting of F, Cl, Br, I, OH, $OCH_3$, $OCF_3$, $CF_3$, CN, and $CH_3$,
preferably represents phenyl, unsubstituted or mono- or disubstituted with at least one substituent selected from the group consisting of F, Cl, Br, I, OH, $OCH_3$, $OCF_3$, $CF_3$, CN, and $CH_3$;
$R^{702}$ is selected from the group consisting of H, F, Cl, $CF_3$, $CH_3$, $C_2H_5$, iso-propyl, cyclopropyl, and O—$CH_3$; preferably is selected from the group consisting of $CH_3$, $C_2H_5$, $OCH_3$ and $CF_3$;
$R^{703}$, $R^{704}$, $R^{705}$ and $R^{706}$ are each independently of one another selected from the group consisting of H, F, Cl, Br, $CF_3$, CN, $OCF_3$ and $NO_2$;
preferably on the condition that at least one of $R^{703}$, $R^{704}$, $R^{705}$ and $R^{706}$ is, ≠H, more preferably on the condition that $R^{705}$ is ≠H;
$R^{707}$ denotes a saturated $C_{1-4}$-aliphatic residue, unsubstituted or mono- or disubstituted with at least one substituent selected from the group consisting of F, Cl, Br, I, OH, O—$CH_3$, $OCF_3$, $SCF_3$, and $CF_3$.

Another aspect of the present invention further relates to at least one compound according to general formula (I) and also if appropriate of one or more pharmaceutically acceptable auxiliaries for the use in the preparation of a medicament for prophylaxis and/or treatment of disorders and/or diseases which are mediated, at least in part, by TSPO activity.

The selection of the physiologically acceptable auxiliaries and also the amounts thereof to be used depend on whether the pharmaceutical composition is to be applied orally, subcutaneously, parenterally, intravenously, intraperitoneally, intradermally, intramuscularly, intranasally, buccally, rectally or locally, for example to infections of the skin, the mucous membranes and of the eyes. Preparations in the form of tablets, dragées, capsules, granules, pellets, drops, juices and syrups are preferably suitable for oral application; solutions, suspensions, easily reconstitutable dry preparations and also sprays are preferably suitable for parenteral, topical and inhalative application. The substituted compounds according to the invention used in the pharmaceutical composition according to the invention in a repository, in a dissolved form or in a plaster, and further agents promoting skin penetration being added if appropriate, are suitable percutaneous application preparations. Orally or percutaneously applicable preparation forms can release the respective substituted compound according to the invention also in a delayed manner.

The pharmaceutical compositions according to the invention can be prepared with the aid of conventional means, devices, methods and process known in the art, such as are described for example in "Remington's Pharmaceutical Sciences", A. R. Gennaro (Editor), 17$^{th}$ edition, Mack Publishing Company, Easton, Pa., 1985, in particular in Part 8, Chapters 76 to 93. The corresponding description is introduced herewith by way of reference and forms part of the disclosure. The amount to be administered to the patient of the respective substituted compounds according to the invention of the above-indicated general formula (I) may vary and is for example dependent on the patient's weight or age and also on the type of application, the indication and the severity of the disorder. Conventionally, 0.001 to 100 mg/kg, preferably 0.05 to 75 mg/kg, particularly preferably 0.05 to 50 mg of at least one compound according to the invention are applied per kg of the patient's body weight.

Preference is given to at least one compound according to general formula (I) and optionally one or more pharmaceutically acceptable auxiliaries for the use in the preparation of a medicament for the prophylaxis and/or treatment of disorders and/or diseases selected from the group consisting of
(i) neurological and neurodegenerative disorders, including
ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia;
(ii) psychiatric disorders, including
anxiety disorders, particularily panic disorders, post traumatic stress disorder, panic and adult separation disorder, social anxiety, major depression with adult separation anxiety disorder and bipolar disorder with adult separation anxiety disorder, dysthymia, angina pectoris, suicidality and schizophrenia;
(iii) brain tumours;
(iv) immunological disorders and inflammatory diseases, including
neuroinflammation and arthritis, encephalomyelitis and irritable bowel syndrome.

Particular preference is given to at least one compound according to general formula (I) and optionally one or more pharmaceutically acceptable auxiliaries for use in the preparation of a medicament for the prophylaxis and/or treatment of neurological and neurodegenerative disorders, including Ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia.

Particular preference is given to at least one compound according to general formula (I) and optionally one or more pharmaceutically acceptable auxiliaries for use in the preparation of a medicament for the prophylaxis and/or treatment of psychiatric disorders, including anxiety disorders, particularily panic disorders, post traumatic stress disorder, panic and adult separation disorder, social anxiety, major depression with adult separation anxiety disorder and bipolar disorder with adult separation anxiety disorder, dysthymia, angina pectoris, suicidality and schizophrenia.

Particular preference is given to at least one compound according to general formula (I) and optionally one or more pharmaceutically acceptable auxiliaries for use in the preparation of a medicament for the prophylaxis and/or treatment of brain tumours.

Particular preference is given to at least one compound according to general formula (I) and optionally one or more pharmaceutically acceptable auxiliaries for use in the preparation of a medicament for the prophylaxis and/or treatment of immunological disorders and inflammatory diseases, including neuroinflammation and arthritis, encephalomyelitis and irritable bowel syndrome.

Another aspect of the present invention is a method of treatment and/or prophylaxis of disorders and/or diseases, which are mediated, at least in part, by TSPO activity, in a mammal, preferably of disorders and/or diseases selected from the group consisting of (i) neurological and neurodegenerative disorders, including
ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia;
(ii) psychiatric disorders, including
anxiety disorders, particularily panic disorders, post traumatic stress disorder, panic and adult separation disorder, social anxiety, major depression with adult separation anxiety disorder and bipolar disorder with adult separation anxiety disorder, dysthymia, angina pectoris, suicidality and schizophrenia;
(iii) brain tumours;
(iv) immunological disorders and inflammatory diseases, including
neuroinflammation and arthritis, encephalomyelitis and irritable bowel syndrome, which comprises administering an effective amount of at least one compound of general formula (I) to the mammal.

The various, and in particular the preferred, embodiments of the first aspect of the present invention apply in analogous manner—mutatis mutandis—to the other aspects of the present invention.

PHARMACOLOGICAL EXPERIMENTS

Evaluation of the in vitro affinity of test substances for the rat peripheral BZD receptor was performed according to Le Fur et al. (1983). Life Sci., 33: 449-457. For this purpose, rat heart membranes and [3H]PK 11195 (1-(2-chlorophenyl)-N-methyl-N-(1-methylpropyl)-3-isoquinolinecarboxamide) were used in a radioligand binding test system.

In detail, membrane homogenates of heart (20 µg protein) are incubated for 15 min at 22° C. with 0.2 nM [3H]PK 11195 in the absence or presence of the test compound in a buffer containing 50 mM Tris-HCl (pH 7.4) and 10 mM $MgCl_2$ (96-well plate format). Compound addition is 100× solution in solvent. Nonspecific binding is determined in the presence of 10 µM PK 11195. Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried, then counted for radioactivity in a scintillation counter (Topcount, Packard) using a scintillation cocktail (Microscint 0, Packard). The results are expressed as a percent inhibition of the control radioligand specific binding.

The standard reference compound is PK 11195, which is tested in each experiment concurrently with the test compounds.

For analysis, the specific ligand binding to the receptors is defined as the difference between the total binding and the nonspecific binding determined in the presence of an excess of unlabelled ligand. The results are expressed as a percent of control specific binding ((measured specific binding/control specific binding)×100) obtained in the presence of the test compounds. The data are summarized in table 1.

TABLE 1

| # | Test Compound | Source of test compound | %-Inhibition @ 10 μM |
|---|---|---|---|
| 1 | N-[(3-Fluorophenyl)-methyl]-2-isopropyl-4-methyl-7-(trifluoromethyl)-quinoline-3-carboxylic acid amide | Example 8 in WO2012/025238 A1 | 87 |
| 2 | N-(4,4-Dimethyl-pentyl)-2-ethylsulfanyl-4-methyl-6-morpholin-4-yl-pyridine-3-carboxylic acid amide | Example 67 in WO2012/052167 A1 | 43 |
| 3 | N-[(4-Chlorophenyl)-methyl]-2-ethylsulfanyl-4-methyl-6-morpholin-4-yl-pyridine-3-carboxylic acid amide | Example 124 in WO2012/052167 A1 | 91 |
| 4 | N-[(4-Chlorophenyl)-methyl]-2-methoxy-4-methyl-6-morpholin-4-yl-pyridine-3-carboxylic acid amide | Example 165 in WO2012/052167 A1 | 49 |
| 5 | 2-[[3,3-Difluoro-3-(4-fluorophenyl)-propyl]sulfanyl]-N-[(4-fluorophenyl)-methyl]-pyridine-3-carboxylic acid amide | Example 124 in WO2010/102809 A1 | 102 |
| 6 | N-(5-Bicyclo[2.2.1]heptanyl-methyl)-2-[[3,3-difluoro-3-(4-fluorophenyl)-propyl]sulfanyl]-pyridine-3-carboxylic acid amide | Example 115 in WO2010/102809 A1 | 99 |
| 7 | N-[(4-Chlorophenyl)-methyl]-2-cyclopropyl-4-methyl-6-morpholin-4-yl-pyridine-3-carboxylic acid amide | Example 335 in WO2012/052167 A1 | 57 |
| 8 | N-[(3-Fluorophenyl)-methyl]-2-methoxy-4-methyl-6-morpholin-4-yl-pyridine-3-carboxylic acid amide | Example 19 in WO2012/052167 A1 | 103 |
| 9 | N-[(4-Fluorophenyl)-methyl]-2-methoxy-4-methyl-6-morpholin-4-yl-pyridine-3-carboxylic acid amide | Example 39 in WO2012/052167 A1 | 53 |
| 10 | N-[(3-Fluorophenyl)-methyl]-4-methyl-6-morpholin-4-yl-2-propyl-pyridine-3-carboxylic acid amide | Example 10 in WO2012/052167 A1 | 91 |
| 11 | 2-Cyclopropyl-N-[(4-fluorophenyl)-methyl]-4-methyl-6-morpholin-4-yl-pyridine-3-carboxylic acid amide | Example 331 in WO2012/052167 A1 | 87 |
| 12 | 2-[[3-(3,4-Difluoro-phenyl)-3,3-difluoro-propyl]-sulfanyl]-N-(3-methyl-butyl)-pyridine-3-carboxylic acid amide | Example 209 in WO2010/102809 A1 | 97 |
| 13 | 2-Ethylsulfanyl-N-[(3-fluorophenyl)-methyl]-4-methyl-6-morpholin-4-yl-pyridine-3-carboxylic acid amide | Example 2 in WO2012/052167 A1 | 95 |
| 14 | N-[(4-Chlorophenyl)-methyl]-4-methyl-2-methyl-sulfanyl-6-morpholin-4-yl-pyridine-3-carboxylic acid amide | Example 168 in WO2012/052167 A1 | 59 |
| 15 | 2-Cyclopropyl-N-[(3-fluorophenyl)-methyl]-4-methyl-6-morpholin-4-yl-pyridine-3-carboxylic acid amide | Example 330 in WO2012/052167 A1 | 90 |
| 16 | 2-[[3,3-Difluoro-3-(4-fluorophenyl)-propyl]sulfanyl]-N-(3-methyl-butyl)-pyridine-3-carboxylic acid amide | Example 169 in WO2010/102809 A1 | 96 |

For the preparation of the test compounds, see referenced source.

The invention claimed is:

1. A method for treating a disease and/or disorder that is mediated at least in part by translocator protein (TSPO) activity in a patient in need thereof, wherein the disorder and/or the disease is selected from the group consisting of:
(i) neurological and neurodegenerative disorders selected from the group consisting of: ischaemic stroke, Alzheimer's disease, frontotemporal dementia, Huntington's disease, amyotrophic lateral sclerosis, Parkinson's disease, multiple sclerosis, diabetic peripheral neuropathy, chemotherapy-induced peripheral neuropathy, amyotrophic lateral sclerosis, exictotoxic brain injury, traumatic brain injury, ischaemic brain damage, cerebrovascular disorders and cerebral ischemia;
(ii) brain tumours;
(iii) immunological disorders and inflammatory diseases selected from the group consisting of: neuroinflammation and arthritis, encephalomyelitis and irritable bowel syndrome;
provided, again, the disease and/or disorder in the patient undergoing such treating is mediated at least in part by TSPO, said method comprising administering to said patient an effective amount therefor of a compound according to general formula (6-I), and achieving a modulation of TSPO activity beneficial in treating said disease and/or disorder, wherein the compound of the formula (6I) is:

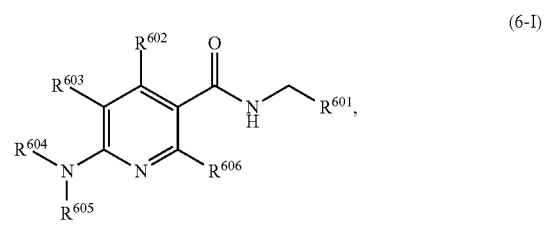

(6-I)

wherein
$R^{601}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;

$R^{602}$ represents F; Cl; Br; I; CN; $CF_3$; C(=O)H; $NO_2$; $OCF_3$; $SCF_3$; a $C_{1-4}$-aliphatic residue, a C(=O)—$C_{1-4}$ aliphatic residue, a C(=O)—O—$C_{1-4}$ aliphatic residue, a C(=O)—NH—$C_{1-4}$ aliphatic residue, a C(=O)—N($C_{1-4}$ aliphatic residue)$_2$, wherein the $C_{1-4}$ aliphatic residue may be in each case be unsubstituted or mono- or polysubstituted; a O—$C_{1-4}$-aliphatic residue, a O—C(=O)—$C_{1-4}$-aliphatic residue, a S—$C_{1-4}$-aliphatic residue, a $S(=O)_2$—$C_{1-4}$-aliphatic residue, a $S(=O)_2$—O—$C_{1-4}$-aliphatic residue, wherein the $C_{1-4}$ aliphatic residue may in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{603}$ represents H; F; Cl; Br; I; CN; $CF_3$; $SCF_3$; $NO_2$; $OCF_3$; a $C_{1-4}$-aliphatic residue, a O—$C_{1-4}$-aliphatic residue, a S—$C_{1-4}$-aliphatic residue, wherein the $C_{1-4}$ aliphatic residue may be in each case be unsubstituted or mono- or polysubstituted; a $C_{3-6}$-cycloaliphatic residue or a 3 to 6 membered heterocycloaliphatic residue, in each case unsubstituted or mono- or polysubstituted and in each case optionally bridged via a $C_{1-4}$ aliphatic group, which in turn may be unsubstituted or mono- or polysubstituted;

$R^{604}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted; aryl or heteroaryl, in each case unsubstituted or mono- or polysubstituted and in each case optionally bridged via a $C_{1-8}$ aliphatic group, which in turn may be unsubstituted or mono- or polysubstituted;
  on the condition that if $R^4$ denotes a 3 to 10 membered heterocycloaliphatic residue or a heteroaryl, the 3 to 10 membered heterocycloaliphatic residue or the heteroaryl is linked via a carbon atom;

$R^{605}$ denotes H or a $C_{1-10}$-aliphatic residue, unsubstituted or mono- or polysubstituted;

or $R^{604}$ and $R^{605}$ form together with the nitrogen atom connecting them a 3 to 10 membered heterocycloaliphatic residue, unsubstituted or mono- or polysubstituted;

$R^{606}$ represents a $C_{2-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
  on the condition that if $R^6$ denotes a 3 to 10 membered heterocycloaliphatic residue, the 3 to 10 membered heterocycloaliphatic residue is linked via a carbon atom, or denotes S—$R^{607}$, O—$R^{608}$ or $N(R^{609}R^{610})$, wherein
$R^{607}$ and $R^{608}$ in each case represent a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
  on the condition that if $R^{607}$ or $R^{608}$ denotes a 3 to 10 membered heterocycloaliphatic residue, the 3 to 10 membered heterocycloaliphatic residue is linked via a carbon atom, $R^{609}$ represents a $C_{1-10}$-aliphatic residue, unsubstituted or mono- or polysubstituted; a $C_{3-10}$-cycloaliphatic residue or a 3 to 10 membered heterocycloaliphatic residue, in each case unsubstituted or mono- or polysubstituted and in each case optionally bridged via a $C_{1-8}$ aliphatic group, which in turn may be unsubstituted or mono- or polysubstituted;
  on the condition that if $R^{609}$ denotes a 3 to 10 membered heterocycloaliphatic residue, the 3 to 10 membered heterocycloaliphatic residue is linked via a carbon atom;

$R^{610}$ denotes a $C_{1-10}$-aliphatic residue, unsubstituted or mono- or polysubstituted;

or $R^{609}$ and $R^{610}$ form together with the nitrogen atom connecting them a 3 to 10 membered heterocycloaliphatic residue, unsubstituted or mono- or polysubstituted;

in which an "aliphatic group" and an "aliphatic residue" can in each case be branched or unbranched, saturated or unsaturated, in which a "cycloaliphatic residue" and a "heterocycloaliphatic residue" can in each case be saturated or unsaturated, in which "mono- or polysubstituted" with respect to an "aliphatic group" and an "aliphatic residue" relates, with respect to the corresponding residues or groups, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue)$_2$, a NH—C(=O)—$C_{1-4}$ aliphatic residue, a NH—$S(=O)_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, $S(=O)_2OH$, a $S(=O)_2$—$C_{1-4}$-aliphatic residue, a $S(=O)_2$—O—$C_{1-4}$-aliphatic residue, a $S(=O)_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—NH($C_{1-4}$ aliphatic residue), and a C(=O)—N($C_{1-4}$ aliphatic residue)$_2$;

in which "mono- or polysubstituted" with respect to a "cycloaliphatic residue" and a "heterocycloaliphatic residue" relates, with respect to the corresponding residues, to the substitution of one or more hydrogen atoms each independently of one another by at least one substituent selected from the group consisting of F, Cl, Br, I, $NO_2$, $NH_2$, an $NH(C_{1-4}$ aliphatic residue), an $N(C_{1-4}$ aliphatic residue$)_2$, a NH—C(=O)—$C_{1-4}$ aliphatic residue, a NH—S(=O)$_2$—$C_{1-4}$ aliphatic residue, =O, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, CHO, COOH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, C(=O)—$NH_2$, a C(=O)—$NH(C_{1-4}$ aliphatic residue), and a C(=O)—$N(C_{1-4}$ aliphatic residue$)_2$;

in which "mono- or polysubstituted" with respect to "aryl" and a "heteroaryl" relates, with respect to the corresponding residues, to the substitution of one or more hydrogen atoms each independently of one another by at least one substituent selected from the group consisting of F, Cl, Br, I, $NO_2$, $NH_2$,

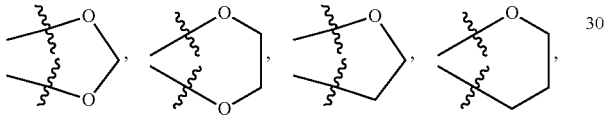

an $NH(C_{1-4}$ aliphatic residue), an $N(C_{1-4}$ aliphatic residue$)_2$, an NH—C(=O)—$C_{1-4}$ aliphatic residue, an NH—S(=O)$_2$—$C_{1-4}$ aliphatic residue, OH, $OCF_3$, a O—$C_{1-4}$-aliphatic residue, a O—C(=O)—$C_{1-4}$-aliphatic residue, SH, $SCF_3$, a S—$C_{1-4}$-aliphatic residue, S(=O)$_2$OH, a S(=O)$_2$—$C_{1-4}$-aliphatic residue, a S(=O)$_2$—O—$C_{1-4}$-aliphatic residue, a S(=O)$_2$—NH—$C_{1-4}$-aliphatic residue, CN, $CF_3$, C(=O)H, C(=O)OH, a $C_{1-4}$-aliphatic residue, a C(=O)—$C_{1-4}$-aliphatic residue, a C(=O)—O—$C_{1-4}$-aliphatic residue, a $C_{3-6}$-cycloaliphatic residue, a 3 to 6 membered heterocycloaliphatic residue, benzyl, aryl, heteroaryl, C(=O)—$NH_2$, a C(=O)—$NH(C_{1-4}$ aliphatic residue), and a C(=O)—$N(C_{1-4}$ aliphatic residue$)_2$.

2. The method according to claim 1, wherein:
$R^{601}$ represents the partial structure (6-T1), $$—(CR^{612a}R^{612b})_{m6}\text{-}R^{612c} \qquad (6\text{-}T1),$$

wherein
m6 is 0, 1 or 2, and
$R^{612a}$ and $R^{612b}$ each independently of one another represent H, F, OH, $CH_3$ or $OCH_3$, or together denote =O,
$R^{612c}$ denotes a $C_{1-4}$ aliphatic residue, unsubstituted or mono- or polysubstituted with at least one substituent selected from the group consisting of F, Cl, Br, I, CN, OH, S(=O)$_2$—$CH_3$, an unsubstituted O—$C_{1-4}$ aliphatic residue, and $CF_3$,
or denotes a $C_{3-10}$-cycloaliphatic residue or a 3 to 10 membered heterocycloaliphatic residue, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or
wherein
m6 is 0 or 2, and
$R^{612a}$ and $R^{612b}$ each independently of one another represent H, F, OH, $CH_3$ or $OCH_3$; and
$R^{612c}$ denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $OCF_2$H, $CH_2$—OH, $CH_2$—$OCH_3$, S(=O)$_2$—$CH_3$, $SCF_3$, $NO_2$, $N(CH_3)_2$,

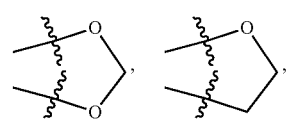 [SMILES: *OCO* ; *CCO*]

$CF_3$, CN, a $C_{1-4}$-aliphatic residue, C(=O)—$CH_3$, C(=O)—$C_2H_5$, C(=O)—O—$CH_3$, C(=O)—O—$C_2H_5$ and phenyl,
wherein phenyl may be unsubstituted or mono- or polysubstituted with at least one substituent selected from the group consisting of F, Cl, Br, I, OH, an O—$C_{1-4}$ aliphatic residue, $OCF_3$, $CF_3$, CN, a $C_{1-4}$-aliphatic residue, C(=O)—$CH_3$, C(=O)—$C_2H_5$, C(=O)—O—$CH_3$ and C(=O)—O—$C_2H_5$, $R^{602}$ represents F; Cl; Br; I; CN; $CF_3$; $NO_2$; $OCF_3$; $SCF_3$; methyl; ethyl; n-propyl; iso-propyl; n-butyl; sec.-butyl; tert.-butyl; $CH_2$—OH; $CH_2$—O—$CH_3$; $CH_2$—$CH_2$—OH; $CH_2$—$CH_2$—$OCH_3$; O-methyl; O-ethyl; O—$(CH_2)_2$—O—$CH_3$; O—$(CH_2)_2$—OH; S-Methyl; S-Ethyl; cyclopropyl, cyclobutyl, cyclopentyl, or cyclohexyl, $R^{603}$ represents H; F; Cl; Br; I; CN; $CF_3$; $SCF_3$; $NO_2$; $OCF_3$; methyl; ethyl; n-propyl; iso-propyl; n-butyl; sec.-butyl; tert.-butyl; O-methyl; O-ethyl; O—$(CH_2)_2$—O—$CH_3$; O—$(CH_2)_2$—OH; S-Methyl; or S-Ethyl, $R^{604}$ represents the partial structure (6-T2)

$$—(CR^{613a}R^{613b})_{n6}\text{-}R^{613c} \qquad (6\text{-}T2),$$

wherein
n6 denotes 0, 1, 2 or 3,
$R^{613a}$ and $R^{613b}$ each independently of one another represent H, F, $CH_3$ or $OCH_3$, or together denote =O,
$R^{613c}$ denotes a $C_{1-4}$ aliphatic residue, unsubstituted or mono- or polysubstituted with at least one substituent selected from the group consisting of F, Cl, Br, I, =O, an unsubstituted O—$C_{1-4}$ aliphatic residue, and $CF_3$,
or denotes cyclopropyl, cyclobutyl, cyclopentyl or cyclohexyl, pyrrolidinyl, morpholinyl, piperazinyl, piperidinyl or tetrahydropyranyl, in each case unsubstituted or mono- or polysubstituted with at least one substituent selected from the group consisting of F, Cl, Br, I, an unsubstituted O—$C_{1-4}$ aliphatic residue, $CF_3$, and an unsubstituted $C_{1-4}$-aliphatic residue, or denotes an aryl or heteroaryl, in each case unsubstituted or mono- or polysubstituted with at least one substituent selected from the group consisting of F, Cl, Br, I, OH, an O—$C_{1-4}$ aliphatic residue, $OCF_3$, $CF_3$, CN, and a $C_{1-4}$-aliphatic residue, $R^{605}$ denotes H, methyl or ethyl, $C_2H_4OCH_3$ or $C_3H_6OCH_3$, or $R^{604}$ and $R^{605}$ form together with the nitrogen atom connecting them a morpholinyl, piperidinyl, pyrrolidinyl, azetidinyl, oxazepanyl, tetrahydroquinolinyl, tetrahydroisoquinolinyl, thiomorpholinyl, azepanyl,

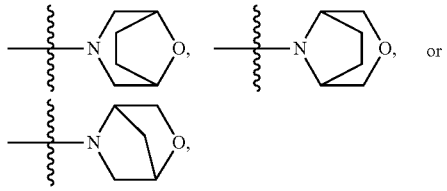

tetrahydroimidazo[1,2-a]pyrazinyl, octahydropyrrolo[1,2-a]pyrazinyl,

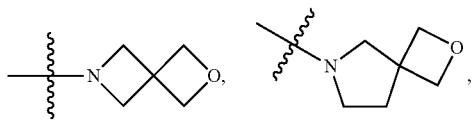 [SMILES: *N1CC2(COC2)C1 ; *N1CCC2(COC2)C1]

dihydroindolinyl, or dihydroisoindolyl, in each case unsubstituted or mono- or polysubstituted with at least one substituent selected from the group consisting of F, Cl, OH, =O, C(=O)—OH, O-methyl, O-ethyl, $OCF_3$, $SCF_3$, $CF_3$, C(=O)—$CH_3$, C(=O)—$OCH_3$, $CH_2CF_3$, $CH_2OH$, $CH_2$—$OCH_3$, $CH_2CH_2$—$OCH_3$, methyl, ethyl, n-propyl, 2-propyl, cyclopropyl, and cyclobutyl, $R^{606}$ denotes ethyl, n-propyl, 2-propyl, n-butyl, isobutyl, sec.-butyl, tert.-butyl, n-pentyl, isopentyl, neopentyl, n-hexyl, $CH_2$—$CH(CH_3)(C_2H_5)$, $C(CH_3)_2(C_2H_5)$, $CH_2$—$OCH_3$, $C_2H_4$—$OCH_3$, $C_3H_6$—$OCH_3$, cyclopropyl, cyclobutyl, or tetrahydropyranyl, ethenyl or propenyl (—$CH_2CH=CH_2$, —$CH=CH$—$CH_3$, —C((=$CH_2$—$CH_3$), in each case unsubstituted, or $R^{606}$ denotes S—$R^{607}$ or O—$R^{608}$ wherein $R^{607}$ and $R^{608}$ in each case denote methyl, ethyl, n-propyl, 2-propyl, n-butyl, isobutyl, sec.-butyl, tert.-butyl, n-pentyl, isopentyl, neopentyl, or n-hexyl, in each case unsubstituted or mono- or polysubstituted with at least one substituent selected from the group consisting of F, Cl, OH, N($C_{1-4}$ aliphatic residue) and an O—$C_{1-4}$-aliphatic residue, or in each case denote $CH_2$-cyclopropyl or oxetanyl, wherein the $C_{1-4}$-aliphatic residue in each case is unsubstituted, or $R^{606}$ denotes N($R^{609}R^{610}$), wherein $R^{609}$ denotes methyl, C(=O)—$CH_3$, ethyl, n-propyl, 2-propyl, n-butyl, isobutyl, sec.-butyl, tert.-butyl, n-pentyl, isopentyl, neopentyl, or n-hexyl, $R^{610}$ denotes methyl or ethyl, or $R^{609}$ and $R^{610}$ form together with the nitrogen atom connecting them a morpholinyl, piperidinyl, pyrrolidinyl, or azetidinyl, in each case unsubstituted.

* * * * *